(12) United States Patent
Kosuda et al.

(10) Patent No.: US 6,198,951 B1
(45) Date of Patent: Mar. 6, 2001

(54) REFLECTION PHOTODETECTOR AND BIOLOGICAL INFORMATION MEASURING INSTRUMENT

(75) Inventors: Tsukasa Kosuda; Yutaka Kondo, both of Matsumoto; Hajime Kurihara; Norimitsu Baba, both of Shimosuwa-machi, all of (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 09/297,438

(22) PCT Filed: Sep. 4, 1998

(86) PCT No.: PCT/JP98/03972

§ 371 Date: Apr. 30, 1999

§ 102(e) Date: Apr. 30, 1999

(87) PCT Pub. No.: WO99/12469

PCT Pub. Date: Mar. 18, 1999

(30) Foreign Application Priority Data

Sep. 5, 1997 (JP) .................................................. 9-241426
Nov. 11, 1997 (JP) .................................................. 9-308913

(51) Int. Cl.$^7$ ....................................................... A61B 5/00
(52) U.S. Cl. ................................................................ 600/323
(58) Field of Search ................................. 600/322, 323, 600/336, 310, 316, 330, 340, 344

(56) References Cited

U.S. PATENT DOCUMENTS

| | | | |
|---|---|---|---|
| 5,285,784 | * | 2/1994 | Secker ................................. 600/323 |
| 5,431,170 | * | 7/1995 | Matthews .............................. 600/323 |
| 5,524,617 | * | 6/1996 | Mannheimer ......................... 600/323 |
| 5,645,060 | * | 7/1997 | Yorkey ................................... 600/323 |
| 5,830,137 | * | 11/1998 | Scharf .................................... 600/323 |

FOREIGN PATENT DOCUMENTS

| | | |
|---|---|---|
| 50-16180 | 12/1975 | (JP) . |
| 60-135029 | 7/1985 | (JP) . |
| 3-129107 | 12/1991 | (JP) . |
| 5-506802 | 10/1993 | (JP) . |
| 7-88092 | 4/1995 | (JP) . |
| 7-155312 | 6/1995 | (JP) . |
| 7-308299 | 11/1995 | (JP) . |
| 9-114955 | 5/1997 | (JP) . |
| 9-299342 | 11/1997 | (JP) . |

\* cited by examiner

*Primary Examiner*—John P. Lacyk
(74) *Attorney, Agent, or Firm*—Michael T. Gabrik

(57) ABSTRACT

When emitted light from LED 31 is incident on photodiodes 32 and 33 with luminance Pa and Pb, currents ia and ib are generated according to luminance Pa and Pb. When outside light is incident through the finger tissues on photodiodes 32 and 33 with luminance Pc, current ic is produced. The current i1 (=ia+ic) generated by photodiode 32, and the current i2 (=−ib−ic) generated by photodiode 33, are added at node X, and the current ic corresponding to outside light is thus cancelled. In addition, photodiodes 32 and 33 are disposed at different distances from LED 31. As a result, the current flowing to opamp 34 is current ia corresponding to luminance Pa because luminance Pb is extremely low. The opamp 34 then applies a current voltage conversion to generate pulse wave signal Vm.

19 Claims, 27 Drawing Sheets

REFLECTION PHOTODETECTOR AND BIOLOGICAL INFORMATION MEASURING INSTRUMENT

BACKGROUND OF THE INVENTION

1. Field of the Invention

The present invention relates to a reflection type photodetection apparatus suitable for detecting the intensity of the reflection of an emitted light reflected by a detected object without being affected by outside light, and relates further to a biological information measuring apparatus comprising this reflection type photodetection apparatus for measuring a pulse wave, pulse, the pitch of body movement or other biological information.

2. Description of Related Art

Devices for measuring biological information such as the pulse and body motion include electronic devices for optically detecting a change in blood volume to display biological information based on the detected result. This type of optical pulse wave measuring device (biological information measuring apparatus) emits light from an LED (light emitting diode) or other light emitting element to the finger tip, for example, and detects light reflected from the body (blood vessel) by means of a photodiode or other light detecting element. It is therefore possible to detect a change in blood flow produced by the blood pulse wave as a change in the amount of detected light. The change in the pulse rate or pulse wave is then displayed based on the pulse wave signal thus obtained. Infrared light is conventionally used as the light emitted from the light emitting element.

It should be noted here that when outside light such as natural light or fluorescent light is incident on the photodetector, the amount of detected light fluctuates with the variation in the incidence of outside light. More specifically, the fingertip or other detected part is typically covered by a light shield in a conventional biological information measuring apparatus to suppress the effects of outside light because this outside light is noise (external disturbance) to the pulse wave signal to be detected.

The luminance of natural light is, however, significantly greater than the luminance of light emitted from the light emitting element when directly exposed to natural light, such as when outdoors. A problem with a conventional biological information measuring apparatus is, therefore, that when it is used where exposed to outside light, such as outdoors, some of the outside light inevitably passes though the finger tissues and reaches the photodetector no matter how large the light shield for blocking outside light is made, and pulse detection errors resulting from variations in the luminance of outside light occur easily. Such conventional biological information measuring apparatuses are therefore limited to use in places where they are not exposed to outside light, or where the luminance of any outside light is constant. This limitation can be overcome by using an even larger light shield structure, but the size of the biological information measuring apparatus then cannot be reduced.

To resolve this problem, Japan Unexamined Utility Model Application Publication (jikkai) S57-74009 (1982-74009) teaches a pulse wave sensor comprising, in addition to a pulse wave detector for detecting a pulse wave, an outside light detector for detecting outside light. This outside light detector is covered with a filter having the same transmission characteristics as the body tissues so that the pulse wave sensor can compensate for the effects of outside light based on the result of outside light detection by the outside light detector.

There are, however, individual differences in the transmission of outside light, and it is therefore difficult using the above-noted technology to accurately compensate for an outside light component. Furthermore, the path of outside light to the pulse wave detector varies according to the relative positions of the pulse wave detector and the finger. That is, each time the detection device is used, the path length from the point of incidence of outside light on the tissue to the pulse wave detector changes. It is therefore not possible to accurately compensate for an outside light component even by providing a filter with constant transmission characteristics.

A conventional device for detecting the pitch of body movement typically uses a built-in acceleration detector to detect movement of the body, and determines the pitch of body movement from the body movement signal. A pedometer, for example, uses a piezoelectric element PZT as a compact acceleration detector, and detects the speed at which the user is moving by applying wave shaping to the detected body movement signal.

Devices combining the above-noted acceleration detector and an optical pulse wave sensor are also available as portable pulsimeters capable of measuring the pulse while the user is exercising. Such portable pulsimeters apply a fast Fourier transform process (FFT) to the body movement signal detected by the acceleration detector and the pulse wave signal detected by the optical pulse wave sensor to separately detect a body movement spectrum indicative of the body movement signal and a pulse wave spectrum indicative of the pulse wave signal. The pulse wave spectrum and body movement spectrum are then compared, the frequency component corresponding to the body movement spectrum is removed from the pulse wave spectrum, and the frequency with the greatest spectrum power is then removed from the remaining spectrum to determine the fundamental frequency of the pulse wave signal. The pulse rate is then calculated based on the fundamental frequency of the pulse wave signal. A conventional pulsimeter therefore applies two FFT operations, and calculates the pulse rate based on the results of these FFT operations.

The present inventors have also proposed in Japanese Patent Application H5-241731 (1993-241731) a device enabling pulse rate detection while the user is exercising using only an optical pulse wave sensor and not using an acceleration detector. This device focuses on the difference in the absorption characteristics of oxygenated hemoglobin in arterial blood and reduced hemoglobin in venous blood. The operating principle of this device uses the long wavelength (e.g., 940 nm) of the absorption characteristic of oxygenated hemoglobin compared with the absorption characteristic of reduced hemoglobin, and the long wavelength (e.g., 660 nm) of the absorption characteristic of reduced hemoglobin compared with the absorption characteristic of oxygenated hemoglobin to detect pulse wave signals, applies a FFT operation to both pulse wave signals, and determines the fundamental frequency of the pulse wave signals by comparing the results of the FFT operations.

Small, low cost acceleration detectors used in pedometers are sensitive in only one direction, therefore cannot detect movement in all directions, and thus cannot accurately detect body movement. This problem can be resolved using a acceleration detector with three axes, but this results in a more complex construction, and makes it difficult to reduce the size.

A further problem with the above-described pulsimeters that use an acceleration detector is that it is not possible to continue detecting the pulse rate while exercising if the acceleration detector fails. In addition, whether or not an acceleration detector is used, conventional pulsimeters require two FFT operations, thereby resulting in a more complex configuration and requiring a further process to determine the fundamental frequency of the pulse wave signal from the frequency analysis result.

SUMMARY OF THE INVENTION

The present invention is therefore directed to resolving the aforementioned problems, and includes in its primary objects the following. That is, a first object of the present invention is to provide a reflection type photodetection apparatus of simple configuration for detecting the intensity of the reflection of emitted light reflected by a detected object without being affected by outside light. A second object of the present invention is to provide a biological information measuring apparatus of simple configuration for accurately measuring body movement with high reliability. A third object of the present invention is to provide a biological information measuring apparatus that is suitable for measuring a pulse wave, pulse, and other biological information using a reflection type photodetection apparatus.

The present invention is directed to resolving the aforementioned problems, and to achieve the above-noted first object provides a reflection type photodetection apparatus as follows. This reflection type photodetection apparatus has a light emitting element for emitting light to a detected object, and detects the intensity of reflected light, which is emitted light from this light emitting element reflected by the detected object. This reflection type photodetection apparatus comprises: a first photoelectric conversion element for receiving and converting light to an electrical signal; a second photoelectric conversion element for receiving and converting light to an electrical signal; and a difference detection means for detecting and outputting the difference between an output signal of the first photoelectric conversion element and an output signal of the second photoelectric conversion element; wherein the first photoelectric conversion element, second photoelectric conversion element, and light emitting element are arranged so that the distance from the photodetection center of the second photoelectric conversion element to the light emitting center of the light emitting element is different from the distance from the light emitting center of the light emitting element to the photodetection center of the first photoelectric conversion element, and the first photoelectric conversion element and second photoelectric conversion element are positioned so that outside light reaches each with substantially equal intensity.

This reflection type photodetection apparatus can be applied to a biological information measuring apparatus. In this case, the light emitting element emits light to a detection site of the body, the difference detection means detects pulsation of the blood flow as the difference signal, and biological information indicative of a body condition is measured based on the detection result.

This reflection type photodetection apparatus can also be expressed as a reflected light detection method. This aspect of the invention comprises: a step for emitting emitted light from a light emitting element to a detected object; a step for generating a first signal by detecting and photoelectrically converting reflected light reflected by the detected object, and outside light, by means of a first photoelectric conversion element; a step for generating a second signal by detecting and photoelectrically converting outside light by means of the second photoelectric conversion element; and a step for detecting the intensity of the reflected light by calculating the difference between the first signal and second signal.

To achieve the above-noted second object, the present invention also provides a biological information measuring apparatus as follows. This biological information measuring apparatus comprises a light emitting means for emitting light to a detection site of a body, and a photodetection means for detecting light emitted by the light emitting means into the body and generating a body movement signal according to the detected light quantity, and measuring movement of the body based on the body movement signal as biological information, and is characterized by generating the body movement signal based on the result of a measurement in a wavelength range of 600 nm and above. It should be noted that the invention of this biological information measuring apparatus can also be expressed as a biological information measurement method.

It should be further noted that the wavelength of emitted light from the light emitting means can be 600 nm or above. In addition, a wavelength of light received by the photodetection means from the light emitting means can be 600 nm or above.

In addition, the biological information measuring apparatus can further comprise a frequency analysis means for frequency analyzing the body movement signal measured by the photodetection means, and generating a body movement spectrum; and a pitch detection means for extracting a fundamental frequency based on the body movement spectrum analyzed by the frequency analysis means, and detecting the pitch of body movement based on the extracted fundamental frequency.

Furthermore, to achieve the above-noted third object, the present invention provides a biological information measuring apparatus as follows. This biological information measuring apparatus comprises: a light emitting means for emitting light to a detection site on the body, and a body movement detection means for detecting light emitted by this light emitting means into the body, and generating a body movement signal according to the amount of detected light; a light emitting means for emitting light to a detection site on the body, and a pulse wave detection means for detecting light emitted by this light emitting means into the body, and generating a pulse wave signal according to the amount of detected light; and a biological information generating means for generating biological information indicative of a body condition based on this body movement signal and pulse wave signal; wherein the body movement detection means generates the body movement signal based on a measurement made in a wavelength range of 600 nm or greater, and the pulse wave detection means generates the pulse wave signal based on a measurement made in a wavelength range of 600 nm or below. It should be noted that the invention of this biological information measuring apparatus can also be expressed as a biological information measurement method.

The biological information generating means in this case can comprise a comparison operator for comparing the body movement signal and pulse wave signal such that biological information is generated based on the result of this comparison.

In addition, the comparison operator can subtract the body movement signal from the pulse wave signal, and output the difference signal.

Furthermore, the biological information generating means can frequency analyze the difference signal output by the comparison operator to generate pulse wave analysis data from which the body movement component is removed, and generate biological information for the body based on this pulse wave analysis data.

Furthermore, the biological information generating means can apply an autocorrelation function to the difference signal output by the comparison operator to generate autocorrelated pulse wave data, and generate biological information based on this autocorrelated pulse wave data.

Furthermore, the biological information generating means can be comprised to detect a degree of irregularity in body movement based on the body movement signal, and determine whether to perform an autocorrelation operation based on the result of this detection. If an autocorrelation operation is to be performed, it applies an autocorrelation function to the difference signal output by the comparison operator to generate autocorrelated pulse wave data and generates biological information based on this autocorrelated pulse wave data. If an autocorrelation operation is not performed, it generates biological information based on the difference signal.

Moreover, the photodetection means of the body movement detection means is preferably a first photodiode for outputting an electrical signal according to the amount of detected light; the photodetection means of the pulse wave detection means is a second photodiode for outputting an electrical signal according to the amount of detected light; and the comparison operator outputs the difference signal from a node connected in series with the first photodiode and second photodiode.

In addition, to achieve the above-noted third object, the present invention provides in addition to the above-described biological information measuring apparatus a biological information measuring apparatus as follows.

This biological information measuring apparatus has a light emitting means for emitting light to a wrist or arm, and a photodetection means for detecting light emitted by the light emitting means into the body and generating a pulse wave signal according to the amount of detected light, and generates biological information indicative of a body condition based on a pulse wave signal measured in a 500 nm to 600 nm wavelength range.

The primary wavelength of light emitted by the light emitting means in this case is preferably 500 nm to 600 nm. In addition, the primary wavelength of light detected by the photodetection means is 500 nm to 600 nm.

BEST MODES FOR ACHIEVING THE INVENTION

A. Embodiment 1

A-1. Configuration of the First Embodiment

A biological information measuring apparatus according to a first embodiment of the present invention is described below with reference to the accompanying figures.

A-1-1: Overall Configuration

Figure 1:
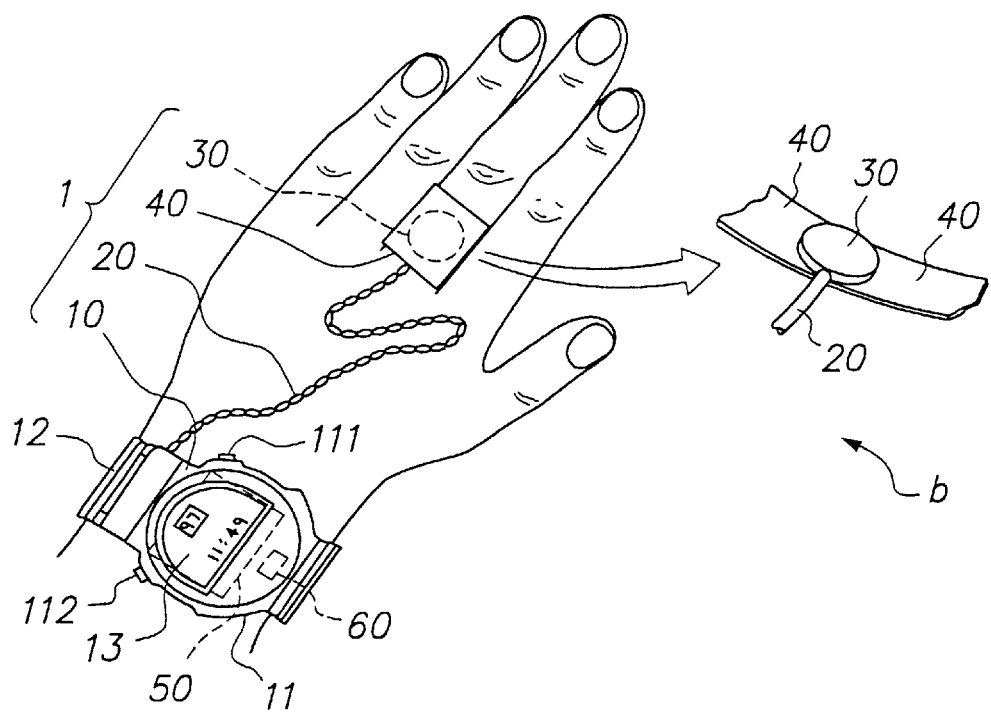
FIG. 1 is an external view of a biological information measuring apparatus according to a first embodiment of the present invention.

FIG. 1 is an external view of a biological information measuring apparatus according to a first embodiment of the present invention. As shown in this figure, a pulse wave measuring device 1 (biological information measuring apparatus) comprises primarily a main body 10 having a wristwatch construction; a cable 20 leading from this main body; a sensor unit 30 disposed at the end of this cable 20; and a sensor holding band 40 for holding this sensor unit 30 on a finger.

The main body 10 comprises a watch case 11 with a built-in clock function, and a wristband 12 for holding this watch case 11 on the wrist. The surface of the watch case 11 has a liquid crystal display 13 for displaying, in addition to the current time and date, pulse wave information (biological information) based on a detection result from the sensor unit 30. Built in to the watch case 11 are an acceleration detector 60 and data processing circuit 50 to which a pulse wave signal Vm, that is, the detection result from the sensor unit 30, is supplied. Body movement such as swinging the wrist is detected by the acceleration detector 60 as body movement signal Vt. The data processing circuit 50 processes the pulse wave signal Vm and body movement signal Vt to generate the pulse rate and other biological information. Note that buttons 111 and 112 are also provided on the outside of the watch case 11 for setting the time, changing the display mode, and other operations.

The power supply for the pulse wave measuring device 1 is a battery in the watch case 11. Cable 20 supplies power from the battery to the sensor unit 30, and enables detection results to be input from the sensor unit 30 to the data processing circuit 50 in the watch case 11. The sensor holding band 40 in this exemplary embodiment has a hook-and-loop fastener attached thereto so that, as shown in FIG. 1, it can hold sensor unit 30 tight to the base of the finger.

Figure 2:
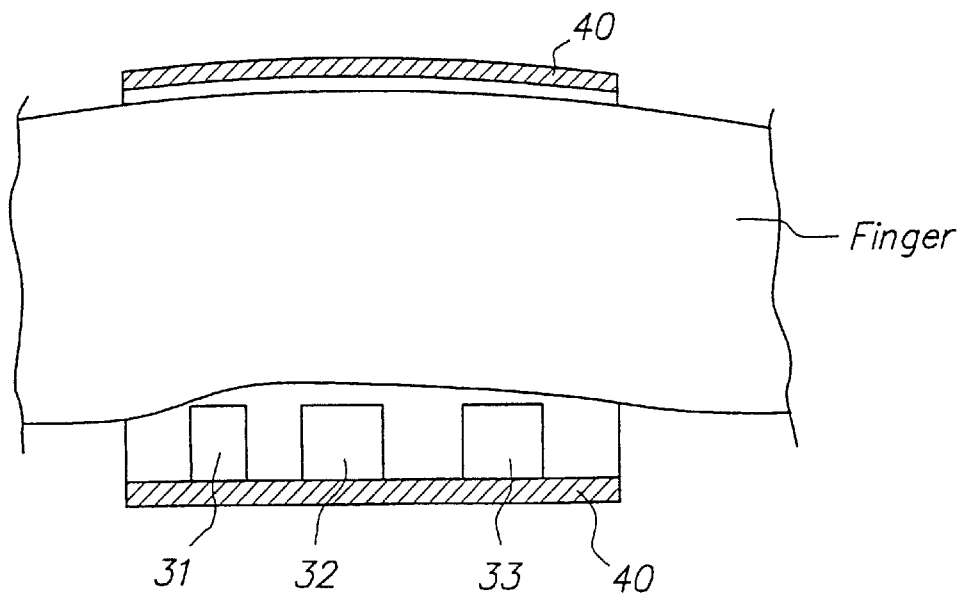
FIG. 2 is a typical section view of a sensor unit 30 according to this preferred embodiment when worn.

A disk-shaped sensor unit 30 is fixed on the inside surface of the sensor holding band 40 such that light-emitting diode (referred to below as LED) 31 and photodiodes 32 and 33 are held facing the finger as illustrated in FIG. 2. When the LED 31 emits light to the finger, emitted light is absorbed by hemoglobin in the blood flowing through blood capillaries in the finger tissues, emitted light that is not absorbed is reflected by the tissue, and the reflected light is received by the photodiodes 32 and 33 and converted to an electrical signal according to the amount of received light.

The sensor holding band 40 material is preferably one that does not pass light. Therefore, even when the pulse wave measuring device 1 is used outdoors, natural light will not be directly incident on the photodiodes 32 and 33.

A-1-2: Configuration of the Sensor Unit 30

Figure 3:
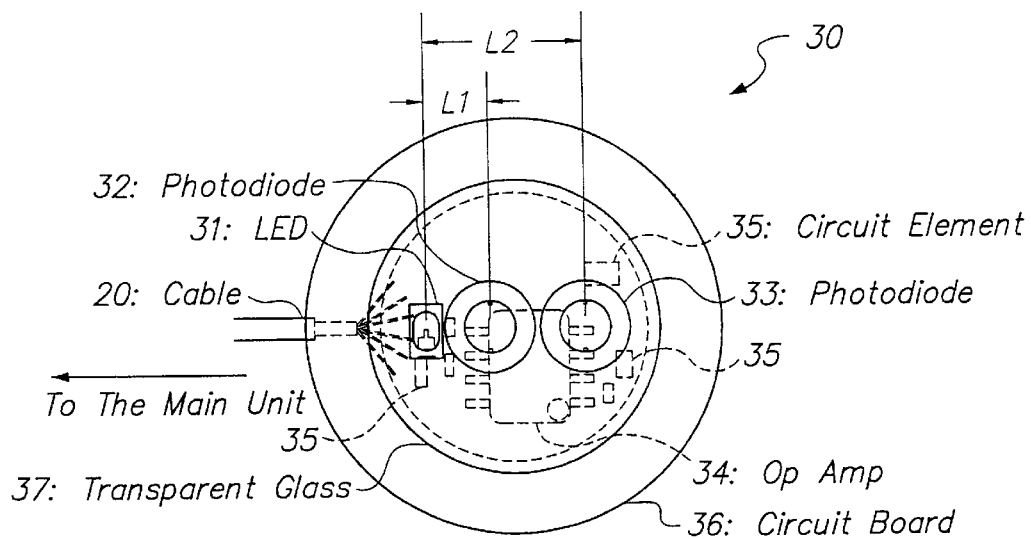
FIG. 3 is a plan view of a sensor unit 30 according to this preferred embodiment.
Figure 4:
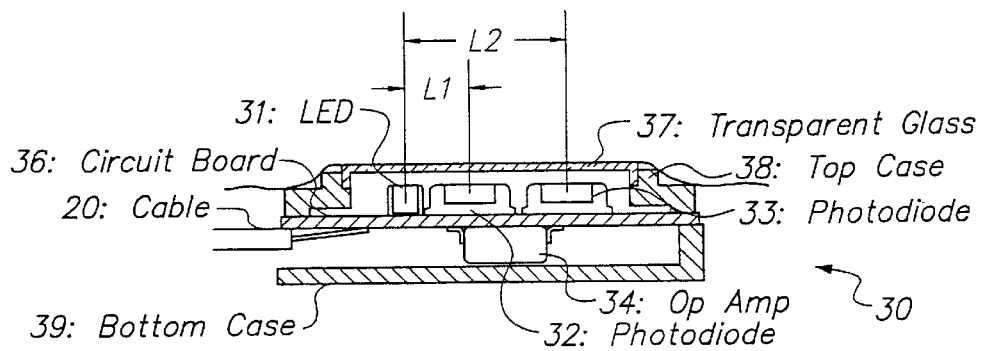
FIG. 4 is a section view of a sensor unit 30 according to this preferred embodiment.

The configuration of the sensor unit 30 (reflection type photodetection apparatus) is described next. FIG. 3 is a plan view of the sensor unit, and FIG. 4 is a section view of the sensor unit. As shown in FIGS. 3 and 4, the LED 31 and photodiodes 32 and 33 are formed on a surface of a circuit board 36. An opamp 34 and circuit element 35 are formed on the back of circuit board 36. The opamp 34 and circuit element 35 amplify the difference between the output signals from photodiodes 32 and 33. This is described further below. In addition, a top case 38 in which is held transparent glass 37 is formed around the edge of the top of circuit board 36. This transparent glass 37 protects LED 31 and photodiodes 32 and 33 while enabling the passage of light. A bottom case 39 having an opening for passing cable 20 is also formed on the back of circuit board 36.

In this example the opamp 34 is in sensor unit 30. Even if a high input impedance opamp 34 is housed in the main body 10, the wiring length is increased by the length of cable 20, and cable 20 acts as an antenna for noise. The opamp 34 is therefore housed inside the sensor unit 30 to shorten the wiring length from the photodiodes 32 and 33 to the opamp 34, and thus prevent the introduction of noise.

As will be known from the figures, the LED 31 and photodiodes 32 and 33 are arranged in a line in this exemplary embodiment, and are more specifically arranged so that distance L1 is less than distance L2 (L1<L2) where distance L1 is the distance from the light emitting center of LED 31 to the photodetection center of photodiode 32, and distance L2 is the distance from the light emitting center of LED 31 to the photodetection center of photodiode 33. That is, photodiode 33 is disposed so that the distance L2 from the photodetection center thereof to the light emitting center of the LED 31 is different from the distance L1 from the light emitting center of LED 31 to the photodetection center of photodiode 32. As a result, the optical path from LED 31 to photodiode 33 is longer than the path from LED 31 to photodiode 32.

It should also be noted that emitted light from LED 31 is also absorbed and dispersed by body tissues, and not just by hemoglobin in the blood, though there is some variance with wavelength. Therefore, once the path length reaches a certain length, emitted light is absorbed and dispersed by the transmission medium, that is, body tissues, and substantially no reflected light is incident on the photodiodes 32 and 33. In this exemplary embodiment, distance L1 is determined so that there is little absorption and dispersion by tissue, and blood flow can be detected by the photodiode 32, and distance L2 is determined so that there is substantially no incidence of reflected light on photodiode 33. A pulse wave signal is therefore superposed on the output signal from photodiode 32, and a pulse wave signal does not appear in the output signal of photodiode 33.

Figure 5:
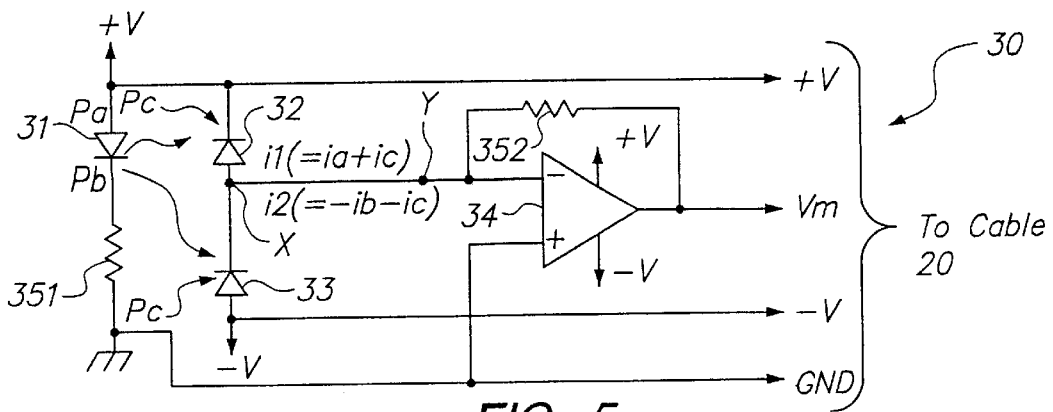
FIG. 5 is a circuit diagram showing the electrical configuration of a sensor unit 30 according to this preferred embodiment.

FIG. 5 is a circuit diagram showing the electrical configuration of the sensor unit. As shown in the figure, the anode of the LED 31 is connected to positive power source +V, and the cathode is to ground through resistor 351. Resistor 351 operates as a current limiting resistor to assure that a desired current flows to LED 31.

The cathode of photodiode 32 is connected to positive power source +V, and the anode is connected to the cathode of photodiode 33. The anode of photodiode 33 is connected to negative power source −V. Node X between photodiodes 32 and 33 is connected to a negative input terminal to opamp 34, and the positive input terminal to the opamp 34 is to ground. The output signal of opamp 34 is fed back to the negative input terminal thereof through resistor 352. The input impedance to this opamp 34 is extremely high, and the gain is also high. There is a virtual short circuit between the negative input terminal and positive input terminal of opamp 34. As a result, photodiodes 32 and 33 are reverse biased, and when light is incident thereto generate a current determined by the amount of light detected.

Figure 6:
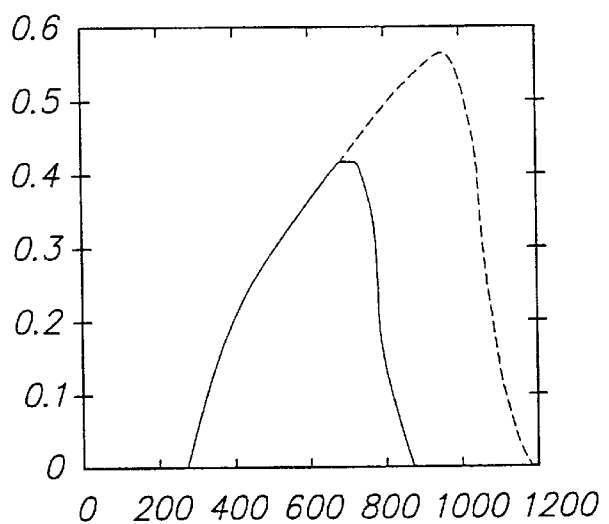
FIG. 6 is a graph of the spectral sensitivity characteristic of photodiodes 32 and 33 according to this preferred embodiment.
Figure 7:
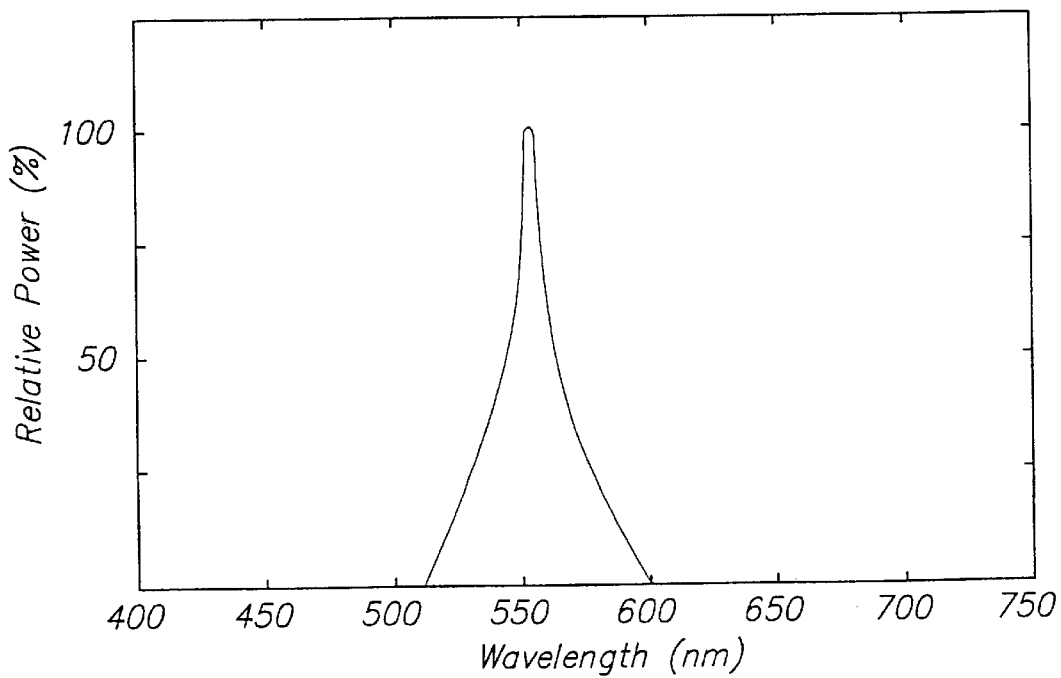
FIG. 7 is a graph of the light emitting characteristic of an LED 31 according to this preferred embodiment.

The solid line in FIG. 6 is indicative of the spectral sensitivity of photodiodes 32 and 33 in this exemplary embodiment. From this figure we know that photodiodes 32 and 33 have a sensitivity peak at approximately 700 nm. As shown in FIG. 7, the light emission characteristic of photodiode 32 has a peak at approximately 560 nm with a peak width at half height of approximately 25 nm.

Figure 8:
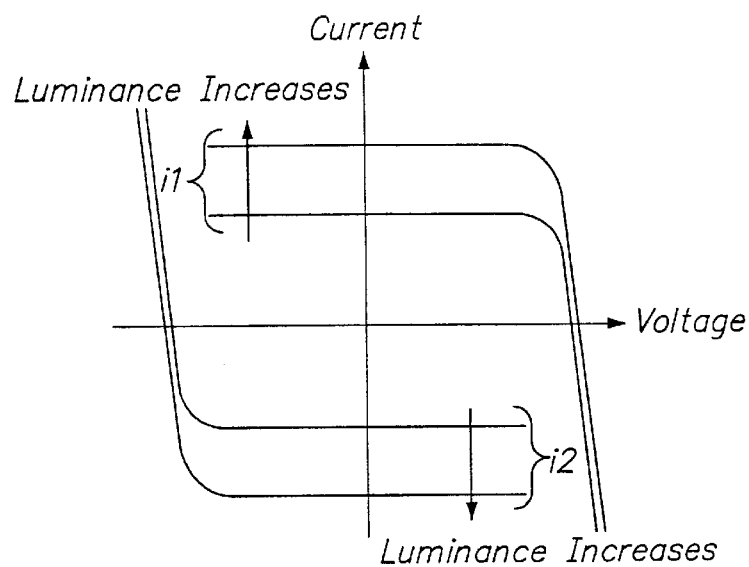
FIG. 8 shows the relationship between voltage and current at node X when the circuit is interrupted at point Y in FIG. 5.

The principle of photoelectric conversion by a photodiode is that when light is incident to a depletion layer formed by a reverse bias between the anode and cathode, electrons become excited and release free electrons, which rebond with holes and permit current to flow from the cathode to the anode. Therefore, if the direction of current i1 and i2 is as shown in FIG. 5, i1 is positive and i2 is negative. FIG. 8 shows the relationship between voltage and current at node X when the circuit is interrupted at point Y in FIG. 5. As shown in the figure, when the luminance incident on photodiode 32 increases as shown in the figure, current i1 increases, and when the luminance incident on photodiode 33 increases, current i2 decreases.

It should be noted that the light incident on photodiodes 32 and 33 includes outside light in addition to the emitted light of photodiode 32 reflected light by the tissues. For example, when pulse wave measuring device 1 is used outdoors, natural light is incident from skin that is not covered by the sensor holding band 40 on the finger, passes tissues in the finger, and is incident on photodiodes 32 and 33 as outside light. Because the finger is uniformly exposed to natural light, the luminance (intensity) of outside light incident on the photodiodes 32 and 33 is equal if the distance between the photodiodes 32 and 33 is short. In this exemplary embodiment, therefore, the relative positions of the photodiodes 32 and 33 are determined so that the luminance (intensity) of outside light is equal.

Let us assume that Pa and Pb are the luminance of light incident on photodiodes 32 and 33 as reflections of emitted light from the photodiode 32, and that Pc is the luminance of outside light. In addition, ia, ib, and ic are the currents generated in response to luminance Pa, Pb, and Pc. In this exemplary embodiment, i1 and i2 shown in FIG. 5 can be derived from the following equations.

$$i1 = ia + ic$$

$$i2 = -ib - ic$$

Figure 9:
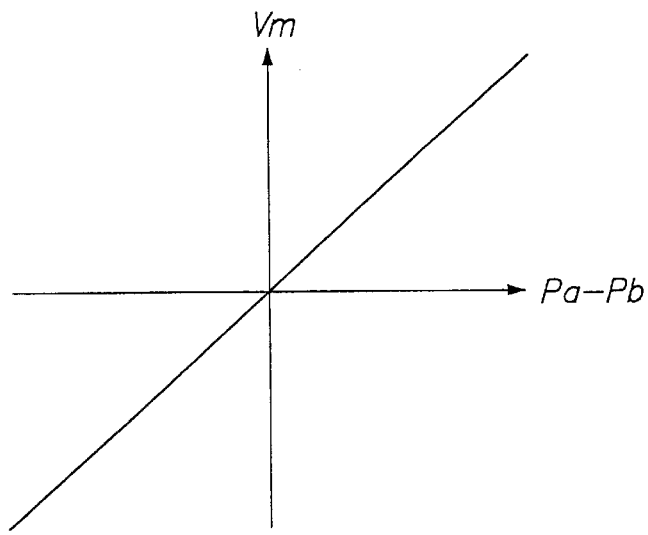
FIG. 9 is a graph showing the relationship between brightness Pa–Pb and a pulse wave signal according to this preferred embodiment.

Current i1 and current i2 are added at node X, and the current i1+i2 flowing to opamp 34 is therefore (ia−ib). That is, currents ic and −ic generated for outside light luminance Pc are mutually cancelling, and a current dependent on the reflected light of LED 31 flows to opamp 34. As a result, pulse wave signal Vm is dependent only on luminance Pa and Pb. FIG. 9 shows the relationship between pulse wave signal Vm and luminance Pa and Pb.

It should be further noted that the relative positions of LED 31 and photodiodes 32 and 33 are determined, as described above, so that reflected light is incident to photodiode 32, and there is substantially no incidence of reflected light on photodiode 33. Therefore, current i1+i2 can be approximated by the following equation because luminance Pb is extremely low relative to luminance Pa.

$$i1 + i2 = ia - ib \approx ia$$

Therefore, pulse wave signal Vm is dependent on the luminance Pa of reflected light incident on photodiode 32.

When a sensor unit 30 thus comprised is held at the base of a finger by sensor holding band 40 as shown in FIG. 1, LED 31 and photodiodes 32 and 33 are held with the light emitting surface and photodetecting surfaces thereof facing the surface of the finger. When the LED 31 then emits light to the finger while thus positioned, light reflected from the body is detected by photodiodes 32 and 33. It should be noted that even if outside light enters from skin that is not covered by the sensor holding band 40 on the finger and is incident to photodiodes 32 and 33, the outside light components are mutually cancelled. It is therefore possible to input only a pulse wave signal Vm corresponding to pulsation through cable 20 to main body 10.

A-1-3: Configuration of the Data Processing Circuit 50

Figure 10:
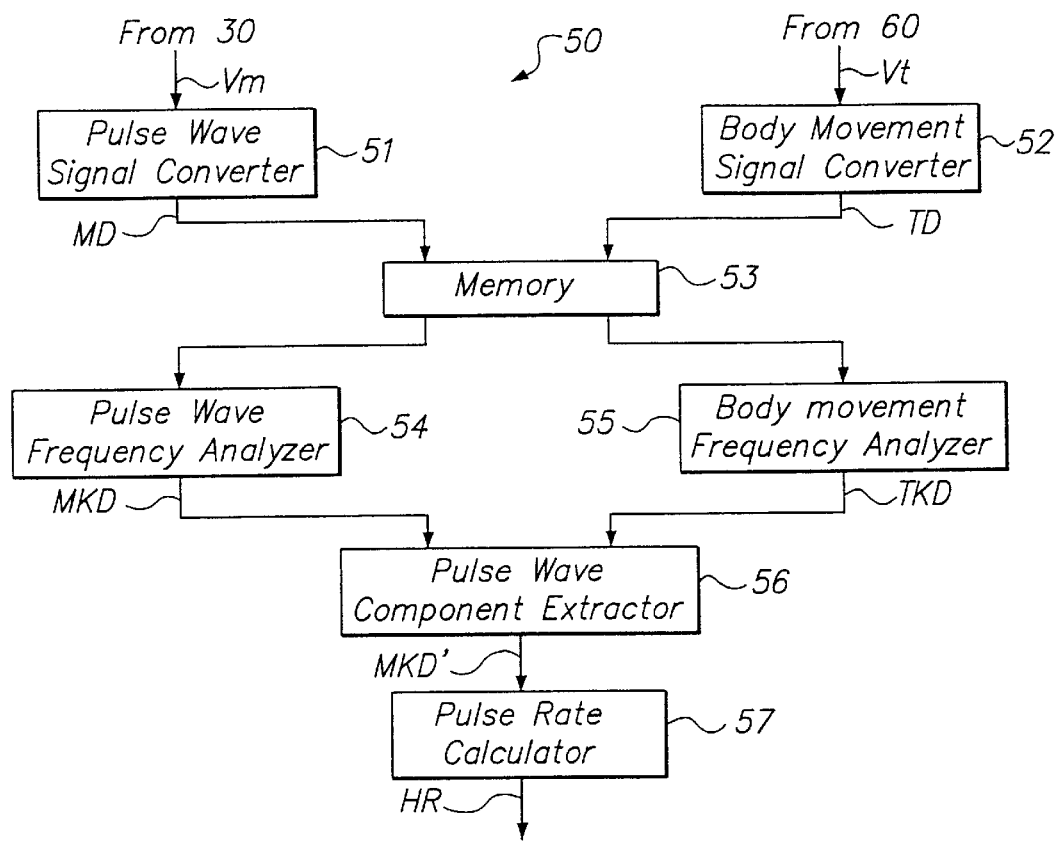
FIG. 10 is a function block diagram of data processing circuit 50 according to this preferred embodiment.

The data processing circuit 50 is described next with reference to FIG. 10. FIG. 10 is a block diagram of the functions of a data processing circuit. In FIG. 10, reference numeral 51 is a pulse wave signal converter for converting pulse wave signal Vm from sensor unit 30 from an analog signal to a digital signal, and outputting it as pulse wave data MD; 52 is a body movement signal converter for converting body movement signal Vt from an analog signal to a digital signal, and outputting it as body movement data TD; 53 is RAM or other memory for storing pulse wave data MD and body movement data TD.

Reference numeral 54 is a pulse wave frequency analyzer for generating pulse wave analysis data MKD by frequency analyzing pulse wave data MD read from memory 53; and 55 is a body movement frequency analyzer for generating body movement analysis data TKD by frequency analyzing body movement data TD read from memory 53. Various methods can be used for this frequency analysis. The present exemplary embodiment uses a fast Fourier transform (FFT) because analysis can be completed in a short operating time.

Reference numeral 56 is a pulse wave component extractor for generating pulse wave analysis data after body movement component removal MKD', that is, pulse wave analysis data MKD from which the body movement component has been removed, based on pulse wave analysis data MKD and body movement analysis data TKD. More specifically, it removes the spectrum frequency component corresponding to the spectrum frequencies of body movement analysis data TKD from the spectrum frequency components of pulse wave analysis data MKD to generate pulse wave analysis data after body movement component removal MKD'.

Reference numeral 57 is a pulse rate calculator for determining the fundamental frequency Fm1 of the pulse wave component based on the pulse wave analysis data after body movement component removal MKD', and calculating 60/Fm1 to generate pulse rate HR. Pulse rate HR is thus supplied to liquid crystal display 13, and displayed. The user can thus know his or her own pulse rate even while jogging or exercising.

It should be further noted that data processing circuit 50 more specifically comprises a central processing unit (CPU), random access memory (RAM as working memory for the CPU, and read-only memory (ROM) for storing a program embodying the above-described functions.

A-2. Operation of the First Embodiment

The operation of this preferred embodiment of the present invention is described next with reference to the accompanying figures.

A-2-1: Operation of the sensor unit 30

Figure 11:
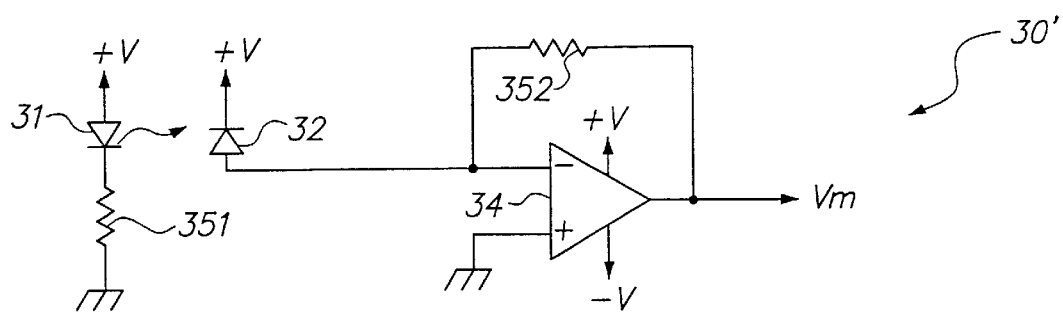
FIG. 11 is a circuit diagram of a sensor unit 30' prepared for comparison.

The operation of sensor unit 30 is first described in comparison with the operation of a comparative sensor unit. FIG. 11 is a circuit diagram of a comparative sensor unit 30' prepared for comparative purposes. This comparative sensor unit 30' is the sensor unit 30 shown in FIG. 5 without photodiode 33, and is equivalent to a conventional sensor unit.

Figure 12:
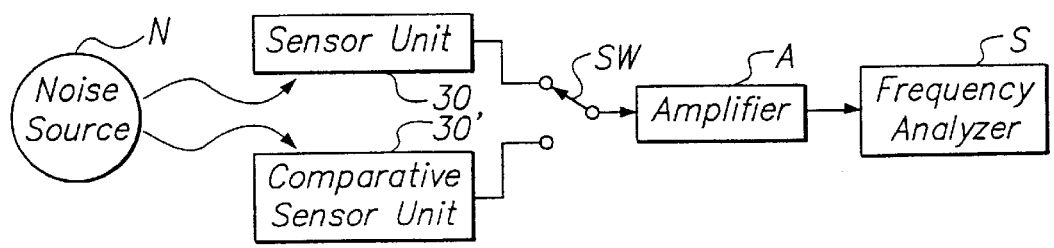
FIG. 12 is a block diagram of a comparison test system.

The present inventors conducted a comparison test using this comparative sensor unit 30' and sensor unit 30. FIG. 12 is a block diagram of the system used for this comparison test. In this comparison test, comparative sensor unit 30' and sensor unit 30 were worn at the base of a finger, and exposed to light emitted from a noise source N at a frequency of 2.2 Hz with a 5000 lux luminance difference as outside light noise. More specifically, noise source N was controlled to switch a 5000 lux light on and off at a 2.2 Hz frequency. The output signals from comparative sensor unit 30' and sensor unit 30 were then switched using switch SW, amplified by an amplifier A with a gain of approximately 6000, and the amplified signals were analyzed by frequency analyzer S.

Figure 13:
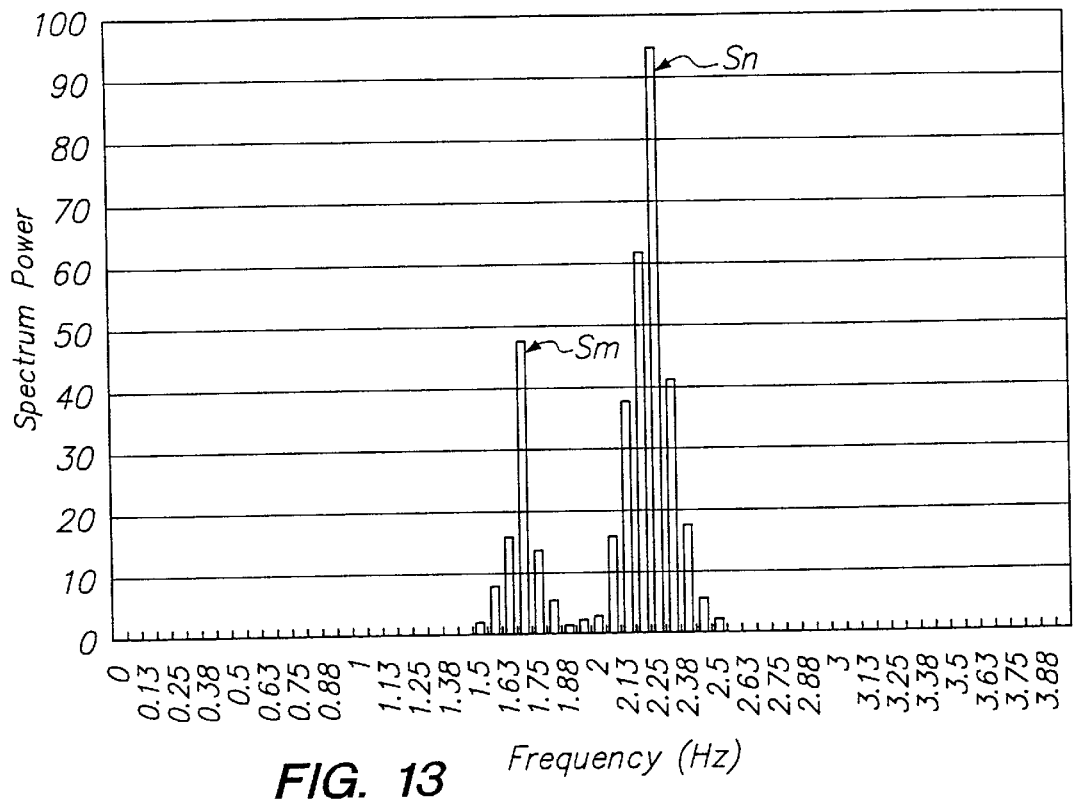
FIG. 13 shows the results of an analysis of the output signal from comparative sensor unit 30'.
Figure 14:
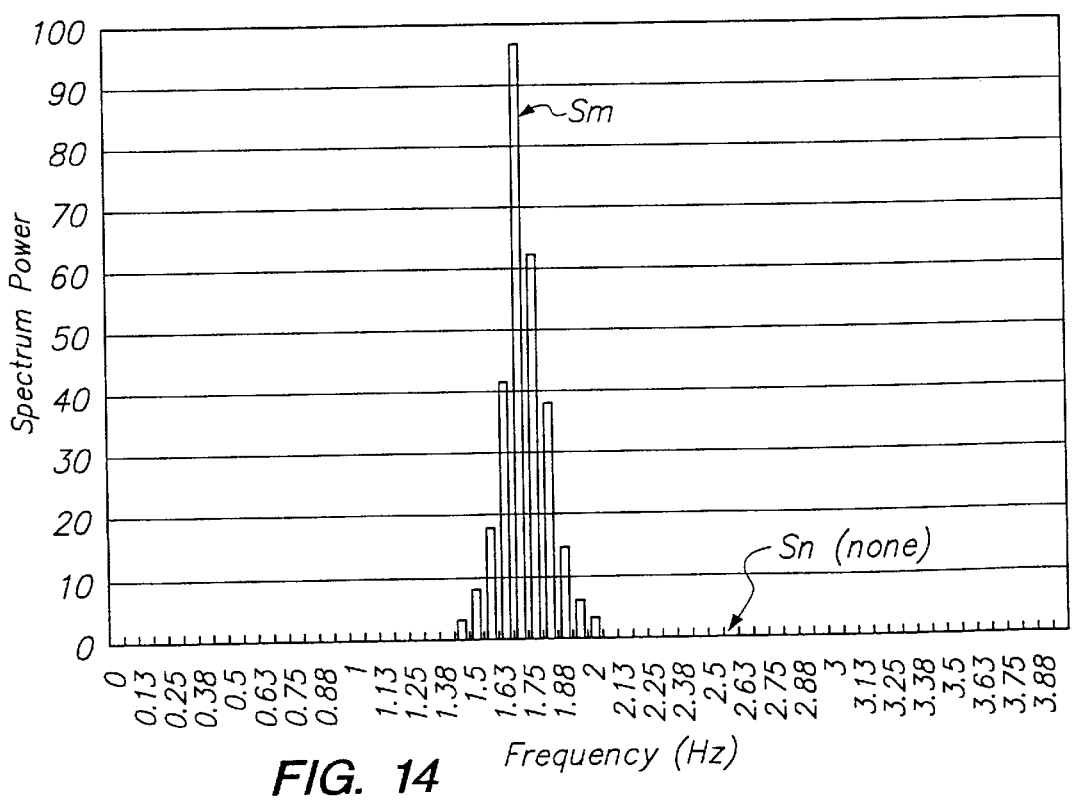
FIG. 14 shows the results of an analysis of the output signal from sensor unit 30.

FIG. 13 shows the results of analysis of the output signal from comparative sensor unit 30', and FIG. 14 shows the results of analysis of the output signal from sensor unit 30. As shown in FIG. 13, the output signal of comparative sensor unit 30' is affected by outside light, and has a noise spectrum Sn near 2.2 Hz. In this example the pulse wave spectrum Sm is at approximately 1.7 Hz. The power of pulse wave spectrum Sm is only half that of noise spectrum Sn. Therefore, if comparative sensor unit 30' is used in pulse wave measuring device 1, noise spectrum Sn will be falsely detected with pulse wave spectrum Sm, and a false pulse rate HR will be calculated.

Compared with this, as shown in FIG. 14, there is no noise spectrum Sn in the output signal of sensor unit 30. Therefore, a pulse wave measuring device 1 using this sensor unit 30 can calculate pulse rate HR based on an accurate pulse wave spectrum Sm.

Figure 15:
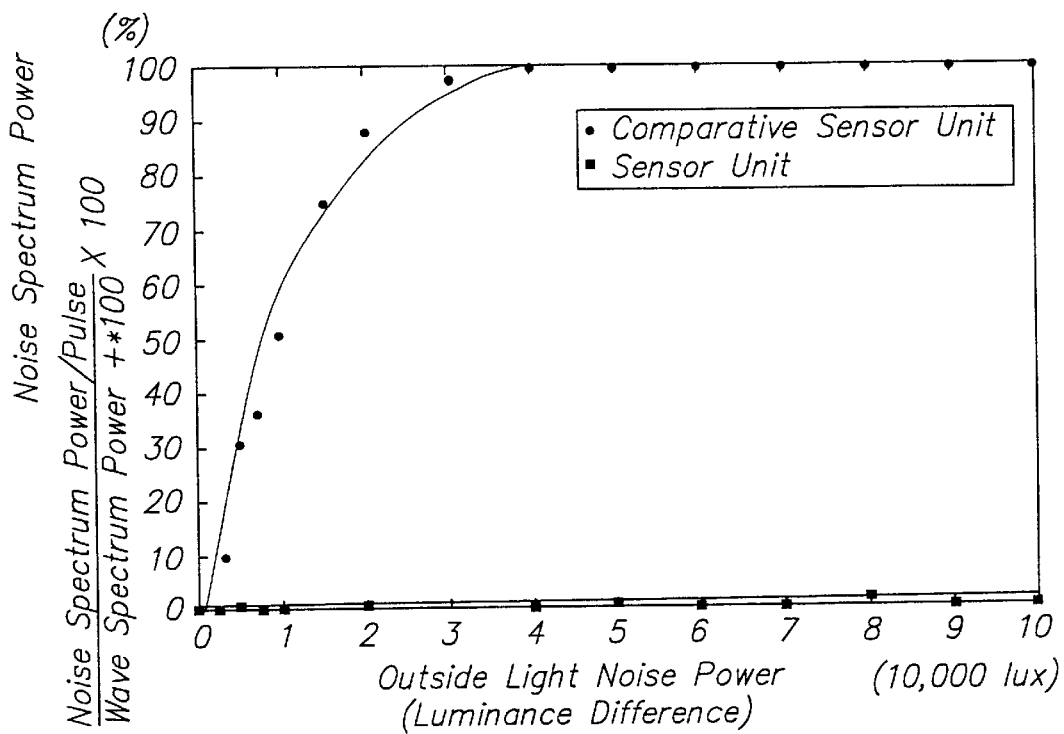
FIG. 15 shows the results of noise spectrum power and pulse wave spectrum power measured for comparative sensor unit 30' and sensor unit 30 when the brightness of the light noise source was varied.

Next, the inventors changed the luminance difference of noise source N for comparative sensor unit 30' and sensor unit 30 to measure the relationship between noise spectrum power and pulse wave spectrum power. FIG. 15 is a graph of the measured results. The vertical axis in this graph is relative power Q (noise spectrum power/pulse wave spectrum power+noise spectrum power), and the horizontal axis is the luminance difference of noise source N. Because the noise component decreases as relative power Q decreases, the pulse wave spectrum Sm can be accurately detected.

As the noise spectrum power increases in the output signal of comparative sensor unit 30', the relative power Q rises, and when noise spectrum power is approximately 8000 lux, the noise spectrum power and pulse wave spectrum power are equal. When noise spectrum power rises to 40,000 lux, relative power is approximately 100%. If the pulse wave spectrum Sm and noise spectrum Sn are differentiated on the basis of spectrum power, comparative sensor unit 30' cannot be used at above approximately 8000 lux.

Compared with this, the output signal of sensor unit 30 is completely unaffected by noise, regardless of the noise spectrum power. This means that even outdoors in midsummer, the pulse wave spectrum Sm can be accurately detected without being affected by outside light.

A-2-2: Operation of the Data Processing Circuit 50

The operation of data processing circuit 50 is described next with reference to the flow chart in FIG. 16. First, the pulse wave signal converter 51 converts pulse wave signal Vm from an analog signal to a digital signal to generate pulse wave data MD (step S1), and body movement signal converter 52 converts body movement signal Vt from an analog signal to a digital signal to generate body movement data TD (step S2). The body movement signal converter 52 stores pulse wave data MD and body movement data TD (step S3).

Figure 17A:
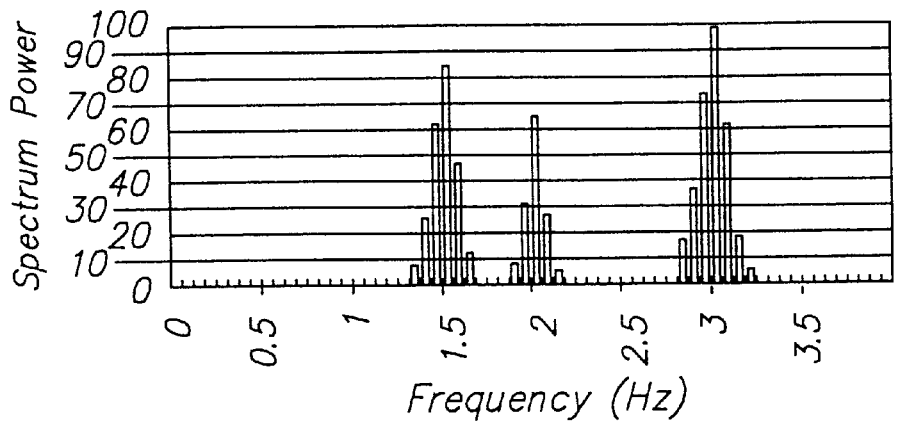
FIG. 17($a$) is an example of pulse wave analysis data MKD, ($b$) of body movement analysis data TKD, and ($c$) of pulse wave analysis data after body movement component removal MKD'.

Next, the pulse wave frequency analyzer 54 applies a fast Fourier transform process to the pulse wave data MD read from memory 53 to generate pulse wave analysis data MKD (step S4). In this case, pulse wave signal Vm is affected by body movement such as swinging the arm or up and down movement of the body, and a body movement component is superposed on the pulse wave analysis data MKD in addition to the true pulse wave component. An example of pulse wave analysis data MKD is shown in FIG. 17(a). The frequency components around 1.5 Hz and 3 Hz in FIG. 17(a) are body movement components.

Figure 17B:
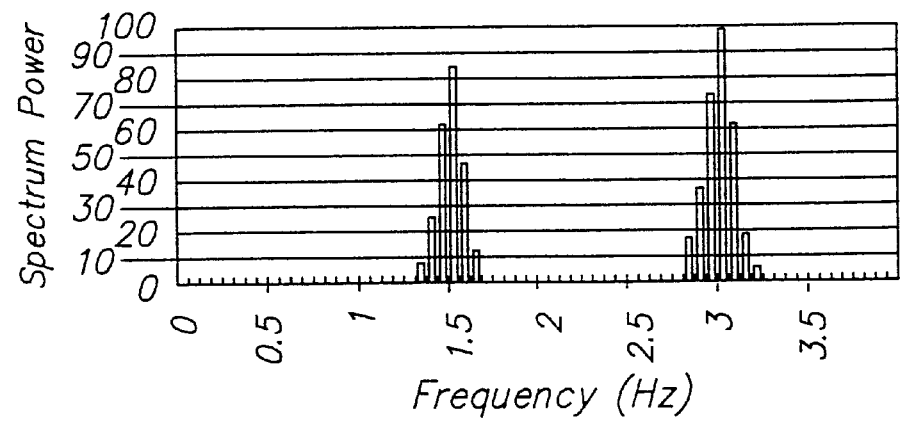

Next, the body movement frequency analyzer 55 applies a fast Fourier transform process to the pulse wave data MD read from memory 53 to generate body movement analysis data TKD (step S5). An example of body movement analysis data TKD is shown in FIG. 17(b). The spectrum frequencies of the body movement analysis data TKD in this case match the spectrum frequencies associated with the body movement component of pulse wave analysis data MKD. It should be noted that while the spectrum frequencies match in this case, they can also differ. This is because while body movement signal TH is detected directly as acceleration caused by, for example, swinging the arm, blood flow is affected by, for example, blood vessels and tissues.

Figure 17C:
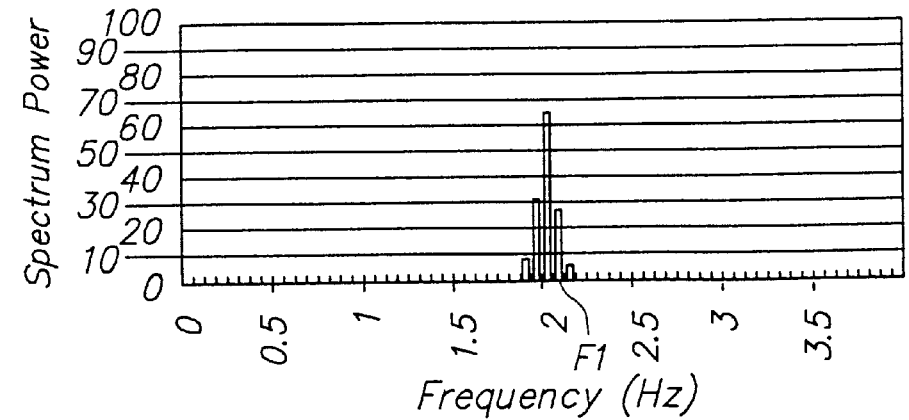

Next, the pulse wave component extractor 56 removes the spectrum frequency components corresponding to each spectrum frequency of body movement analysis data TKD from the spectrum frequency components of pulse wave analysis data MKD to generate the pulse wave analysis data after body movement component removal MKD'. It is therefore possible by means of this process to remove the body movement component from pulse wave analysis data MKD and extract the pulse wave component even if the spectrum power of the body movement component differs in the pulse wave analysis data MKD and body movement analysis data TKD. For example, if the pulse wave analysis data MKD and body movement analysis data TKD are as shown in FIGS. 17(a) and (b), pulse wave analysis data after body movement component removal MKD' will be as shown in FIG. 17(c).

Next, the pulse rate calculator 57 identifies the fundamental frequency Fm1 of the pulse wave component based on pulse wave analysis data after body movement component removal MKD', and calculates 60/Fm1 to generate the pulse rate HR. The fundamental frequency Fm1 of the pulse wave component is obtained by determining the frequency with the greatest spectrum power in the pulse wave analysis data after body movement component removal MKD'. More specifically, spectrum power is compared in sequence to find the greatest. For example, if pulse wave analysis data after body movement component removal MKD' is as shown in FIG. 17(c), F1 is identified as the fundamental frequency Fm1 of the pulse wave component.

In this preferred embodiment of the present invention the effects of outside light can be reliably cancelled using a simple design because the distance between LED 31 and photodiodes 32 and 33 is different and both photodiodes 32 and 33 are placed where outside light is equally incident. As a result, the pulse wave measuring device 1 can be used outside in the middle of summer. Furthermore, the pulse rate HR can be detected even while running or otherwise exercising because the pulse wave signal Vm is frequency analyzed to remove the body movement component. As a result, a user can monitor his or her own health while running, and can thus train more effectively.

A-3. Alternative Version of Embodiment 1

The present invention shall not be limited to the first preferred embodiment described above, and various alternative versions are possible as described below.

(1) In the above-described first embodiment, sensor unit 30 for detecting a pulse wave signal is described as an example of a reflection type photodetection apparatus. The present invention shall not be so limited, however, and insofar as the reflection type photodetection apparatus comprises a light emitting means and photoelectric conversion means, and detects the amount of emitted light from the light emitting means that is reflected by a detected object, it can be used in any way. For example, it can be applied to a device for counting the number of products on the manufacturing line of a manufactured product, or in a device for detecting the presence of paper in a photocopier.

Figure 18:
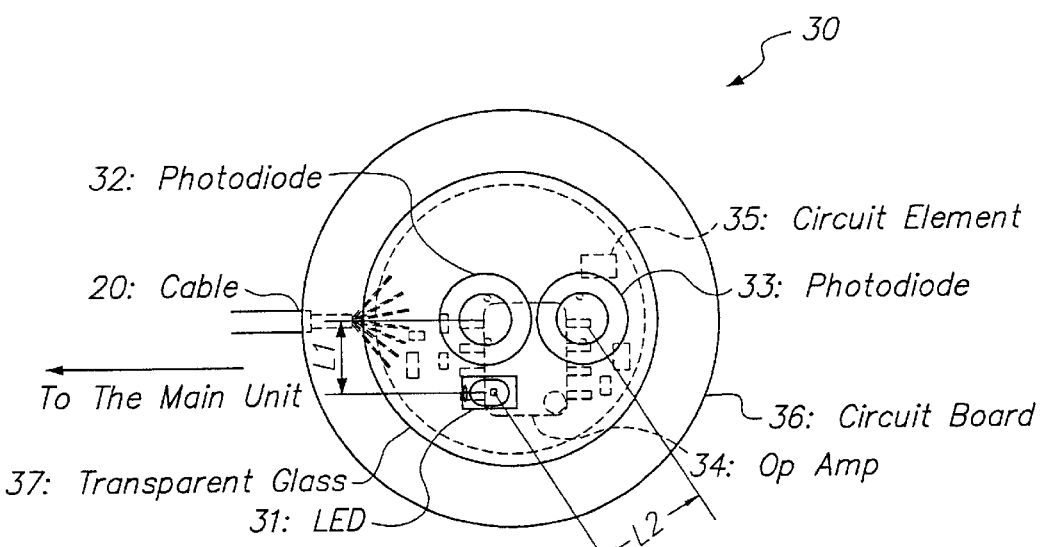
FIG. 18 is a plan view of sensor unit 30 according to an alternative version of the first embodiment.

(2) In the above-described first embodiment, the LED 31 and photodiodes 32 and 33 of sensor unit 30 are arranged in a linear alignment as shown in FIG. 3, but the present invention shall not be so limited. That is, insofar as the distance L1 from LED 31 to photodiode 32 and the distance L2 from LED 31 to photodiode 33 are different, they can be in any desired relative positions. For example, as shown in FIG. 18, the line between LED 31 and photodiode 32 can be perpendicular to the line joining photodiodes 32 and 33.

Figure 19:
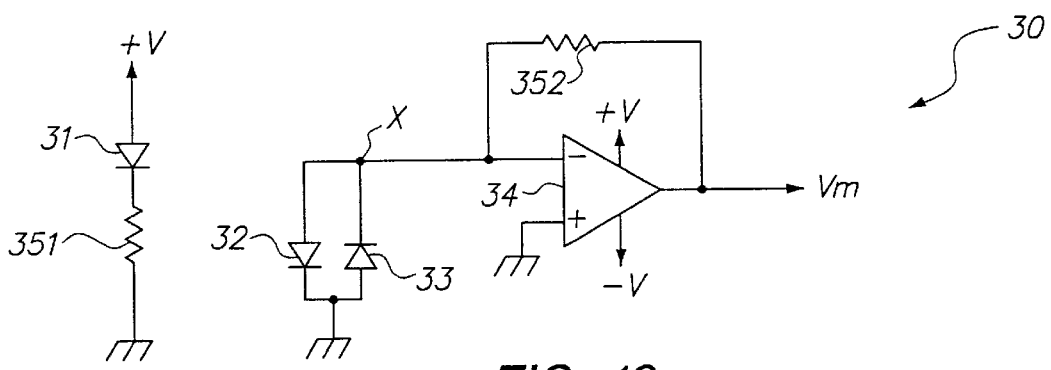
FIG. 19 is a circuit diagram showing the electrical configuration of a sensor unit 30 according to this alternative version of the first embodiment.

(3) The sensor unit 30 in the above-described first embodiment can be configured as shown in FIG. 19. The circuit diagram of sensor unit 30 shown in FIG. 19 differs from that shown in FIG. 5 in that the cathode of photodiode 32 and the anode of photodiode 33 are grounded. In this case, as in the above-described embodiment, current i1 and current i2 are added at node X, and current ic corresponding to outside light luminance Pc can be cancelled.

(4) In the above-described first embodiment, the spectral sensitivity characteristics of photodiodes 32 and 33 are described as being as indicated by the solid line in FIG. 6, but they can alternatively have a peak wavelength of approximately 950 nm as indicated by the dotted line in FIG. 6. It is known that, in general, blood flow within approximately 3 mm from the skin surface can be measured if light having a wavelength of 300 nm to 600 nm is used for the detection light. This is because short wavelength light is easily absorbed or dispersed by body tissues. Good resistance to the effects of outside light can therefore be achieved if the wavelength range of the detection light is from 300 nm to 600 nm because outside light in the 300 nm to 600 nm wavelength range will be absorbed and dispersed by body tissues. However, special devices with the spectral sensitivity limited to this range are expensive. On the other hand, photodiodes exhibiting a spectral sensitivity characteristic as described in the first embodiment above or as indicated by the dotted line in FIG. 6 are low cost and exhibit stable characteristics. Because the effects of outside light can be cancelled in the above-described described first embodiment, the pulse wave signal Vm can be accurately detected using a photodiode exhibiting a spectral sensitivity characteristic as indicated by the solid line or dotted line in FIG. 6 without limiting the wavelength of detected light to 300 nm to 600 nm. In this case, pulsation in various arteries, including the radial artery, can be detected because emitted light reaches inside the tissue.

(5) In the above-described first embodiment, the data processing circuit 50 calculates the pulse rate HR based on analysis data after body movement component removal MKD', but the present invention shall not be so limited. For example, the low frequency component of the analysis data after body movement component removal MKD' can be analyzed to calculate respiration information indicative of the respiration rate. In addition, an inverse fast Fourier transform can be applied to the analysis data after body movement component removal MKD' to detect such pulse phenomena as the normal pulse rate, "slippery pulse", and "wiry pulse"*, based on the result of the analysis. In other words, the data processing circuit 50 can be any type of circuit for generating biological information indicative of a body condition based on analysis data after body movement component removal MKD'.

(6) The above-described first embodiment has been described by way of example using the base of the finger as the detection site for pulse wave signal Vm, but the pulse wave signal Vm can be detected at any part of the skin by appropriately modifying the design of sensor unit 30. For example, other potential detection sites include around the neck, the ear lobe, and the wrist.

B. Embodiment 2

The second embodiment of the present invention relates to a body movement measurement device. A body movement measurement device is used to measure body movement by modifying part of the sensor unit 30 (reflection type photodetection apparatus) in the above-described first embodiment of the invention.

B-1. Principle

The body movement signal detection principle of this preferred embodiment is described next. A body movement measurement device according to this preferred embodiment detects body movement using a reflection type optical sensor (sensor unit 300 described below) comprising a photodetection means and light emitting means.

Figure 20:
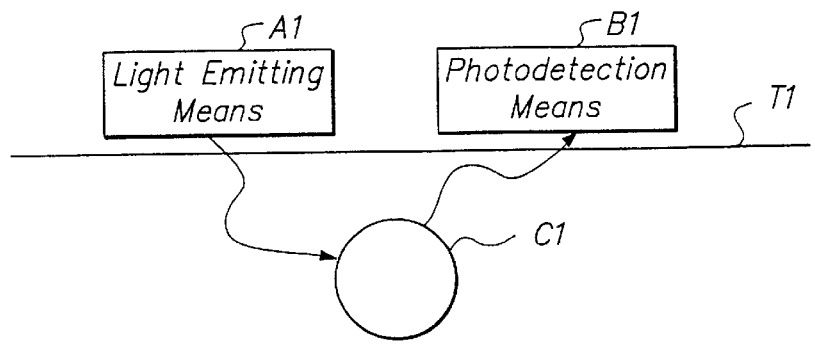
FIG. 20 is used to explain the principle of a reflected light optical sensor according to a second embodiment of the present invention.

FIG. 20 is for describing the principle of the reflection type optical sensor. Shown in the figure are light emitting means A1 and photodetection means B1, epidermis T1, and blood capillaries and arterioles C1. Body tissues are present between the epidermis T1 and blood vessels C1. Blood flows through blood vessels C1.

Part of the light emitted from light emitting means A1 is absorbed by body tissues and hemoglobin in the blood, and another part is reflected by body tissue with the reflected light detected by the photodetection means B1. The photodetection means B1 outputs an output signal corresponding to the amount of detected light. Absorption by body tissues and absorption by hemoglobin in the blood are thus reflected in the output signal of the photodetection means B1.

Figure 21:
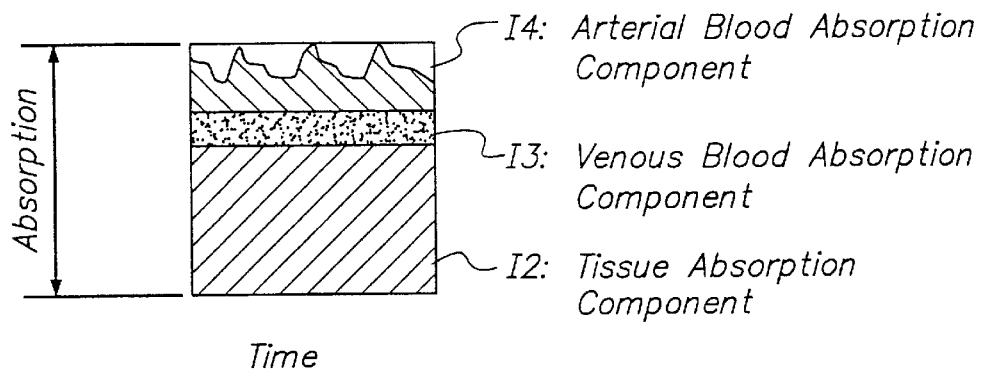
FIG. 21 is a graph showing the distribution of light absorption when the body is in a state of rest with no movement and light is emitted to the blood vessels of the body from an external source.

FIG. 21 shows the absorption distribution when a person's blood vessels are exposed to light from an outside source while at rest with no body movement; I2 indicates the tissue absorption component, I3 the venous blood absorption component, and I4 the arterial blood absorption component.

Figure 22:
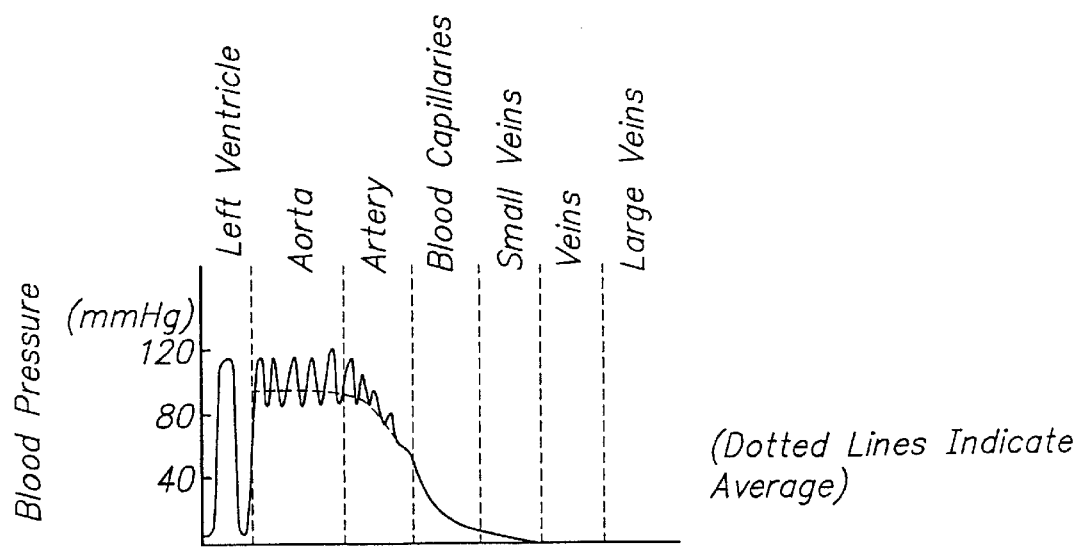
FIG. 22 is a graph showing the change in blood pressure of blood pumped from the heart.

As will be known from the figure, the tissue absorption component I2 is constant because the tissue density does not change. The venous blood absorption component I3 is also constant. This is because there is no pulse in the veins, and there is therefore no change in density. This is shown in FIG. 22, from which it will be known that the pulse of blood pumped from the heart gradually dissipates, and has completely disappeared in the veins.

On the other hand, there is variation in the arterial blood absorption component I4 and venous blood absorption component I3 when the body is moving because body movement affects blood flow. In addition, swinging the hands and arms produces vibration in the tissues, which results in a variation in absorption in the affected parts.

The output signal of the photodetection means B1 cannot, therefore, be used as a body movement signal by simply emitting light to the blood vessels C1 and detecting reflected light therefrom using the photodetection means B1 because there is variation in the arterial blood absorption component I4 regardless of whether there is body movement.

Figure 23:
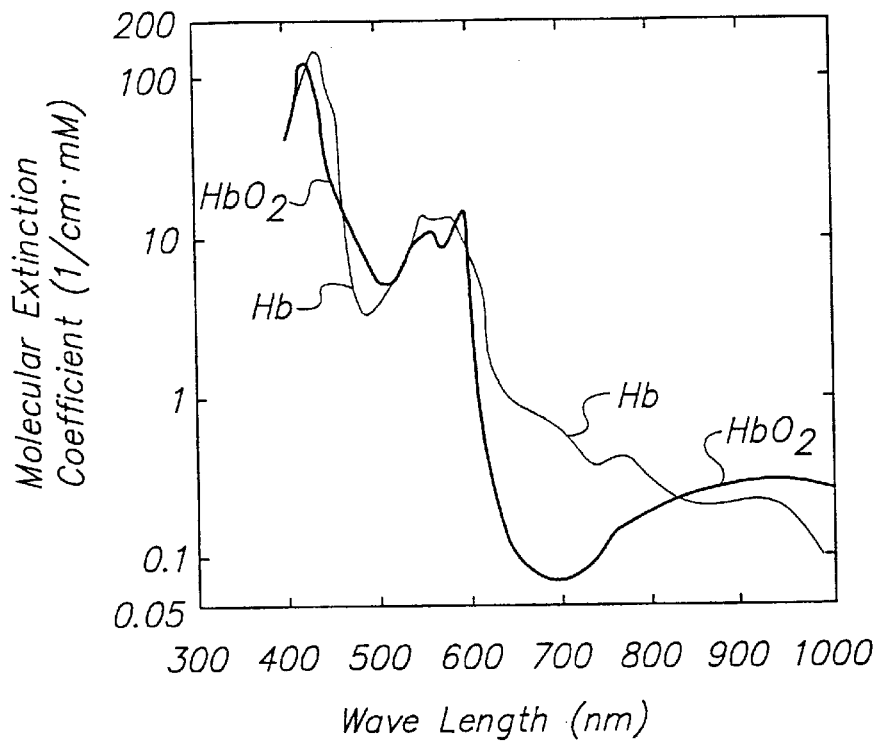
FIG. 23 is a graph of the molecular extinction coefficient of reduced hemoglobin Hb and oxygenated hemoglobin $HbO_2$.

On the other hand, the tissue absorption component I2 and blood absorption components I3 and I4 each have a particular frequency characteristic, and absorption differs according to the wavelength of the emitted light. FIG. 23 shows the molecular extinction coefficient of reduced hemoglobin Hb and oxygenated hemoglobin $HbO_2$. It should be here noted that oxygenated hemoglobin $HbO_2$ is present primarily in arterial blood, and reduced hemoglobin Hb is present in venous blood. It is therefore possible to observe the pulse-related absorption component by considering only absorption by oxygenated hemoglobin $HbO_2$ because there is no pulse in venous blood as noted above. As shown in FIG. 23, the extinction coefficient of oxygenated hemoglobin $HbO_2$ drops sharply above 600 nm. On the other hand, tissue absorption does not drop even above 600 nm.

Therefore, if light is emitted from the light emitting means A1 to the body in the wavelength range above 600 nm, there is substantially no absorption of emitted light by oxygenated hemoglobin $HbO_2$, and the majority of emitted light is absorbed by the tissues. If there is body movement at this time, there will be tissue vibration as noted above, and the amount of emitted light absorbed by tissues will vary according to the body movement. Therefore, if this reflected light is detected by photodetection means B1, the output signal of the photodetection means B1 can be used as a body movement signal. This second preferred embodiment of the present invention focuses on the above-described body movement detection principle to measure movement of the body.

B-2. Configuration of the Second Embodiment

B-2-1: Overall Configuration

The appearance of a body movement measurement device according to this second embodiment is the same as a pulse wave measuring device 1 according to the first embodiment of the invention shown in FIG. 1. However, sensor unit 300 is used in this second embodiment in place of sensor unit 30 in the first embodiment. This sensor unit 300 is comprised to convert reflected light in the wavelength range of 600 nm and above to an electrical signal such that a body movement signal Vt indicative of the amount of body movement is output from sensor unit 300. Therefore, an acceleration detector 60 is not provided inside main body 10. In addition, the data processing circuit 50 provided in the main body 10 applies a fast Fourier transform process to the body movement signal Vt, and analyzes the result of this process to calculate pitch P.

B-2-2: Configuration of the Sensor Unit 300

The mechanical configuration of sensor unit 300 in this second embodiment of the invention is the same as that of the sensor unit 30 in the first embodiment except that LED 310 is used in place of LED 31 (light emitting means). Therefore, the relative positions of the LED 310 and photodiodes 32 and 33 are those resulting from replacing LED 31 in FIG. 3 and FIG. 4 with LED 310.

Figure 24:
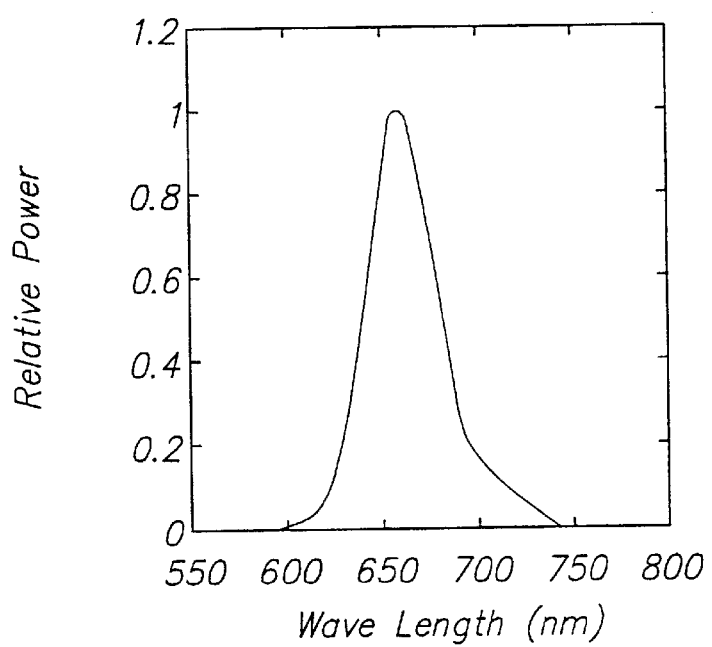
FIG. 24 is a graph of the light emitting characteristic of a LED 310 according to this second embodiment.

The spectral sensitivity characteristics of photodiodes 32 and 33 are as indicated by the solid line in FIG. 6. On the other hand, the light emitting characteristic of the LED 310 is as shown in FIG. 24. Measurement by the sensor unit 300 therefore occurs in the wavelength range where the photodiode characteristics and LED characteristics overlap, that is, in the range 630 nm to 690 nm with a center wavelength of 660 nm. As shown in FIG. 23, absorption by oxygenated hemoglobin $HbO_2$ is reduced in the 630 nm to 690 nm wavelength range. As a result, the pulse wave component is suppressed, and the body movement component accounts for the majority of the output signals of photodiodes 32 and 33.

The LED 310 and photodiodes 32 and 33 are arranged in this embodiment in the same way as in the first embodiment (see FIG. 3 and FIG. 4). As a result, the optical path from LED 310 to photodiode 33 is longer than the path from LED 310 to photodiode 32.

Emitted light from LED 310 is absorbed and dispersed by body tissues, but as the path length increases, substantially all emitted light becomes absorbed by the transmission medium, that is, the body tissues. Therefore, when the path length is long, there is substantially no reflected light incident on photodiodes 32 and 33. As described in the first embodiment above, distance L1 shown in FIG. 3 is determined so that there is relatively little absorption and dispersion by the tissues, and tissue movement can be detected by photodiode 32. In addition, distance L2 shown in the same figure is determined so that there is substantially no reflected light incident on photodiode 33. Therefore, the output signal of photodiode 32 reflects tissue variations due to body movement, but there is no body movement waveform in the output signal of the photodiode 33.

Figure 25:
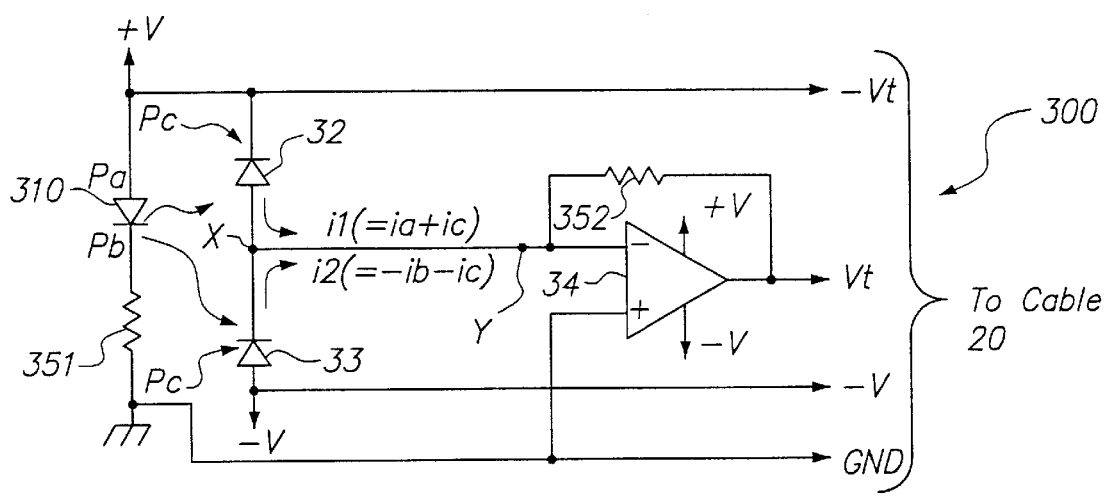
FIG. 25 is a circuit diagram showing the electrical configuration of a sensor unit 300 according to this second embodiment.

FIG. 25 is a circuit diagram of the sensor unit 300. This sensor unit 300 differs from sensor unit 30 shown in FIG. 5 in that LED 31 is replaced by LED 310, and opamp 34 outputs body movement signal Vt.

The photodiodes 32 and 33 are positioned relative to each other so that the luminance (intensity) of outside light thereon is equal as described in the first embodiment. The current ic corresponding to the luminance Pc of outside light is therefore cancelled by the addition of current i1 and current i2 at node X.

In addition, distance L2 from LED 310 to photodiode 33 is determined so that there is substantially no incidence of light from LED 310. As a result, luminance Pb is extremely low relative to luminance Pa. As a result, current i1+i2 can be approximated by the following equation:

$$i1+i2 = ia - ib \; ia$$

Therefore, body movement signal Vt is dependent on the luminance Pa of reflected light incident on photodiode 32.

When a sensor unit 300 thus comprised is held at the base of a finger by sensor holding band 40 as shown in FIG. 1, LED 310 and photodiodes 32 and 33 are held with the light emitting surface and photodetecting surfaces thereof facing the surface of the finger. When the LED 310 then emits light to the finger while thus positioned, light reflected from the body is detected by photodiodes 32 and 33. It should be noted that even if outside light enters from skin that is not covered by the sensor holding band 40 on the finger and is detected, the outside light components are mutually cancelled. It is therefore possible to input only a body movement signal Vt indicative of body movement through cable 20 to main body 10.

B-2-3: Configuration of the Data Processing Circuit 500

The data processing circuit 500 in this second embodiment is described next with reference to FIG. 26. It should be noted that data processing circuit 500 is housed inside main body 10 as in the first embodiment. The data processing circuit 500 also specifically comprises CPU, RAM as working memory for the CPU, and ROM storing a program for achieving the above-noted function blocks.

Figure 26:
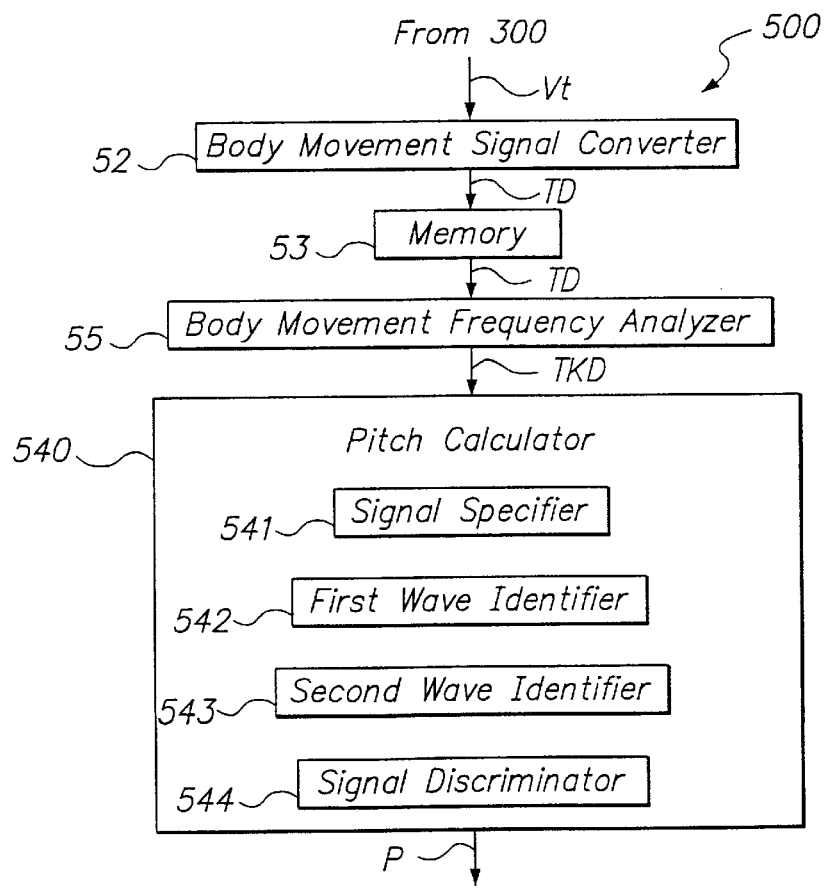
FIG. 26 is a function block diagram of data processing circuit 500 according to this second embodiment.

FIG. 26 is a function block diagram of data processing circuit 500. In the figure, body movement signal converter 52 converts body movement signal Vt from sensor unit 300 from an analog signal to a digital signal, and outputs body movement data TD. Memory 53 is RAM or other memory for storing body movement data TD for a specific period. Body movement frequency analyzer 55 generates body movement analysis data TKD by frequency analyzing body movement data TD read from memory 53. Various methods can be used for this frequency analysis. The present exemplary embodiment uses a fast Fourier transform (FFT) because analysis can be completed in a short operating time.

Next, pitch calculator 540 calculates pitch P based on spectrum power in the body movement analysis data TKD, and outputs the calculated result to the LCD.

This pitch calculator 540 comprises signal identifier 541, first wave identifier 542, second wave identifier 543, and signal discriminator 544.

The signal specifier 541 selects a signal with a power level exceeding a specific threshold in a range above a specific frequency as a reference wave. The first wave identifier 542 determines whether there is a high level signal with a frequency equivalent to ⅓ the reference wave frequency. The second wave identifier 543 determines whether there is a high level signal with a frequency equivalent to ⅔ the reference wave frequency.

If the first wave identifier 542 determines that there is not a high level signal with a frequency equivalent to ⅓ the reference wave frequency, signal discriminator 544 identifies the reference wave as the second harmonic of the fundamental wave of body movement. In addition, if the second wave identifier 543 determines that there is not a high level signal at a frequency position equivalent to ⅔ the reference wave frequency, the signal discriminator 544 identifies the reference wave as the second harmonic of the fundamental wave of body movement.

Furthermore, even when the signal discriminator 544 determines the reference wave to be the third harmonic of the fundamental wave based on the results of first wave identifier 542 and second wave identifier 543, the reference wave is only determined to be the third harmonic of the fundamental wave if the reference wave is determined to equal or exceed a specific frequency level. However, if the reference wave is determined to be below the frequency level of the process, the signal discriminator 544 determines the reference wave to be the second harmonic of the fundamental wave.

A pitch calculator 540 thus comprised automatically determines from the spectrum detected when walking and the spectrum detected when running whether [the user] is walking or running, applies an appropriate operation, and obtains the pitch of body movement.

Figure 27A:
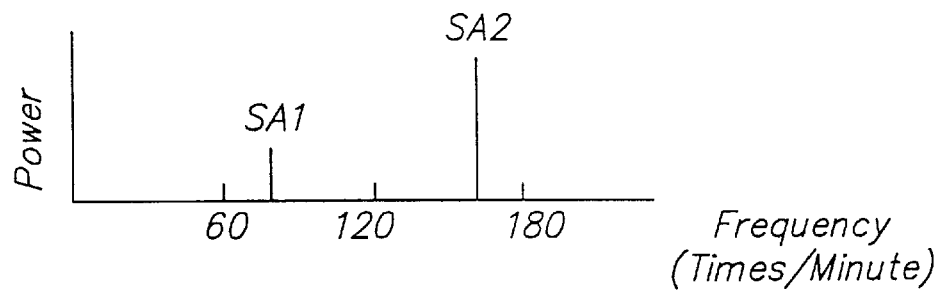
FIG. 27($a$) is a typical example of the body movement signal spectrum when running, and ($b$) is a typical example of the body movement signal spectrum when walking.

The principle for this is described next below. First, FIG. 27(a) is a typical spectrum when the user is running. When running, spectrum line SA1, corresponding to the fundamental wave of body movement, and spectrum line SA2, equivalent to the second harmonic of the fundamental wave of body movement, appear as shown in the figure. Of these, the level of spectrum line SA2 equivalent to the second harmonic component is significantly higher than spectrum line SA1 corresponding to the fundamental wave. This is because when running there is an equal up and down movement when the right foot steps and when the left foot steps, and the second harmonic of the body movement component thus appears. In addition, the fundamental wave of arm swinging (equivalent to SA1) is equivalent to a pendulum action of which the out-swing and return of the arm is one period. However, because it is difficult when running for the swinging of the arms to achieve a smooth pendulum motion, the fundamental wave power of arm swinging is weak. On the other hand, there is a momentary acceleration at the out-swing and the return of the arm, and the second harmonic component is stronger than the fundamental wave component of arm swinging.

Figure 27B:
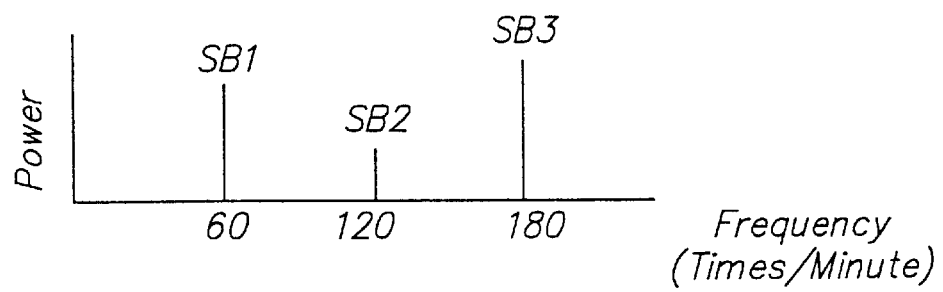

This compares with the typical spectrum when the user is walking as shown in FIG. 27(b). Spectrum line SB1 corresponding to the fundamental wave of body movement, spectrum line SB2 corresponding to the second harmonic, and spectrum line SB3 corresponding to the third harmonic appear when the user is walking. There is not as much up and down movement when walking as there is when running, and the signal component attributable to arm swinging is relatively strong. This characteristic appears in spectrum line SB1 corresponding to the fundamental wave. As a result, the ratio between spectrum lines SB1, SB2, and SB3 is not constant. However, compared with running, the levels of spectrum line SB1 and spectrum line SB3 are higher than the level of spectrum line SB2.

Spectrum line SA2 corresponding to the second harmonic when running, spectrum line SB1 corresponding to the fundamental wave of body movement, spectrum line SB2 corresponding to the second harmonic when walking, and spectrum line SB3 corresponding to the third harmonic when walking normally appear in a frequency range of 100 times/minute or greater. It is therefore possible to determine whether the user is running or walking by monitoring a frequency range of 100 times/minute and above, and determining whether high level signals detected in this range are the second harmonic of the fundamental wave or the third harmonic.

When running, the third harmonic of the fundamental wave in the frequency range of 100 times/minute and above appears as a high level signal, and it is therefore possible to obtain the pitch P when walking from the product of the frequency of this signal multiplied by ⅔. Conversely, the second harmonic of the fundamental wave appears as a high level signal in the frequency range of 100 times/minute and above when running, and the pitch P when running can be obtained from the frequency of this signal. The pitch calculator 540 is thus comprised to use the difference in the spectrum patterns when running and walking to obtain the pitch P.

B-3. Operation of the Second Embodiment

The operation of this preferred embodiment of the present invention is described next with reference to the accompanying figures.

B-3-1: Operation of the Sensor Unit 300

Figure 29:
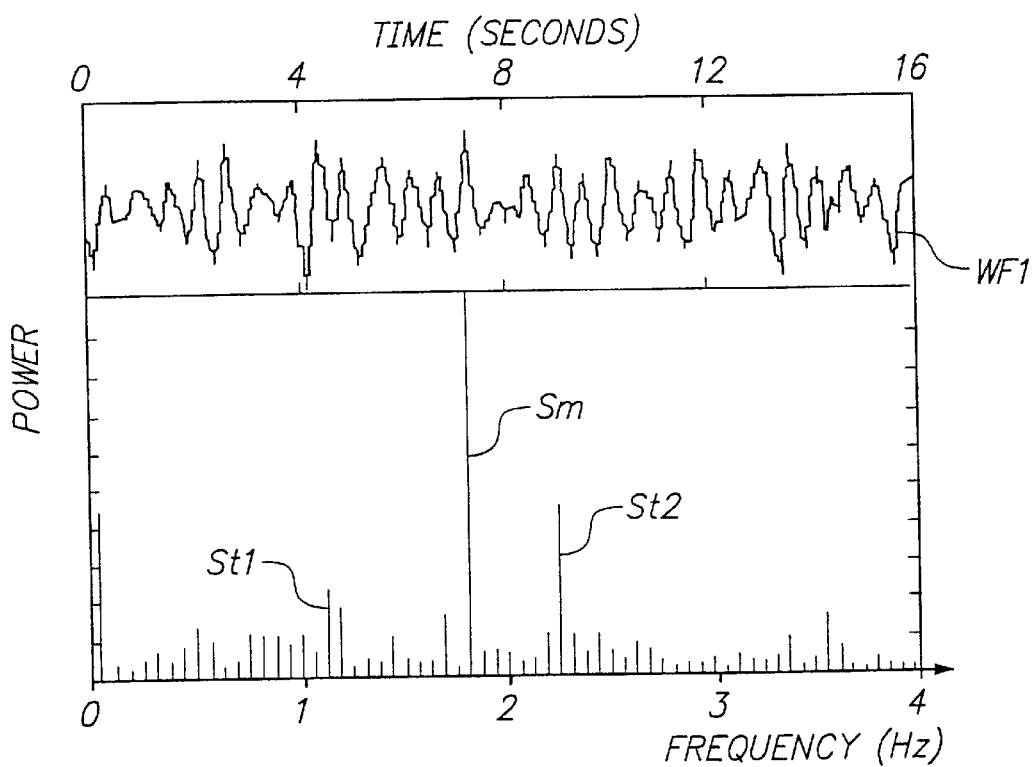
FIG. 29 is a graph showing an example of output signal wave of comparative sensor unit 300' and the result of frequency analysis applied thereto.

The operation of sensor unit 300 is first described in comparison with the operation of a comparative sensor unit. In this comparative sensor unit 300', the LED 31 having light emitting characteristics as shown in FIG. 24 was replaced with LED 310' having light emitting characteristics as shown in FIG. 29. The light emitting characteristic of LED 310' has a peak wavelength at 525 nm with a peak width at half height of approximately 40 nm. That is, comparative sensor unit 300' obtains measurements in a wavelength range where the absorption characteristic of oxygenated hemoglobin $HbO_2$ is great. (See FIG. 23.)

Figure 28:
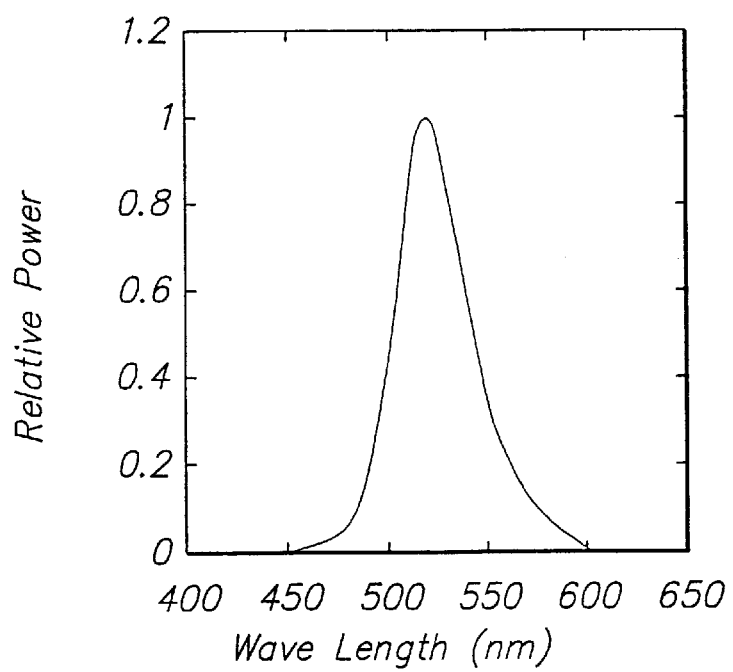
FIG. 28 is a graph of the light emitting characteristic of an LED 310' used in a comparative sensor unit 300'.

FIG. 28 is a graph of an output signal wave WF1 from comparative sensor unit 300' and the frequency analysis thereof. In this figure, St1 is the spectrum line corresponding to the fundamental wave of the body movement component, and has a frequency of 1.1 Hz. St2 is the spectrum line corresponding to the second harmonic of the body movement component, and has a frequency of 2.2 Hz. Sm is the spectrum line corresponding to fundamental wave of the pulse wave component. As will be known from this figure, if the wavelength range used for measurements is set below 600 nm, emitted light is absorbed by oxygenated hemoglobin $HbO_2$ and the pulse of arterial blood is measured as spectrum line Sm. Because the power of pulse wave spectrum Sm is greater than spectrum lines St1 and St2 related to the body movement component, the fundamental wave of body movement is falsely detected, and an accurate pitch P therefore cannot be detected.

Figure 30:
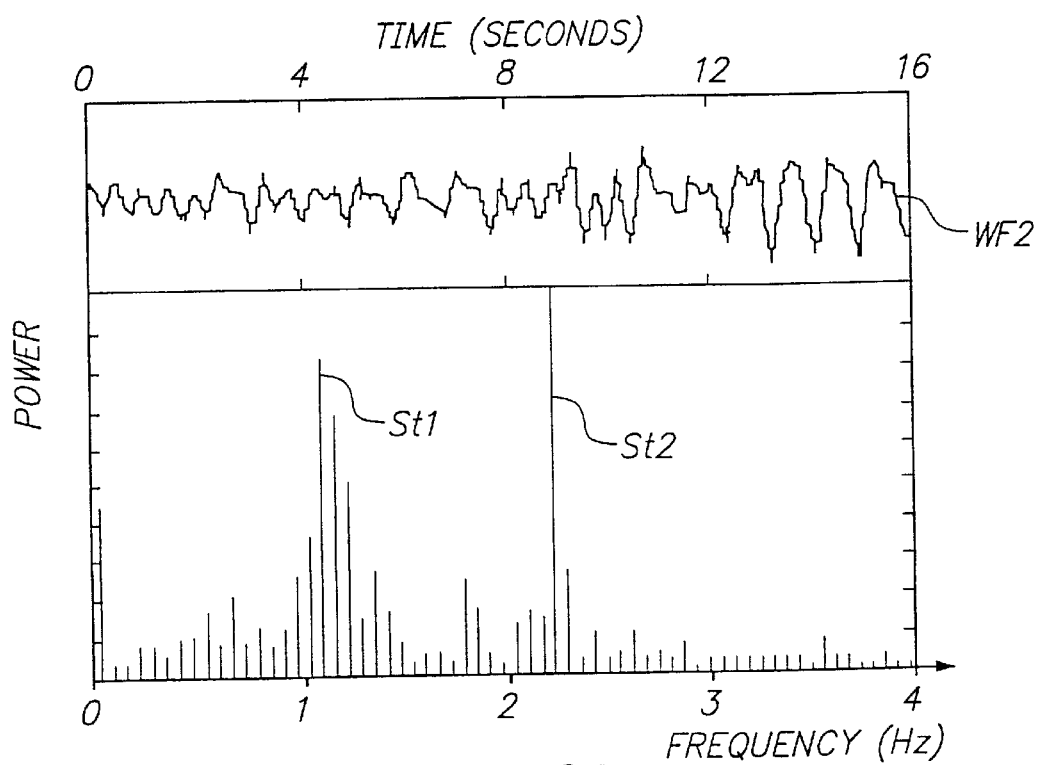
FIG. 30 is a graph showing an example of output signal wave of sensor unit 300 and the result of frequency analysis applied thereto.

This can be compared with the output signal wave WF2 of sensor unit 300 and the frequency analysis thereof as shown in FIG. 30. The LED 310 used in this example has a light emitting characteristic with a peak wavelength at 660 nm and a peak width at half height of 40 nm as shown in FIG. 24. By thus setting the wavelength range used for measurements at 600 nm and above, there is substantially no absorption of emitted light by oxygenated hemoglobin $HbO_2$, and the power of the pulse wave spectrum Sm is greatly reduced. As a result, the power of spectrum lines St1 and St2 related to the body movement component is greater than pulse wave spectrum Sm, Sm is not falsely detected as a body movement component, and the body movement component can be accurately measured.

In addition, because the sensor unit 300 is thus comprised to cancel the effects of outside light, the body movement signal Vt can be detected with a high S/N ratio even when used running or otherwise exercising outdoors.

B-3-2: Operation of the Data Processing Circuit 500

Next, when the body movement signal Vt has been detected by sensor unit 30, the body movement signal converter 52 of the data processing circuit 500 converts the body movement signal Vt from an analog signal to a digital signal to generate body movement data TD. This body movement data TD is stored to the memory 53, and is read from the memory 53 at a specific timing. Then, the body movement frequency analyzer 55 applies a FFT process to the body movement data TD read from memory 53 to generate body movement analysis data TKD. The pitch calculator 540 then calculates pitch P based on the spectra in body movement analysis data TKD.

The pitch calculation process of pitch calculator 540 is described next below with reference to the flow chart in FIG. 31. First, at step ST1, the signal with the highest level (line spectrum) is determined in the body movement analysis data TKD after frequency analysis. This signal is a candidate for the signal to be used as the reference wave for obtaining the pitch. At step ST2, it is determined whether the frequency of this reference wave is 100 times/minute or greater.

If the frequency of the reference wave is less than 100 times/minute, a different candidate is selected in step ST3. Then, in step ST4, the signal with the highest level is selected from the other signals not including the previous [candidate] signal as the reference wave. In this process, the pitch is used as is as the current pitch (step ST5), and in step ST6 this value is defined as the pitch.

If a high level signal with a frequency of 100 times/minute or greater is found while steps ST3 and ST4 are being processed, that signal is used as the reference wave. In step ST7, it is determined whether there is a signal with a frequency ⅓ the frequency of this reference wave and an amplitude at least ½ the amplitude of the reference wave.

If in step ST7 there is not a signal with a frequency ⅓ the frequency of this reference wave and an amplitude at least ½ the amplitude of the reference wave, the procedure advances to step ST8. At step ST8 it is determined whether there is a signal with a frequency ⅔ the frequency of this reference wave and an amplitude at least ½ the amplitude of the reference wave.

If in step ST8 there is not a signal with a frequency ⅓ the frequency of this reference wave and an amplitude at least ½ the amplitude of the reference wave, the reference wave is determined to be a signal equivalent to the second harmonic. This value is then defined as the pitch in step ST6.

However, if in step ST7 there is a signal with a frequency ⅓ the frequency of this reference wave and an amplitude at least ½ the amplitude of the reference wave, the procedure advances to step ST9. In step ST9 it is determined whether the frequency of this reference wave is 150 times/minute or greater. This value of 150 times/minute is 1.5 times 100 times/minute. The pitch while walking is normally in the range from 100 times/minute to 150 times/minute, and the pitch while running is 150 times/minute to 200 times/minute. It is therefore possible to use the value of 150 times/minute as the dividing line for confirming whether the user is walking or running. If it is determined in step ST9 that the frequency of the reference wave is 150 times/minute or greater, the reference wave is determined to be equivalent to the third harmonic. As a result, in step ST10, the frequency of this signal is multiplied by ⅔, and the resulting ⅔ value is confirmed as the pitch in step ST6.

If in step ST7 there is not a signal with a frequency ⅓ the frequency of this reference wave and an amplitude at least ½ the amplitude of the reference wave, the procedure advances to step ST8. If in step ST8 there is a signal with a frequency ⅔ the frequency of this reference wave and an amplitude at least ½ the amplitude of the reference wave, the procedure advances to step ST9. If in step ST9 it is determined that the frequency of this reference wave is 150 times/minute or greater, this reference wave can be confirmed to be the third harmonic of the fundamental wave when walking. Furthermore, because the reference wave can be confirmed to be a signal equivalent to the third harmonic, the frequency of this signal is multiplied by $2/3$ in step ST10, and the resulting $2/3$ value is confirmed as the pitch in step ST6.

However, if in step ST9 the frequency of the reference wave is less than 150 times/minute, the reference wave can be determined as not a signal equivalent to the third harmonic. Therefore, any signal with a frequency that is $1/3$ or $2/3$ the frequency of this reference wave can be determined to be noise, and the reference wave can be determined to be the second harmonic component. Therefore, this value is defined as the pitch at step ST6.

As thus described, if there is not a signal with an amplitude $1/2$ the amplitude of the reference wave at a frequency position equivalent to $1/3$ the frequency of the reference wave, and there is not a signal with an amplitude $1/2$ the amplitude of the reference wave at a frequency position equivalent to $2/3$ the frequency of the reference wave, the reference wave can be determined to be the second harmonic.

Furthermore, if there is a signal with an amplitude $1/2$ the amplitude of the reference wave at a frequency position equivalent to $1/3$ the frequency of the reference wave, or there is a signal with an amplitude $1/2$ the amplitude of the reference wave at a frequency position equivalent to $2/3$ the frequency of the reference wave, the reference wave can only be determined to be the third harmonic if the frequency of the reference wave is 150 times/minute or greater.

As described above, this second embodiment of the present invention uses an optical sensor to measure body movement signal Vt by focusing on the idea that there is tissue vibration when there is body movement, and there is a corresponding change in absorption characteristics. Device reliability can therefore be improved compared with using a mechanical acceleration detector, and the design can be simplified. Furthermore, because tissues vibrate regardless of the direction in which the body moves, a sensor unit 300 according to this preferred embodiment detects overall body movement. Body movement can therefore be reliably detected using a single sensor unit 300, and it is not necessary to provide a device in each axis of detection as it is with an acceleration detector.

Furthermore, because the wavelength range used for measuring the body movement signal Vt is set to 600 nm or above in sensor unit 300, pulse components in the detection signal can be sufficiently suppressed, and body movement signal Vt can be detected with a good S/N ratio. Moreover, because the effects of outside light are cancelled by the two photodiodes 32 and 33, an accurate body movement signal Vt can be detected even while exercising outdoors.

B-4. Alternative Versions of the Second Embodiment (1) Body movement is detected at the base of a finger in the second preferred embodiment of the present invention described above, but as described in the following third preferred embodiment it is also possible to house the sensor unit 300 on the bottom side of the watch case 11 to detect the body movement signal Vt from the back of the wrist. In addition, photodiode 33 can be removed from the sensor unit 300 as shown in FIG. 25. Outside light cannot be cancelled in this case, but because the wavelength range used for measurement is set to 600 nm, a body movement signal Vt without a superposed pulse wave component can be obtained.

(2) In addition, measurement is possible in the wavelength range of 600 nm and above in the above second preferred embodiment by setting the light emitting characteristic of the LED 310, the light emitting means, with a wavelength peak of 600 nm or greater, and setting the spectral sensitivity characteristic of the photodiode 32, the photodetection means, in a range from 400 nm to 800 nm. However, the present invention shall not be so limited, and, for example, the emitted light from the light emitting means can be set to have energy in the wavelength range from 400 nm to 800 nm, and the photodetection means to have a spectral sensitivity characteristic of 600 nm or greater. In other words, it is sufficient for the wavelength range used for measurement to be at least 600 nm.

Furthermore, as will be known from FIG. 23, the extinction coefficient of oxygenated hemoglobin $HbO_2$ decreases particularly from 600 nm to 900 nm. Therefore, it is particularly desirable for the wavelength range used for measurement to be set in the range from 600 nm to 900 nm. It should be noted that the wavelength range used for measurement can also be limited by using a filter.

C. Embodiment 3

A biological information measuring apparatus according to a third preferred embodiment of the present invention is described next with reference to the accompanying figures. This biological information measuring apparatus measures the pulse and other biological information based on a pulse wave signal from which body movement has been removed.

C-1. Configuration of the Third Embodiment

C-1-1: Overall Configuration

Figure 32:
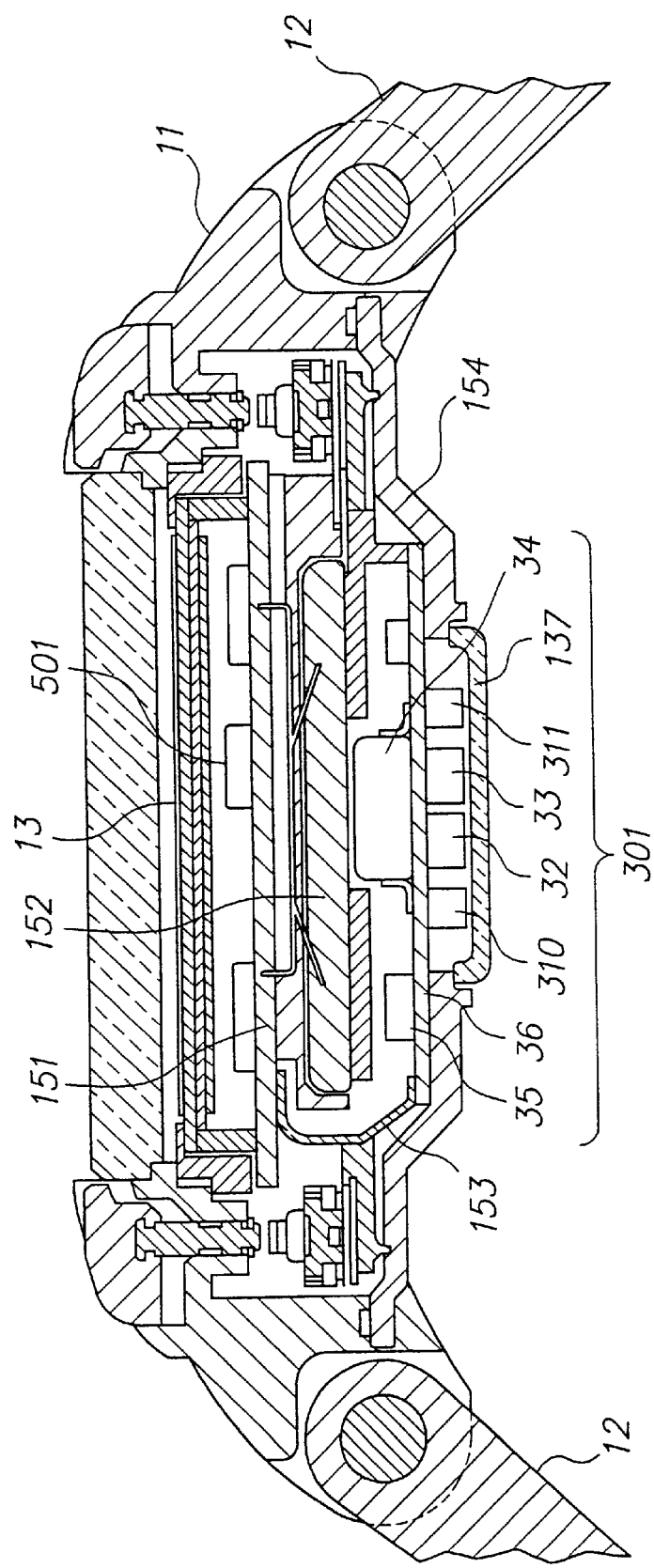
FIG. 32 is a section view of a biological information measuring apparatus according to a third embodiment of the present invention.

FIG. 32 is a section view of a biological information measuring apparatus according to a third embodiment of the present invention. As shown in the figure this biological information measuring apparatus has a wristwatch design. In this exemplary embodiment, sensor unit 301 corresponding to sensor unit 30 in the first embodiment is formed integrally with the main body on the back side of watch case 11. A wristband 12 is attached to the watch case 11 for holding it on the arm; when the wristband 12 is wrapped around the wrist, the back side of the watch case 11 is held tight to the back of the wrist. Transparent glass 137 held by back cover 154 is disposed on the back side of watch case 11. This transparent glass 137 protects sensor unit 301. In addition, transparent glass 137 passes emitted light from LEDs 310 and 311, and passes light reflected through the body.

The surface of the watch case 11 has a liquid crystal display 13 for displaying, in addition to the current time and date, biological information such as the pulse rate HR based on a detection result from the sensor unit 301. Inside the watch case 11 is a data processing circuit 501 comprising various ICs, including a CPU, on a main circuit board 151. A battery 152 is provided on the back side of the main circuit board 151; power is supplied from the battery 152 to the liquid crystal display 13, main circuit board 151, and sensor unit 301. The main circuit board 151 and sensor unit 301 are connected by a heat seal 153. Wiring formed in the heat seal 153 carries power from the main circuit board 151 to the sensor unit 301, and carries a pulse wave signal Vm from sensor unit 301 to main circuit board 151. The data processing circuit 501 applies a FFT process to the pulse wave signal Vm, and analyzes the result of this process to calculate the pulse rate HR. Note that buttons 111 and 112 (not shown in the figure) are also provided on the outside of the watch case 11 for setting the time, changing the display mode, and other operations as in the pulse wave measuring device shown in FIG. 1.

When the wristband 12 is wrapped around the wrist to hold the biological information measuring apparatus, the back side of the watch case 11 faces the back of the wrist.

As a result, light from LEDs 310 and 311 is emitted through the transparent glass 137 to the back of the wrist, and reflected light therefrom is detected by photodiodes 32 and 33.

C-1-2: Configuration of the Sensor Unit 301

The configuration of the sensor unit 30 (reflection type photodetection apparatus) is described next with reference to the following two versions.

C-1-2-1: First Version

Figure 33:
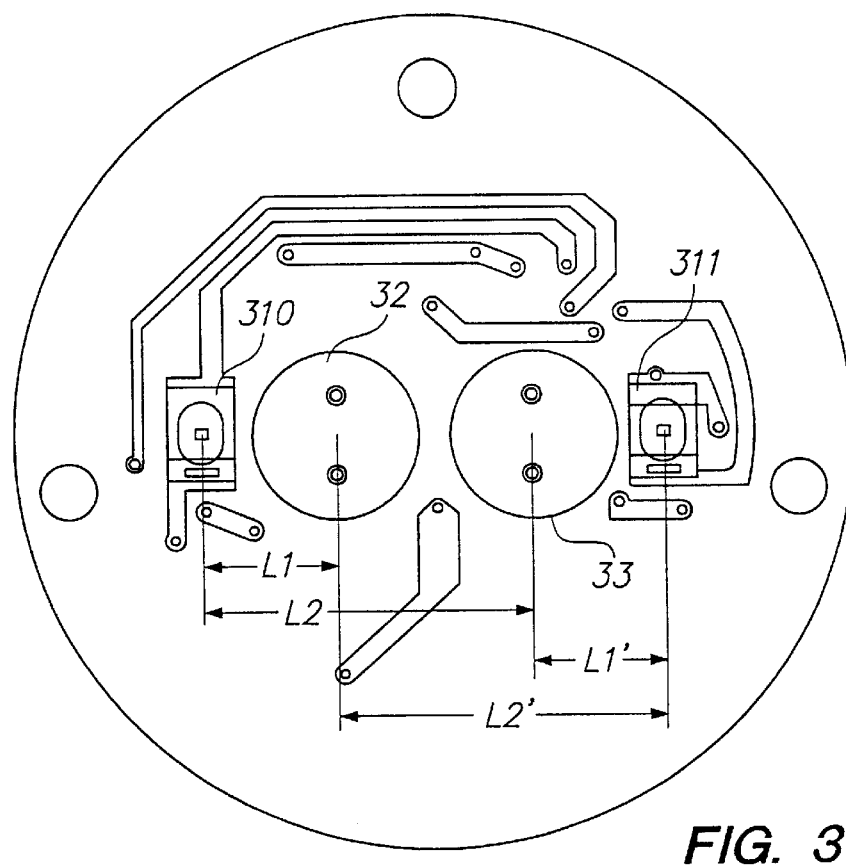
FIG. 33 is a plan view of the back of sensor unit 301 according to a first version of this third embodiment.

FIG. 33 is a plan view from the back of the sensor unit 301. As shown in FIG. 33, LEDs 310 and 311 and photodiodes 32 and 33 are disposed on the back side of circuit board 36, on the top side of which are opamp 34 and circuit element 35 (see FIG. 32). The opamp 34 and circuit element 35 function as a difference operator for amplifying the difference between the output signals from photodiodes 32 and 33. This is described further below.

The spectral sensitivity characteristics of the photodiodes 32 and 33 in this exemplary embodiment are the same as those of the first and second embodiments as shown in FIG. 6. The light emitting characteristic of LED 310 is the same as in the second embodiment as shown in FIG. 24. The light emitting characteristic of LED 311 is as shown in FIG. 28. That is, LED 311 has a light emitting characteristic with a peak wavelength at 660 nm with a peak width at half height of 40 nm, and LED 311 has a light emitting characteristic with a peak wavelength at 525 nm with a peak width at half height of 40 nm. It should be noted that in the wavelength range of 600 nm and above there is substantially no absorption of emitted light by oxygenated hemoglobin $HbO_2$, and the extinction coefficient of oxygenated hemoglobin $HbO_2$ increases in the wavelength range below 600 nm. The change in the oxygenated hemoglobin $HbO_2$ absorption characteristic also corresponds to a pulse wave because oxygenated hemoglobin $HbO_2$ moves according to pulsations in the blood flow. On the other hand, although tissue vibration accompanies movement of the body, there is not a sharp drop in the tissue absorption characteristic in the wavelength range 600 nm and above as there is with oxygenated hemoglobin $HbO_2$. As a result, LED 310, which emits light with a wavelength of 600 nm or above, is used as the light emitting means for body movement detection, and LED 311, which emits light with a wavelength below 600 nm, is used as the light emitting means for blood flow detection.

In addition, in this exemplary embodiment, LEDs 310 and 311 and photodiodes 32 and 33 are arranged in a line as shown in FIG. 33. In this example, distance L1 is the distance from the light emitting center of LED 310 to the photodetection center of photodiode 32; distance L2 is the distance from the light emitting center of LED 310 to the photodetection center of photodiode 33; L1' is the distance from the light emitting center of LED 311 to the photodetection center of photodiode 33; and L2' is the distance from the light emitting center of LED 311 to the photodetection center of photodiode 32. The LEDs 310 and 311 and photodiodes 32 and 33 are arranged so that L1<L2, and L1'<L2'.

That is, photodiode 33 is placed so that the distance L2 from the photodetection center thereof to the light emitting center of LED 310 is different from distance L1 from the light emitting center of LED 310 to the photodetection center of photodiode 32, and so that Li1 is different from L2'. As a result, the path length from LED 310 to photodiode 33 is longer than the path length from LED 310 to photodiode 32. In addition, the path length from LED 311 to photodiode 32 is longer than the path length from LED 311 to photodiode 33.

Emitted light from LED 311 is absorbed and dispersed by body tissues in the same manner as emitted light from LED 310, but because the path length is slightly longer, substantially all of the emitted light is absorbed by the transmission medium, that is, body tissue, and there is no reflected light incident on photodiodes 32 and 33. In this example distance L1' is determined so that there is relatively little tissue absorption and dispersion, and pulse wave detection by photodiode 33 is possible, and distance L2' is determined so that substantially no reflected light is incident on photodiode 32. Therefore, reflected light indicative of tissue variations on outside light and body movement is incident on photodiode 32, and reflected light indicative of outside light and blood flow is incident on photodiode 33. When there is body movement, blood flow is restricted by tissues and blood vessels, and changes accordingly. In other words, the change in the amount of reflected light incident on photodiode 33 has a body movement component superposed on the pulse wave component.

In the following description is it assumed that: Pc is the amount of outside light incident on photodiode 33, Pm is the amount of outside light corresponding to the pulse wave component of the reflected light, and Pt' is the amount of outside light corresponding to body movement; and Pc is the luminance of outside light incident on photodiode 32, and Pt is the luminance of reflected light (that is, luminance corresponding to body movement). It should be noted that Pc is used for the amount of outside light incident on both photodiodes 32 and 33 because the luminance of outside light passing through tissue is the same on photodiodes 32 and 33 because they are placed close together.

Figure 34:
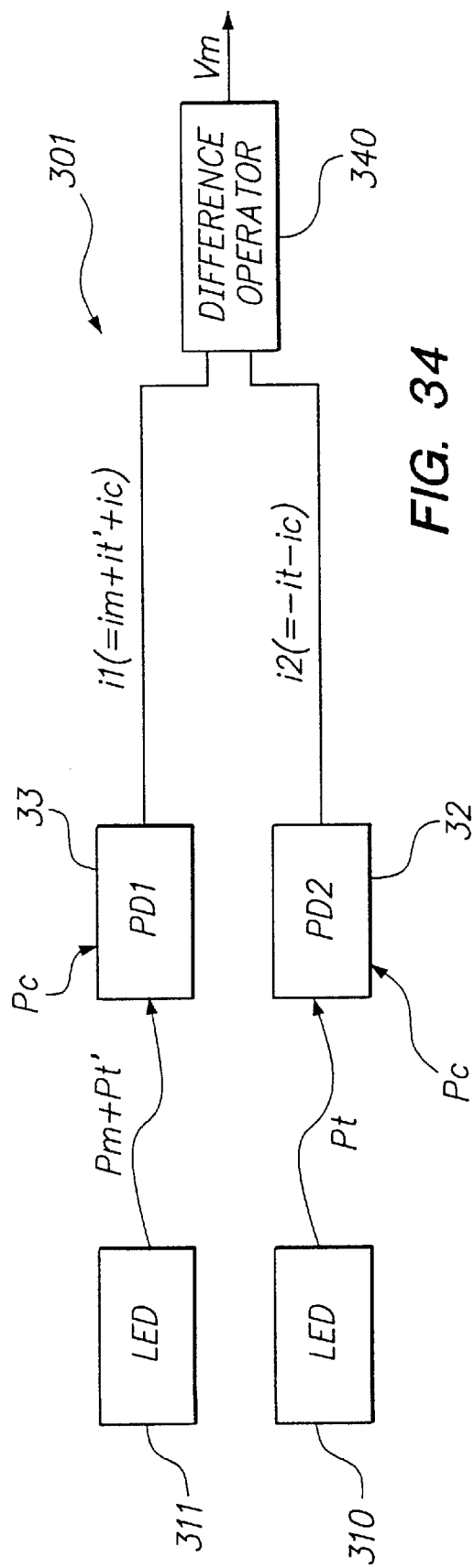
FIG. 34 is a block diagram showing the electrical configuration of sensor unit 301 according to a first version of this third embodiment.
Figure 35:
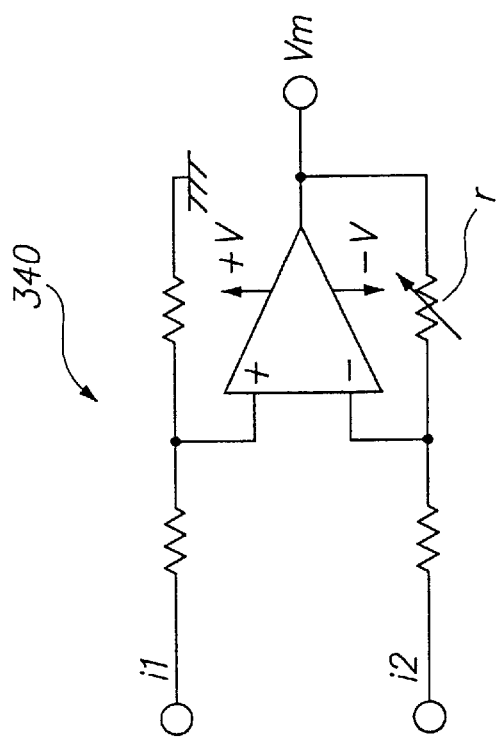
FIG. 35 is a circuit diagram of an exemplary difference operator 340 according to this preferred embodiment.

FIG. 34 is a block diagram showing the electrical configuration of sensor unit 300. As shown in the figure, current i1 flows to photodiode 33, and current i2 flows to photodiode 32. The difference operator 340 subtracts current i2 from current i1, and outputs a voltage corresponding to this difference as pulse wave signal Vm. It should be noted that difference operator 340 can be achieved as a differential amplifier using an opamp and resistance (circuit element) as shown in FIG. 35, for example.

It is further assumed that im, it, it', and ic are the currents corresponding to luminance Pm, Pt, Pt', and Pc. In this case, currents i1 and i2 shown in FIG. 34 can be calculated from the following equations.

$$i1=im+it'+ic$$

$$i2=it+ic$$

Therefore, pulse wave signal Vm output from difference operator 340 is obtained by the following equation where k is the current voltage conversion gain.

$$Vm=k(i1-i2)=k(im+it'-it)$$

That is, currents ic and −ic corresponding to the luminance Pc of outside light are mutually cancelling. In addition, the current corresponding to the body movement component is (it'−it), the body movement component in the blood flow and the body movement component in tissue are mutually cancelling, and (it'−it) is extremely low compared with im. Therefore, pulse wave signal Vm can be approximated by the following equation.

$$Vm=k(im+it'-it)k*im$$

As a result, the output signal of difference operator 340 can be used as a pulse wave signal Vm from which body movement has been removed.

It should be noted that the difference operator 340 is achieved by means of a differential amplifier as shown in FIG. 35. Alternatively, however, an amplifier can be provided after each of the photodiodes 32 and 33 to amplify the output signals from the photodiodes 32 and 33, after which the amplified output signals are passed through an AD converter and converted to digital signals, the difference between which is then calculated by a CPU or other digital signal processing circuit. Pulse wave data corresponding to pulse wave signal Vm can be obtained in this case, too, because a difference operation is applied to digital signals corresponding to currents i1 and i2. It is also possible to effectively suppress the body movement component and increase the S/N ratio of the pulse wave data by digitally adjusting the gain of the digital signals.

C-1-2-2: Second Version

The mechanical configuration of a sensor unit 301 according to this second version is identical to that shown in FIG. 33, and in this exemplary embodiment, too, distances L1, L2 and L1' and L2' are set so that the effects of outside light are cancelled.

Figure 36:
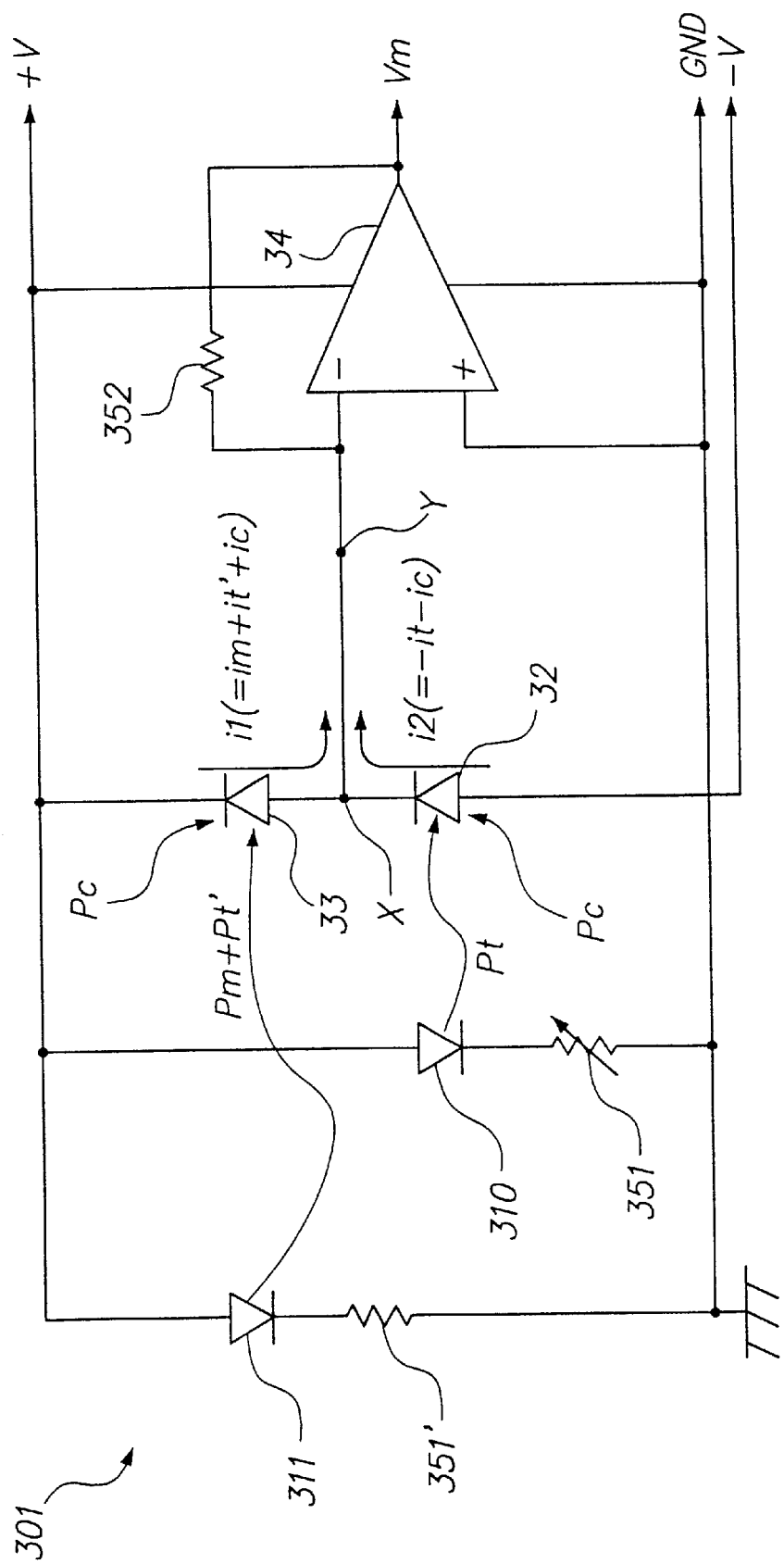
FIG. 36 is a circuit diagram of sensor unit 301 according to a second version of this third embodiment.

FIG. 36 is a circuit diagram of a sensor unit 301 according to this second version. The sensor unit 301 in this figure differs from the sensor unit 300 shown in FIG. 25 in that LED 311 and resistor 351' are provided, and the positions of photodiode 32 and photodiode 33 are reversed.

If the directions of current i1 flowing to photodiode 33 and current i2 flowing to photodiode 32 are as shown in FIG. 35, i1 is positive and i2 is negative. FIG. 8 shows the relationship between voltage and current at node X when the circuit is interrupted at point Y. That is, if the luminance incident on photodiode 33 increases, current i1 increases, and when the luminance incident on photodiode 33 increases, current i2 decreases.

It is assumed below that im, it, it', and ic are the currents corresponding to luminance Pm, Pt, Pt', and Pc. In this case, currents i1 and i2 shown in FIG. 36 can be calculated from the following equations.

$$i1=im+it'+ic$$

$$i2=-it-ic$$

Current i1 and current i2 are added at node X, and the current i1+i2 flowing into opamp 34 is therefore im+it'−it. That is, currents ic and −ic corresponding to outside light luminance Pc are mutually cancelling. In addition, the current corresponding to the body movement component is (it'−it), the body movement component in the blood flow and the body movement component in tissue are mutually cancelling, and (it'−it) is extremely low compared with im. Therefore, pulse wave signal Vm can be approximated by the following equation.

$$Vm=k(im+it'-it)k*im$$

As a result, the output signal of difference operator 340 can be used as a pulse wave signal Vm from which body movement has been removed.

In this sensor unit 301, the emission characteristics of LED 310 and LED 311 are set to detect a body movement component and pulse wave component, respectively, by focusing on the sharp drop in the absorption characteristic of oxygenated hemoglobin $HbO_2$ at 600 nm. In addition, this sensor unit 301 can obtain a pulse wave signal Vm from which the body movement component has been removed because the body movement component detected by photodiode 32 is removed from the detection signal from photodiode 33. Moreover, the process obtaining this difference simultaneously cancels the outside light component, and a pulse wave signal Vm with a good S/N ratio can be obtained.

C-1-3: Configuration of the data processing circuit 501

Figure 37:
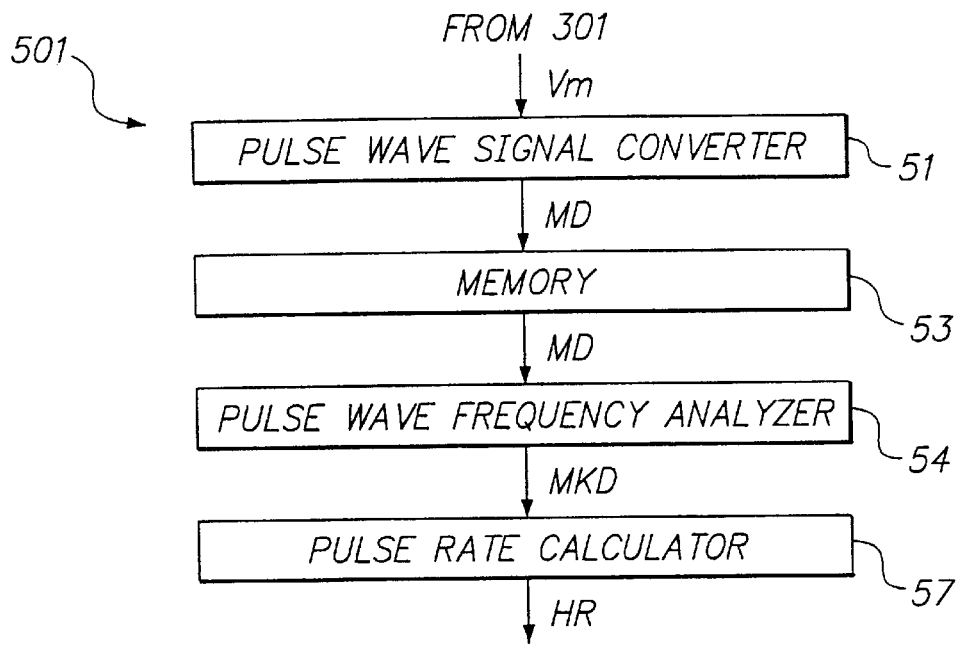
FIG. 37 is a block diagram of a data processing circuit 501 according to this preferred embodiment.

The data processing circuit 501 is described next with reference to FIG. 37. It should be noted that data processing circuit 501 is housed inside main body 10 as in the first embodiment. The data processing circuit 501 also specifically comprises CPU, RAM as working memory for the CPU, and ROM storing a program for achieving the above-noted function blocks.

In this figure, pulse wave signal converter 51 converts pulse wave signal Vm from sensor unit 301 from an analog signal to a digital signal, and outputs the result as pulse wave data MD. The memory 53 stores pulse wave data MD for a specific period. The pulse wave frequency analyzer 54 frequency analyzes the pulse wave data MD read from memory 53 to generate pulse wave analysis data MKD. Various methods can be used for this frequency analysis. The present exemplary embodiment uses a fast Fourier transform (FFT) because analysis can be completed in a short operating time.

Next, the pulse rate calculator 57 calculates the pulse rate HR based on spectrum power in pulse wave analysis data MKD, and outputs the result of the calculation to liquid crystal display 13. The pulse rate calculator 57 identifies the frequency Fh having the greatest spectrum power compared with the other spectrum lines. Because this frequency Fh is the fundamental frequency of the pulse wave signal Vm, the pulse rate calculator 57 obtains the pulse rate HR, which is the pulse count per minute, by calculating 60 Fh. The pulse rate HR thus calculated is then displayed on the liquid crystal display 13. It should be noted that if the S/N ratio of the pulse wave signal Vm is sufficiently high, it is possible to skip frequency analysis, simply wave shape the pulse wave signal Vm to convert it to a rectangular wave, obtain the period of this rectangular wave, and display the result as the pulse rate HR.

C-2. Operation of this Third Embodiment

The operation of a biological information measuring apparatus according to this third preferred embodiment of the present invention is described next. First, the user fastens the biological information measuring apparatus having a wristwatch design as shown in FIG. 32 to the wrist using wristband 12. Then, when running or otherwise exercising outdoors, a body movement component corresponding to, for example, arm swinging, is superposed to the blood flow through the blood vessels of the wrist.

First, the LED 311 of the sensor unit 301 emits light with a peak wavelength of 525 nm to the back of the wrist, and light reflected through the body is detected by photodiode 33. In addition, LED 310 emits light with a peak wavelength of 660 nm to the back of the wrist, and light reflected through the body is detected by photodiode 32.

It should be noted here that light with a peak wavelength of 660 nm is easily absorbed by tissues, but there is substantially no absorption by oxygenated hemoglobin $HbO_2$ in the blood stream. Therefore, current detected by photodiode 32 corresponds to variation in tissue movement as the body moves. On the other hand, light with a peak wavelength of 525 nm is easily absorbed by oxygenated hemoglobin $HbO_2$ in the blood. As a result, current detected by photodiode 33 reflects the movement of the blood stream. In this case, the blood stream includes a body movement component corresponding to movement of the body superposed on the pulse wave component corresponding to the pulse. The current detected by photodiode 32 thus has a body movement component superposed on the pulse wave component. In addition, because outside light passes wrist tissue and enters the photodiodes 32 and 33, an outside light component is also superposed on the output current of the photodiodes 32 and 33.

Next, the sensor unit 301 calculates the difference between the output current of photodiode 33 and the output current of photodiode 32, and based on the result generates pulse wave signal Vm. This differencing operation cancels the body movement component and outside light component.

Figure 38:
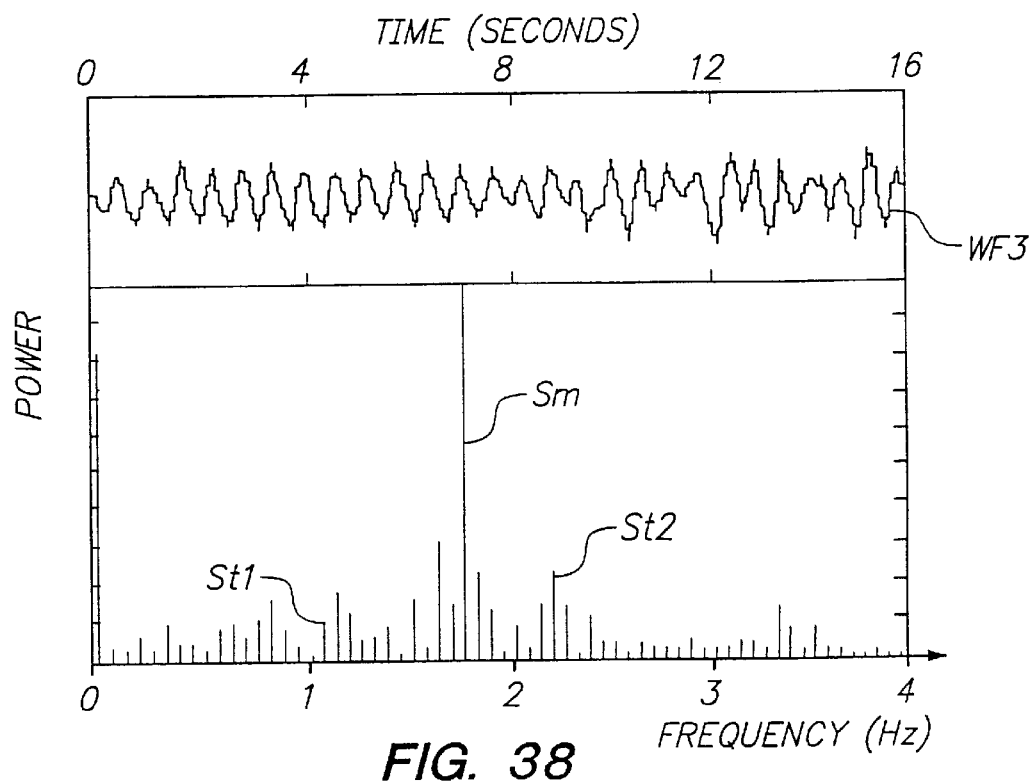
FIG. 38 is a graph of the signal waveform of a pulse wave signal and frequency analysis thereof according to this preferred embodiment.

For example, if the signal waveform WF1 detected by photodiode 33 and the frequency analysis result thereof are as shown in FIG. 29, and the signal waveform WF2 detected by photodiode 32 and the frequency analysis result thereof are as shown in FIG. 30, the signal waveform WF3 of the pulse wave signal Vm output from sensor unit 301 and the frequency analysis result thereof are as shown in FIG. 38. By comparing these figures, it is known that the level of the body movement components St1 and St2 superposed on the pulse wave signal Vm is significantly reduced compared with the body movement components St1 and St2 of the signal detected by photodiode 33 shown in FIG. 29. The sensor unit 301 can thus generate a pulse wave signal Vm with a good S/N ratio.

Next, when the pulse wave signal Vm is supplied to the data processing circuit 501, the pulse wave signal Vm is converted from an analog signal to a digital signal by pulse wave signal converter 51, resulting in pulse wave data MD. The pulse wave data MD is sequentially stored to the memory 53, and then read out at a predetermined timing to the pulse rate calculator 57. Next, pulse wave frequency analyzer 54 applies a FFT process to the pulse wave data MD, performs a frequency analysis, and generates pulse wave analysis data MKD. Then, the pulse rate calculator 57 identifies the spectrum having the highest spectrum power in the pulse wave analysis data MKD. The pulse rate calculator 57 then multiplies the frequency Fh of this spectrum by 60 to calculate the pulse rate HR, and this pulse rate HR is displayed on the liquid crystal display 13. As a result, the user can know his or her accurate pulse rate HR based on a pulse wave signal Vm from which body movement has been removed even while exercising. As a result, a user can monitor his or her own health while running, and can thus train more effectively.

It is therefore possible with a biological information measuring apparatus according to this third exemplary embodiment to obtain a pulse rate HR or other biological information using a single fast Fourier transform process instead of two FFT processes as are required with a conventional device because the difference operator 340 calculates the difference of the output signals from the photodiodes 32 and 33 to generate a pulse wave signal Vm in which a body movement component is suppressed. As a result, the overall configuration of the apparatus can be simplified, and the processing load on the CPU and other components can be reduced.

In addition, because both the body movement component and effects of outside light are simultaneously cancelled by the differencing operation of the difference operator 340, the pulse rate HR, for example, can be accurately measured even when exercising outdoors.

Figure 39:
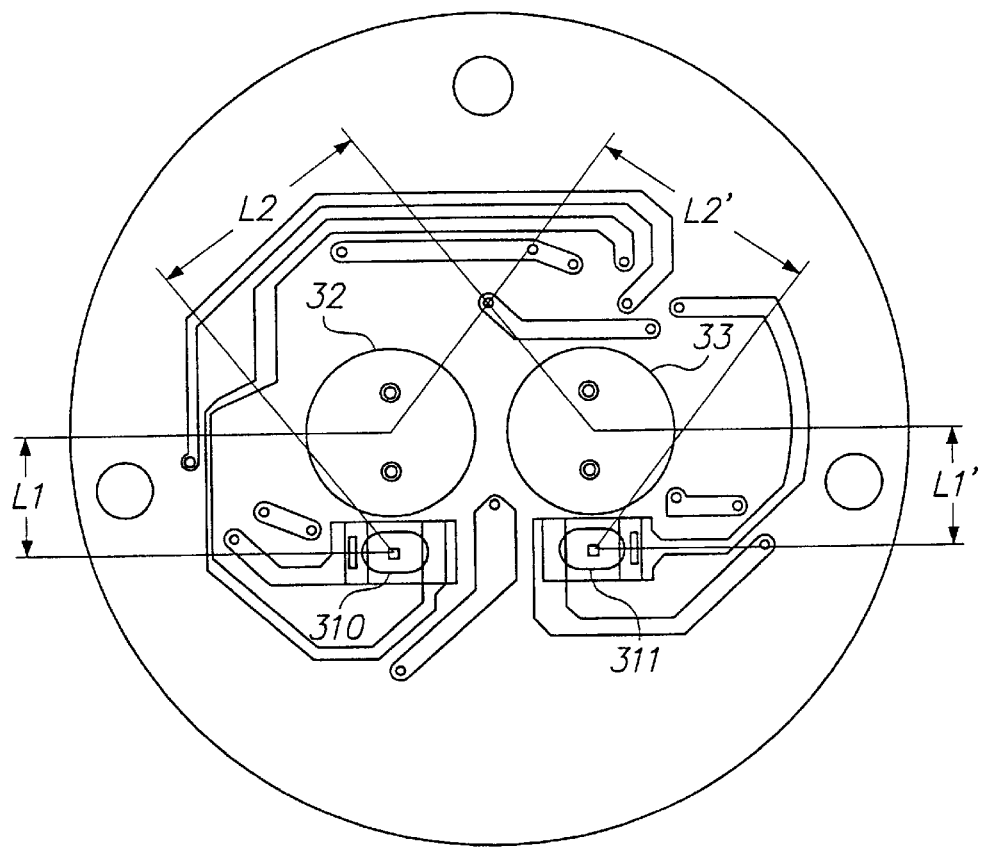
FIG. 39 is a plan view of a sensor unit 301 according to an alternative version of this third embodiment.

C-3. Variations of the Third Embodiment (1) In the above-described third embodiment, the LEDs 310 and 311 and photodiodes 32 and 33 of the sensor unit 301 are positioned relative to each other in a straight line as shown in FIG. 33, but the present invention shall not be so limited. That is, they can be positioned in any way such that distance L1 from LED 310 to photodiode 32 differs from distance L2 from LED 310 to photodiode 33, and distances L1' and L2' are also different. For example, they can be arranged as shown in FIG. 39 such that the line between LED 310 and photodiode 32 is perpendicular to the line between photodiodes 32 and 33, and the line between LED 311 and photodiode 33 is perpendicular to the line between photodiodes 32 and 33.

(2) In the above-described third embodiment, the pulse wave signal Vm is generated by the sensor unit 301 based on a difference between the detection current of photodiode 32 and the detection current of photodiode 33. It is alternatively possible to adjust the gain of the detection current detected by the photodiode 32 so that the body movement component superposed on the pulse wave component is accurately cancelled.

For example, it is sufficient to adjust the resistance of resistor r in the difference operator 340 of the sensor unit 300 shown in FIG. 35. In addition, in the sensor unit 301 shown in FIG. 36, the resistance of resistor 351 can be adjusted to vary luminance Pt associated with body movement.

D. Embodiment 4

In the third embodiment of the present invention a pulse wave signal Vm with a suppressed body movement component is generated using a difference operator 340. A fast Fourier transform is then applied to the pulse wave signal to calculate the pulse rate HR. There are times, however, when the body movement component cannot be sufficiently suppressed, such as during aerobics exercises when arm swinging is irregular and there is strong movement. A biological information measuring apparatus according to a fourth embodiment of the present invention addresses this by applying an autocorrelation function to the pulse wave signal Vm to suppress an irregular body movement component contained in the pulse wave signal Vm. An accurate pulse rate HR is then calculated by frequency analyzing the result of this pulse wave signal Vm autocorrelation operation.

D-1. Configuration of the Fourth Embodiment

Figure 40:
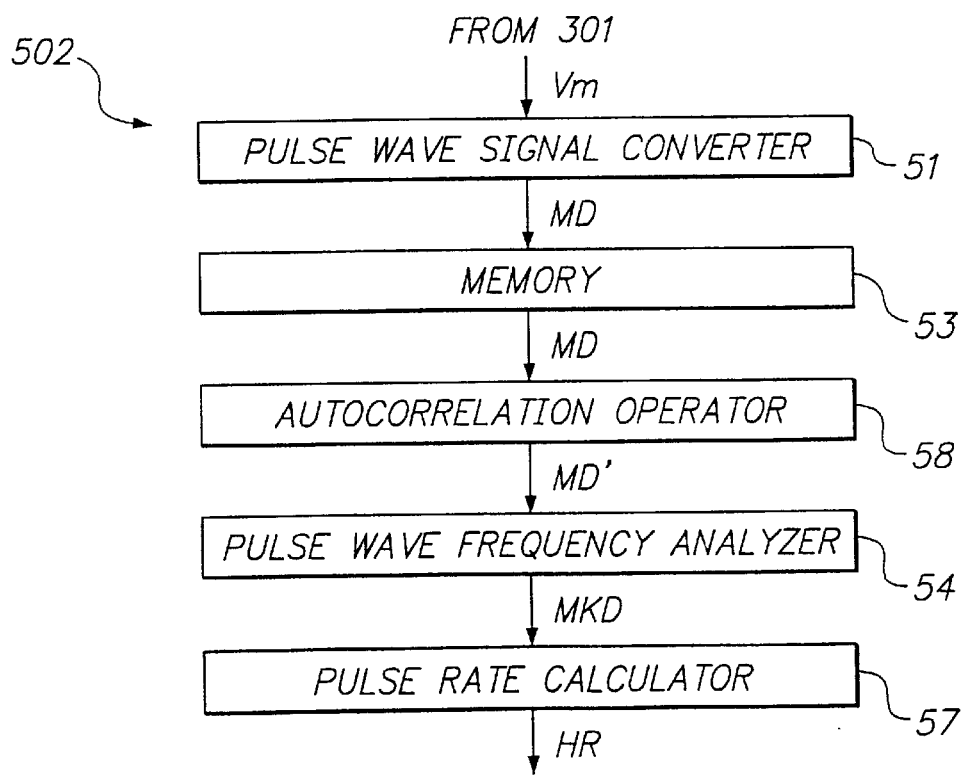
FIG. 40 is a block diagram of a data processing circuit 502 according to a fourth embodiment of the present invention.

A biological information measuring apparatus according to this fourth embodiment is identical to the biological information measuring apparatus according to the third embodiment except for the addition of an autocorrelation operator 58 to the data processing circuit 501 of the third embodiment. FIG. 40 is a block diagram of a data processing circuit 502 according to this fourth embodiment. This data processing circuit 502 has an autocorrelation operator 58 between the memory 53 and pulse wave frequency analyzer 54. The autocorrelation operator 58 calculates an autocorrelation function described further below using the pulse wave data MD as input sample data to generate autocorrelated pulse wave data MD'.

This autocorrelation function is described below. The pulse wave indicates the pulsations that occur as the flow of blood through the arteries created by contractions of the heart travels through the arteries. As a result, the pulse wave has a constant period synchronized to the heart beat. In contrast to this, irregular body movement does not have a period. The autocorrelation function can enhance the part with a period. It is therefore possible to suppress the body movement component and enhance the pulse wave component by applying an autocorrelation function to pulse wave data MD containing both an irregular body movement component and regular pulse wave component.

If x(t) represents irregular variation, and x(t) has periodic variation of period T, x(t) can be obtained by the following equation:

$$x(t)=x(t\pm nT)$$

where n=0, 1, 2 . . .

In other words, the waveform will become superimposed on itself when the period is shifted a particular integer multiple. If irregular variation x(t) has strong periodicity, shifting the wave an integer multiple of the period along the time base will produce a wave similar to the original. It is therefore possible to determine the similarity between a waveform shifted time τ and the original waveform, and identify the period component of the change, by determining the correlation between x(t) and x(t+τ).

The autocorrelation function is defined as the average of the products of two variations offset by time τ where x(t) is the irregular change relative to time, and is obtained by the following equation.

$$C(\tau)=E[x(t)x(t+\tau)]$$

where E is the ensemble average, and can be substituted with a time average in a stationary stochastic process. The autocorrelation function C(τ) can therefore be expressed by the following equation.

$$C(\tau)=\lim 1/T \int_0^T x(t) \cdot x(t+\tau)dt$$

The above equation is the autocorrelation function C(τ) for a continuous signal. The autocorrelation function for discrete data is as follows.

$$C(\tau)=1/N-i \; \text{SUM}[N-1][j=1]\{x(j)\cdot x(j+i)\}$$

i=0, 1, 2 . . . N−1

Note that for X(j), j=1, 2, . . . N where N is the finite number of samples.

The autocorrelation operator 58 applies the product sum operation defined by the above equation to N pulse wave data MD(j) to generate autocorrelated pulse wave data MD'. This autocorrelated pulse wave data MD' is then compared with the pulse wave data MD to suppress the irregular body movement component and enhance the pulse wave component. It is therefore possible to increase the S/N ratio of the pulse wave analysis data MKD generated by the pulse wave frequency analyzer 54. As a result, the pulse rate calculator 57 can accurately identify the frequency of the pulse spectrum, and calculate an accurate pulse rate HR.

D-2. Operation of Embodiment 4

The operation of a biological information measuring apparatus according to this fourth embodiment of the present invention is the same as that of the third embodiment except for the above-noted autocorrelation calculation. As a result, the operation of the autocorrelation operator 58 is described with reference to comparative examples. It should be noted that in each of the following examples, measurements taken by the sensor unit were obtained with irregular body movement.

Comparison 1

Figure 41:
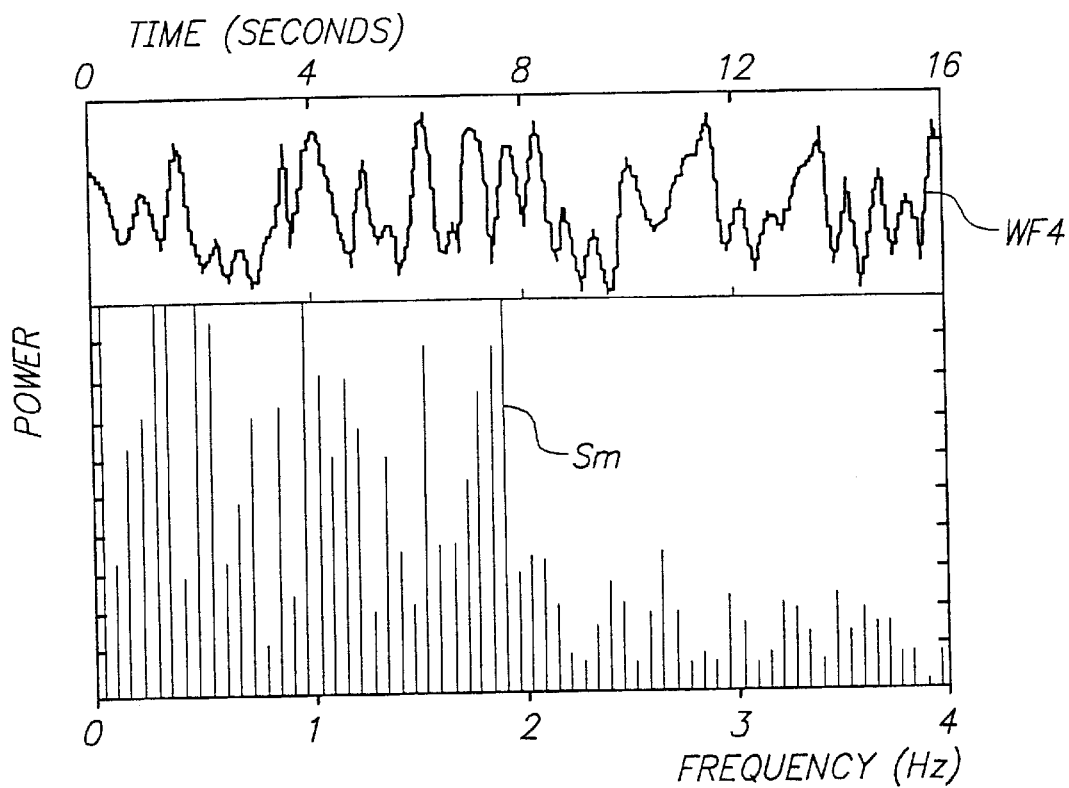
FIG. 41 is a graph of the output signal waveform measured as a first comparison and frequency analysis thereof.

In this first comparison, the LED 31 of the sensor unit 30 shown in FIG. 5 has an emission wavelength characteristic as shown in FIG. 28 (525 nm center wavelength of emissions). FIG. 41 is a graph showing the output signal waveform WF4 of sensor unit 30 in this first comparison, and the frequency analysis result thereof. In this case, output signal waveform WF4 has slight periodicity. However, it will be known from the frequency analysis results that the power of pulse spectrum Sm is comparable to the power of other spectra. It is therefore not possible with this configuration to identify the frequency of the pulse spectrum Sm when there is also irregular body movement.

Comparison 2

Figure 42:
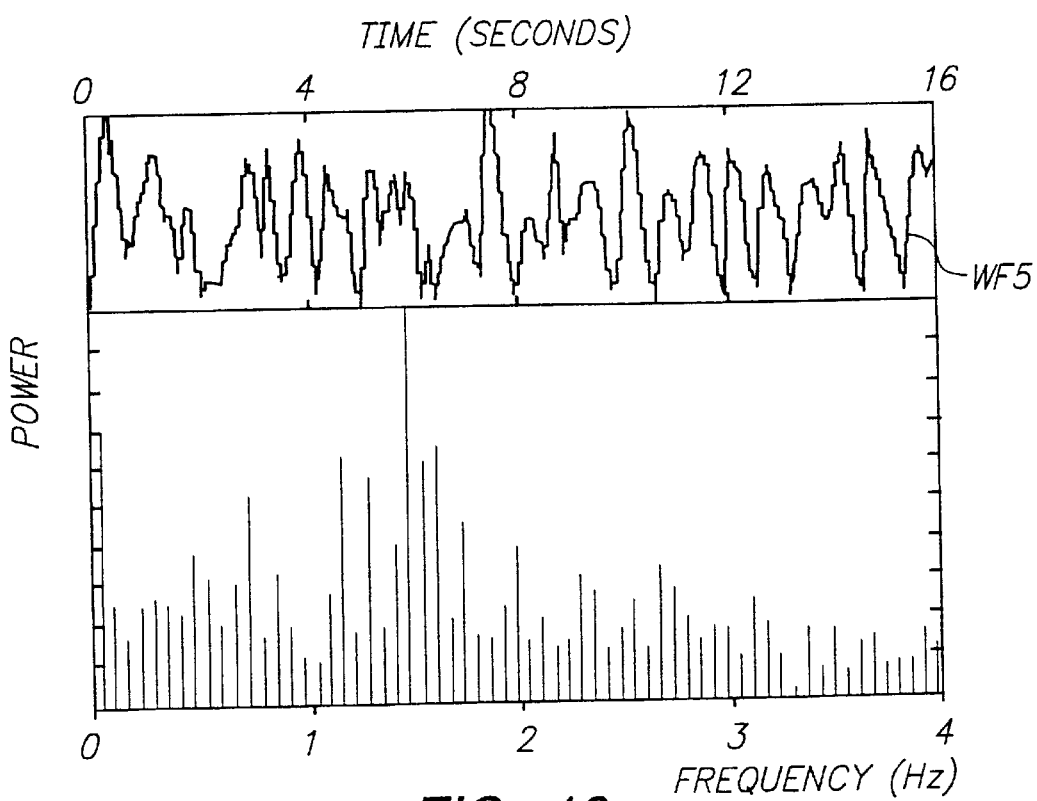
FIG. 42 is a graph of the output signal waveform measured as a second comparison and frequency analysis thereof.

In this second comparison, the LED 31 of the sensor unit 30 shown in FIG. 5 has an emission wavelength characteristic as shown in FIG. 24 (660 nm center wavelength of emissions). FIG. 42 is a graph showing the output signal waveform WF5 of sensor unit 30 in this second comparison, and the frequency analysis result thereof. Because the center of the wavelength band in this case is 660 nm, the output signal waveform WF5 is indicative of a body movement component.

Comparison 3

Figure 43:
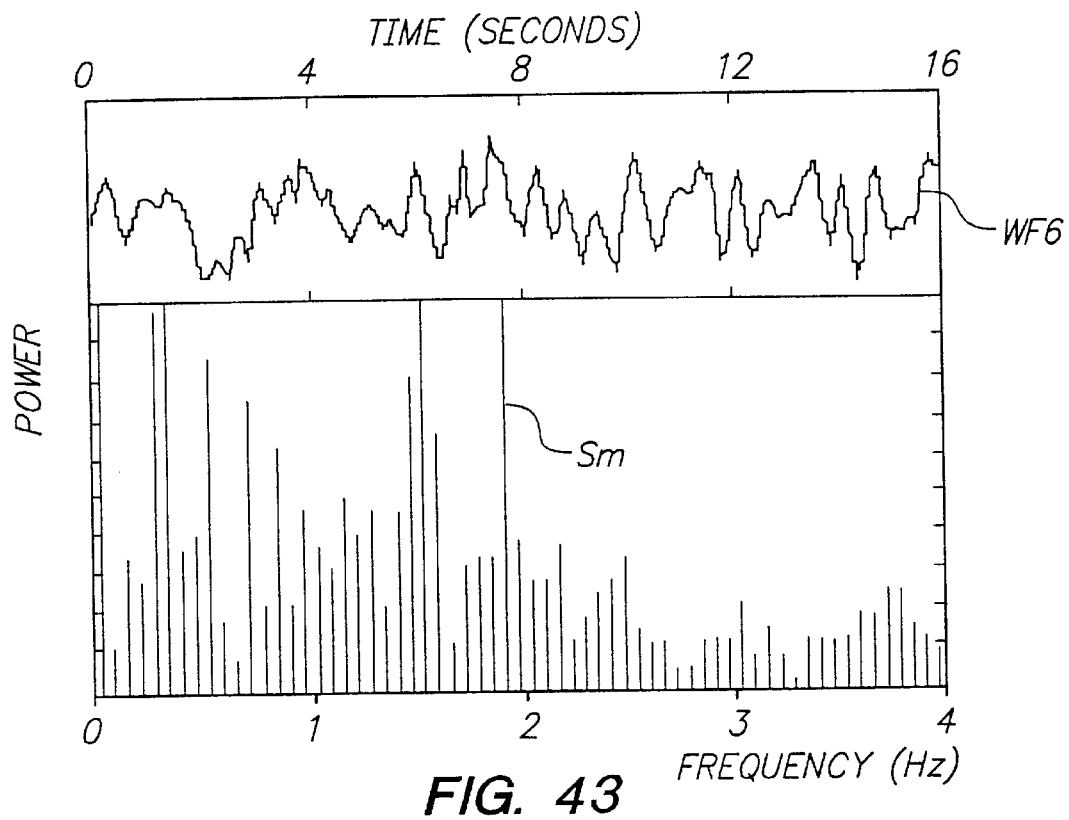
FIG. 43 is a graph of the output signal waveform measured as a third comparison and frequency analysis thereof.

A sensor unit 300 according to the third embodiment is used in this third comparison. FIG. 43 is a graph showing the output signal waveform WF6 of sensor unit 300 in this third comparison, and the frequency analysis result thereof. In this case, the sensor unit 300 suppresses the body movement component. The pulse wave component therefore appears enhanced in this output signal waveform WF6 when compared with the output signal waveform WF4 shown in FIG. 4. However, when the frequency analysis results of output signal waveform WF6 shown in FIG. 43 are examined, a spectrum with power equivalent to pulse spectrum Sm is also observed. It is therefore not possible with this configuration to identify the frequency of pulse spectrum Sm when there is also irregular body movement.

Working version

Figure 44:
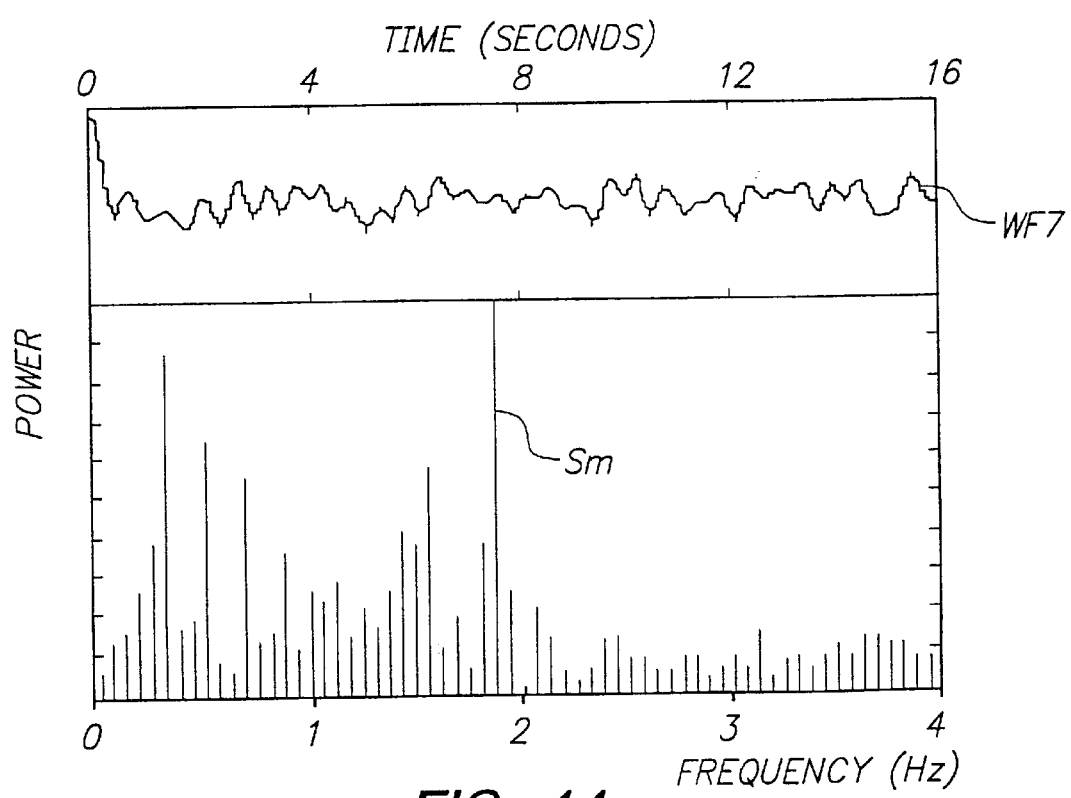
FIG. 44 is a graph of the output signal waveform measured in a preferred embodiment of the invention and frequency analysis thereof.

In contrast to the above-noted third comparison, a working version of the present embodiment applies the output signal waveform WF6 to the autocorrelation operator 58 as pulse wave data MD, and thus applies an autocorrelation function thereto to generate autocorrelated pulse wave data MD'. FIG. 44 is a graph showing the waveform WF7, which is indicative of the autocorrelated pulse wave data MD' in this working version, and the frequency analysis result thereof. It is known from this waveform WF7 that the body movement component is suppressed by applying an autocorrelation function, and a periodic pulse wave component is enhanced. It is also known from the frequency analysis of waveform WF7 that the power of pulse spectrum Sm is strongest when compared with the power of other spectra. It is therefore possible with this configuration to identify the frequency of the pulse spectrum Sm when there is also irregular body movement.

It is therefore possible as described above according to this fourth preferred embodiment of the present invention to suppress an irregular body movement component and enhance a pulse wave component with a specific period by applying an autocorrelation function to the pulse wave data MD. As a result, the pulse rate calculator 57 can calculate a more accurate pulse rate HR.

D-3. Variations of the Fourth Embodiment

In the above-described fourth embodiment, an autocorrelation operator 58 applies a process for enhancing a pulse wave component having a particular period. The pulse rate HR can therefore be calculated directly from the autocorrelated pulse wave data MD', and the pulse wave frequency analyzer 54 and pulse rate calculator 57 can be omitted. In this case, the autocorrelated pulse wave data MD' is compared with reference level data (equivalent to the dc level) to calculate the pulse wave period, and the pulse rate HR can then be calculated based on the result. This biological information measuring apparatus does not require frequency analysis, and can therefore be achieved using a CPU with a slow processor speed. Power consumption can therefore also be reduced because the processing load imposed by frequency analysis is not incurred. The present embodiment is therefore suitable for a low cost portable device.

E. Embodiment 5

In the fourth embodiment an autocorrelation function is applied by an autocorrelation operator 58. The calculating load of this autocorrelation function is great, however, because it is a product sum operation. The autocorrelation function is applied, however, to suppress irregular body movement components and enhance regular pulse wave components. Therefore, if the body movement component has a well defined period, suppression of the body movement component by the autocorrelation function is minimal. This fifth embodiment of the present invention addresses this by calculating the S/N ratio of the body movement signal Vt, and determining whether to apply an autocorrelation function based on the result.

E-1. Data Processing Circuit 503

Figure 45:
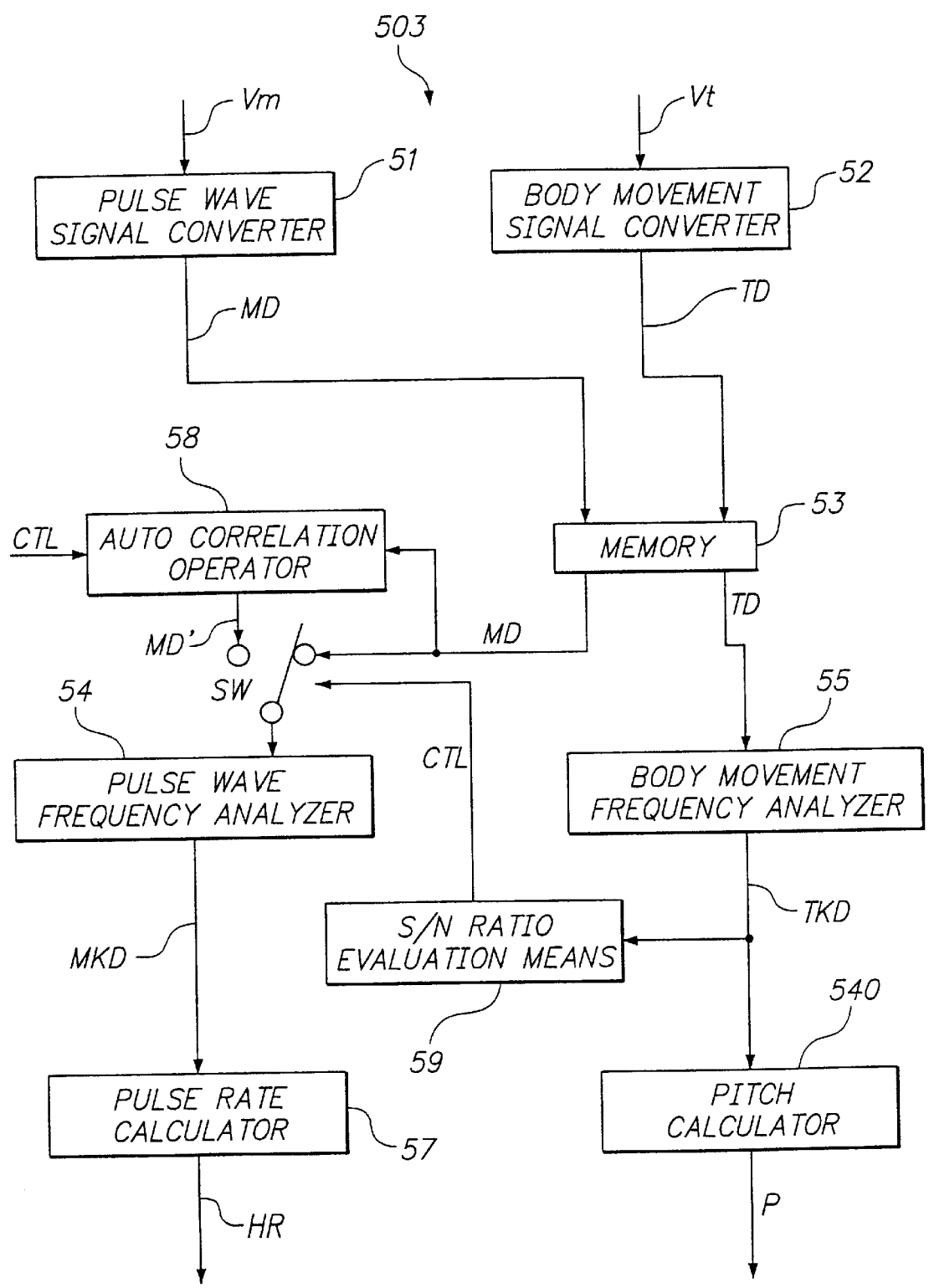
FIG. 45 is a block diagram of a data processing circuit 503 according to a fifth embodiment of the present invention.

FIG. 45 is a block diagram for a data processing circuit 503 in this fifth embodiment of the present invention. The pulse wave signal Vm input to this data processing circuit 503 is generated, for example, by the sensor unit 300 in the third comparison described above in the fourth embodiment. The body movement signal Vt is generated, for example, by the sensor unit 30 in the second comparison described above in the fourth embodiment (where the center wavelength of LED emission is 660 nm).

The pulse wave signal Vm is converted to a digital signal by the pulse wave signal converter 51, resulting in pulse wave data MD. The body movement signal Vt is converted to a digital signal by the body movement signal converter 52, resulting in body movement data TD. Pulse wave data MD and body movement data TD are stored to memory 53, and are read out at a specific timing.

A S/N ratio evaluation means 59 evaluates the S/N ratio of the body movement data based on body movement analysis data TKD. More specifically, it first determines the spectrum with the highest level in the body movement analysis data TKD. Next, it calculates the S/N ratio of this spectrum. Next, it compares the calculated S/N ratio with a predefined reference value, and based on the result generates control signal CTL.

The S/N ratio can be calculated using the following equation where L1, L2, . . . Ln represent each spectrum level, and Lmax is the highest spectrum level.

$$S/N \text{ ratio} = sqr[L_{max}^2/(L1^2 + L2^2 + \ldots Ln^2)]$$

Calculating the above equation, however, imposes a significant load on the processor because the square of n values must be calculated. It is therefore possible to calculate the S/N ratio using the following simplified equation.

$$S/N \text{ ratio} = L_{max}/(L1 + L2 + \ldots Ln)$$

If the user engages in regular exercise, the resulting regular body movement increases the S/N ratio. Applying an autocorrelation function in this case has a minimal effect suppressing the body movement component. However, if the user engages in irregular exercise, the S/N ratio drops because of the resulting irregular body movement. In this case, the autocorrelation function effectively suppresses the body movement component. It is therefore possible to determine whether or not to apply an autocorrelation function based on the S/N ratio. The above-noted reference value is set so that the desired effect is obtained by the autocorrelation function. As a result, the S/N ratio evaluation means 59 functions to detect the degree of body movement irregularity, and then based on the result determine whether or not to apply an autocorrelation function.

The control signal CTL output from the S/N ratio evaluation means 59 is applied to the autocorrelation operator 58 and switch SW. Operation of the autocorrelation operator 58 is controlled by the control signal CTL. The autocorrelation operator 58 thus stops operating when the S/N ratio is high, and applies the autocorrelation function when the S/N ratio is low. The switch SW selects either pulse wave data MD or autocorrelated pulse wave data MD' based on the control signal CTL. When the S/N ratio is high, the switch SW outputs pulse wave data MD; when the S/N ratio is low, it outputs autocorrelated pulse wave data MD'. As a result, the autocorrelation function is applied only when the effect of the autocorrelation function operation will be significant.

As thus described, an autocorrelation function operation is applied based on the S/N ratio (degree of irregularity of body movement) of the body movement signal Vt in this fifth embodiment of the present invention, thereby reducing the processor load on the CPU and reducing power consumption.

E-2. Variations of the Fifth Embodiment (1) As in a variation of the fourth embodiment, it is also possible in this fifth embodiment to calculate the pulse rate HR directly from the autocorrelated pulse wave data MD' or pulse wave data MD. It is therefore possible to eliminate the pulse wave frequency analyzer 54 and pulse rate calculator 57.

(2) In addition, when the irregularity (inconsistency) of the analyzed data is pronounced, the pulse rate HR can also be calculated as described below. First, a specific autocorrelation function is separately applied to the body movement data TD and pulse wave data MD to generate autocorrelated body movement data and autocorrelated pulse wave data MD'. Next, the difference between the autocorrelated pulse wave data MD' and autocorrelated body movement data is calculated. Next, the pulse rate HR is calculated by period analysis or frequency analysis of the calculated difference.

(3) The body movement signal Vt in this fifth embodiment can alternatively be the signal detected by the acceleration detector 60 described in the first embodiment above.

F. Embodiment 6

In the above third embodiment, a body movement component is removed by using LEDs 310 and 311 for pulse wave detection and body movement detection. In this sixth embodiment, however, the body movement detection LED 311 is omitted, and the pulse wave signal Vm is measured from the back of the wrist.

Figure 46:
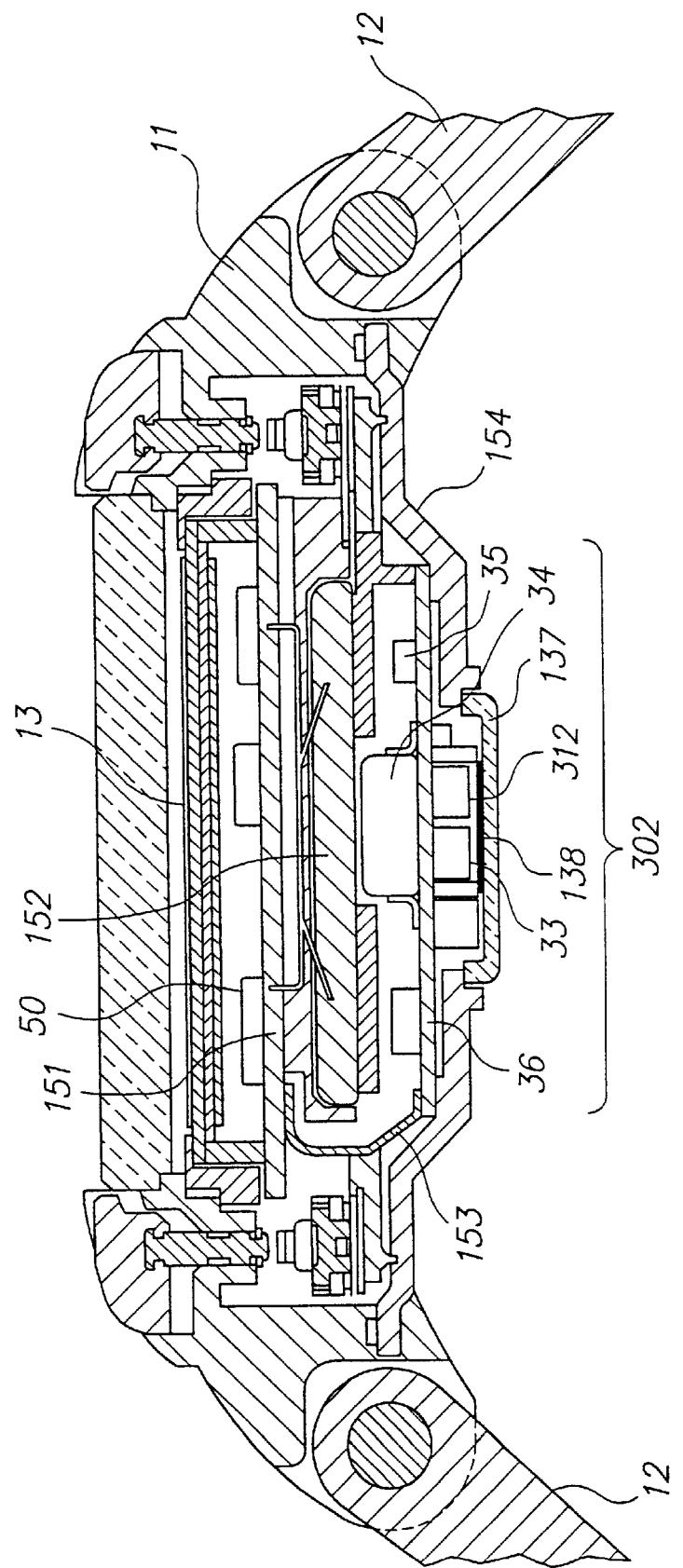
FIG. 46 is a section view of a biological information measuring apparatus according to a sixth embodiment of the present invention.

FIG. 46 is a section view of a biological information measuring apparatus according to this preferred embodiment. A biological information measuring apparatus according to this sixth embodiment differs from a biological information measuring apparatus according to the third embodiment as shown in FIG. 32 in that LED 310 and photodiode 32 are removed from the sensor unit 302, an LED 312 is provided in place of LED 310, and a filter 138 is provided.

It should be noted here that the filter 138 is disposed between transparent glass 37 and LED 312 and photodiode 32. This means that light emitted from LED 311 is emitted to the back of the wrist through the filter 138, and light reflected by body tissues is incident on photodiode 33 through the filter 138.

The spectral sensitivity characteristic of photodiode 33 is shown in FIG. 6, that is, the photodiode 33 is sensitive in the wavelength range from 250 nm to 850 nm. In addition, the LED 312 is set to emit light in the wavelength range from 500 nm to 600 nm. The LED 312 in this case can have emission characteristics as shown in FIG. 7, for example. Alternatively, emissions may range from 550 nm to 650 nm, for example, such that part of the light is emitted in the range 500 nm to 600 nm.

The transmission characteristic of the filter 138 is set so that the total wavelength range of light used for measurement by the measurement system from the LED 311 to the photodiode 33 is within the range 500 nm to 600 nm. For example, if the LED 312 emits light of a wavelength between 550 nm and 650 nm, the filter 138 passes light in the range 550 nm to 600 nm, and sufficiently attenuates light with a wavelength from 600 nm to 650 nm.

Figure 47:
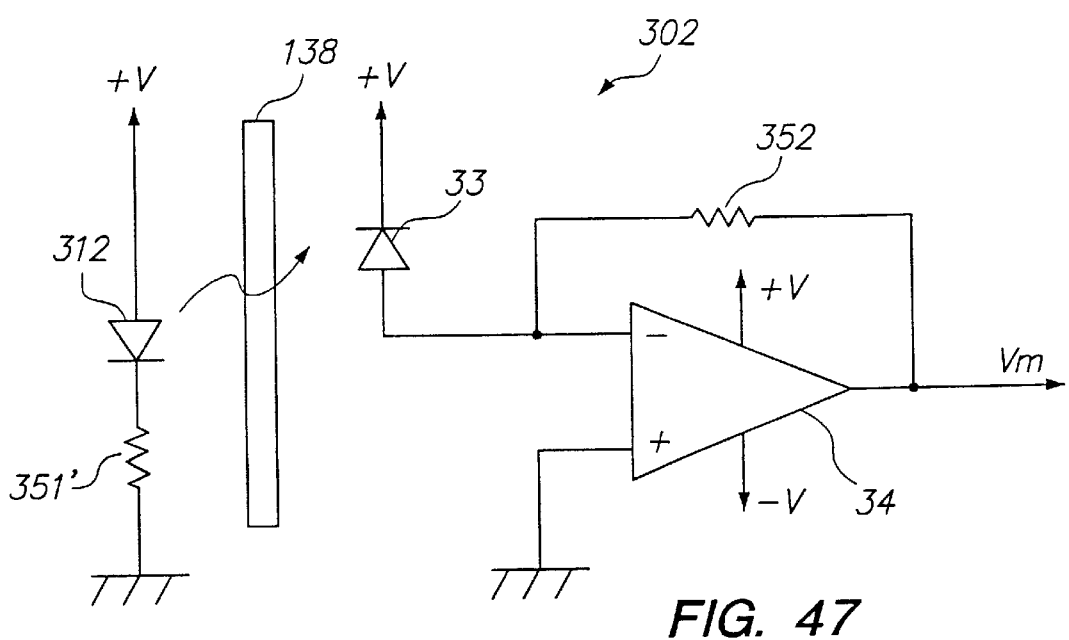
FIG. 47 is a circuit diagram showing the electrical configuration of a sensor unit 302 according to this preferred embodiment.

A circuit diagram showing the electrical configuration of sensor unit 302 is shown in FIG. 47. In this figure, when power source +V is supplied to the LED 312, a current determined by the value of resistor 351' flows to the LED 312, and light is emitted. The emitted light passes the filter 138, whereby light is emitted to the wrist and absorbed by oxygenated hemoglobin $HbO^2$ in the blood stream. Unabsorbed light is reflected by body tissues. This reflected light passes back through the filter 138, and is incident on photodiode 33.

The cathode of photodiode 33 is connected to positive power source +V, and the anode is connected to the negative input terminal of opamp 34. The positive input terminal of opamp 34 is to ground. The anode of photodiode 33 is to ground through a virtual short circuit. The photodiode 33 is thus reverse biased, and when light is incident thereon, current flows according to the amount of incident light. The opamp 34 and resistor 352 voltage convert and amplify the current from photodiode 33. The output signal of the opamp 34 thus varies according to the amount of incident light.

As described above, however, the light absorption characteristic differs in body tissues and oxygenated hemoglobin $HbO_2$ in the blood stream according to the wavelength of light used for measurements. Conceivably, therefore, there is a wavelength range that is suitable for detecting a pulse wave component.

The present inventors, therefore, experimentally investigated the wavelength range suited to detecting a pulse wave component by varying the primary wavelength (peak wavelength) used for measurements in Japanese test subjects.

In this test, the sensor unit of the embodiment was at the base of a finger and the back of the wrist, and the arms were swung at a pitch of 130 to simulate running. The detected pulse wave signal Vm was then frequency analyzed. The body movement component in this case will correspond to a pitch of 130. This fact was therefore used to determine from the results of the frequency analysis the spectrum estimated to be the pulse component and the spectrum estimated to be the body movement component. The ratio therebetween was then obtained and graphed in FIGS. 48 and 49. The horizontal axis in both figures is the primary wavelength of light used for measurement, and the vertical axis is the ratio between the frequency spectrum height of the pulse component and the frequency spectrum height of the body movement component (pulse spectrum height/body movement spectrum height, the MT ratio below). As the height of the pulse spectrum increases relative to the height of the body movement spectrum, the less frequently the body movement spectrum is falsely detected as the pulse spectrum. Therefore, the greater the MT ratio, the better the pulse wave detection characteristics.

Figure 48:
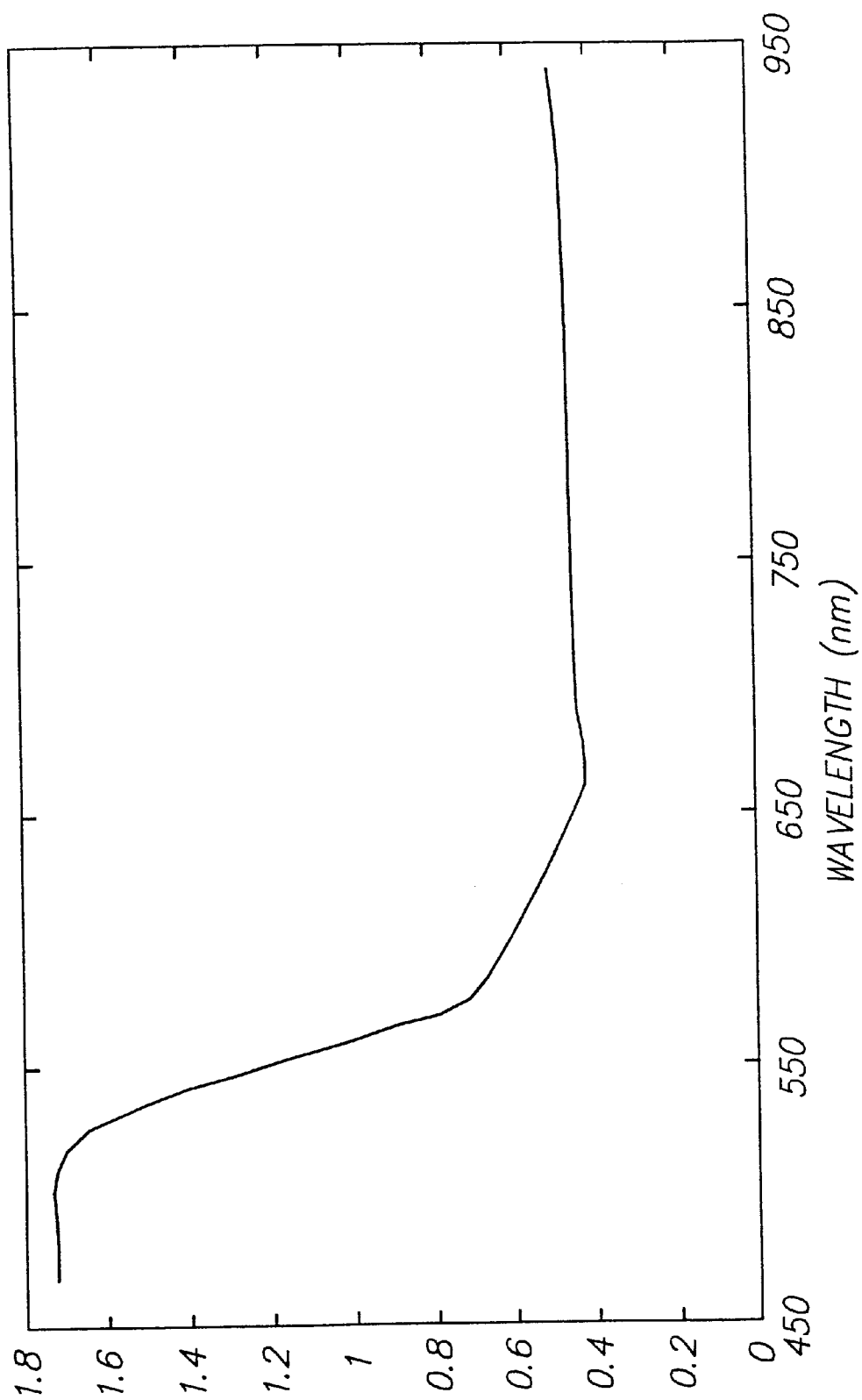
FIG. 48 is a graph of the relationship between wavelength of light used for measurement, and the percentage of the pulse spectrum in the body movement spectrum based on measurements obtained at the base of the finger.
Figure 49:
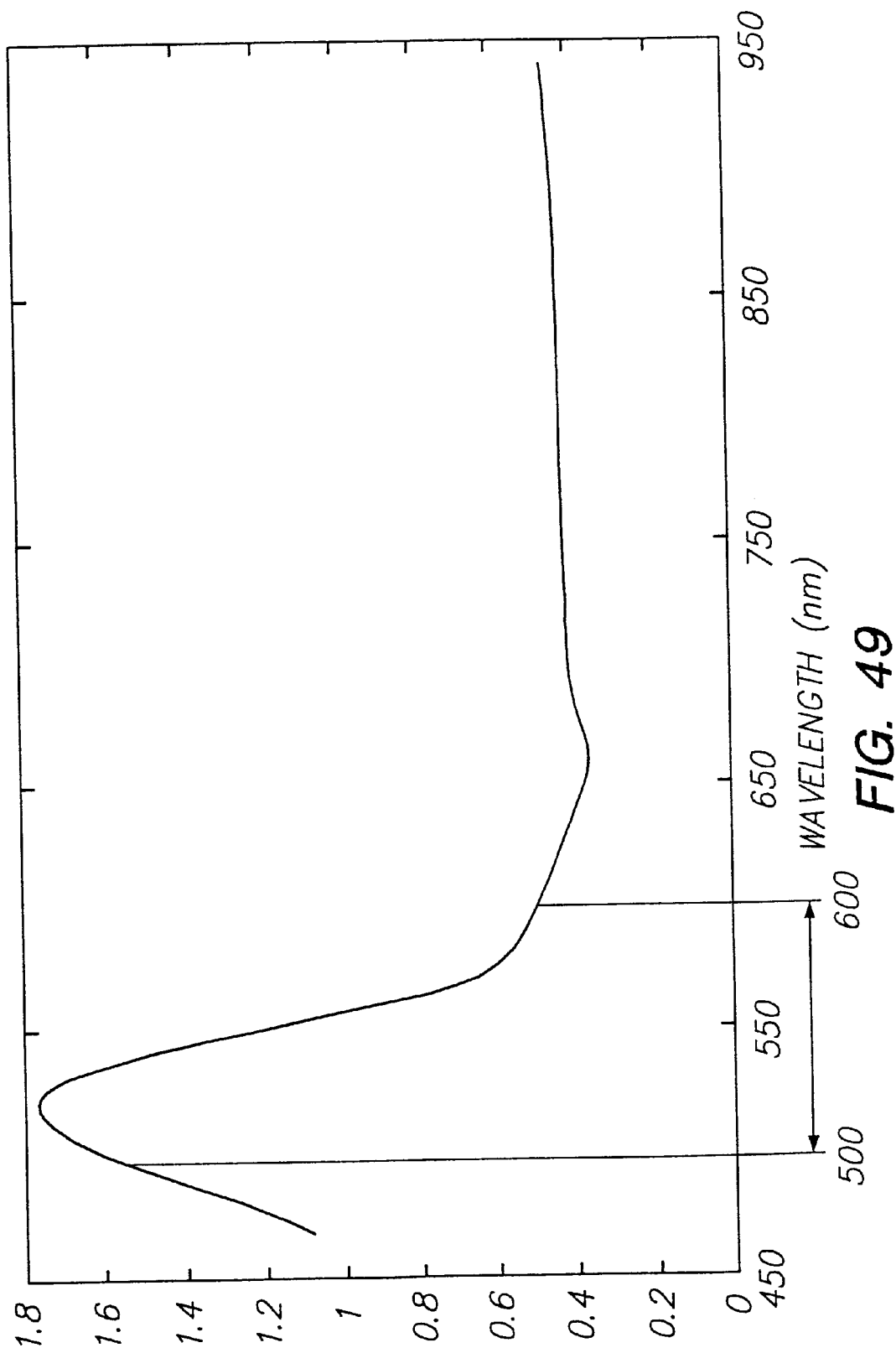
FIG. 49 is a graph of the relationship between wavelength of light used for measurement, and the percentage of the pulse spectrum in the body movement spectrum based on measurements obtained at the back of the wrist.

FIG. 48 shows the results of measurements at the base of a finger, and FIG. 49 shows the results from the back of the wrist. As will be known from both results, there is a wavelength range suited to pulse wave detection and a wavelength range suited to body movement detection with the border therebetween at approximately 600 nm. This matches the rapid drop in the molecular extinction coefficient of oxygenated hemoglobin $HbO_2$ at a wavelength of 600 nm as shown in FIG. 23. In other words, the MT ratio of the pulse wave signal Vm deteriorates in a wavelength range from 600 nm and above because there is substantially no absorption of emitted light by oxygenated hemoglobin $HbO_2$ in the blood stream. On the other hand, at wavelengths below 600 nm, there is an increase in absorption by oxygenated hemoglobin $HbO_2$, and the MT ratio of the pulse wave signal Vm increases.

Comparing FIG. 48 and FIG. 49 we know that the MT ratio drops at wavelengths below 500 nm in measurements taken at the back of the wrist compared with measurements taken at the base of a finger. This is because there is more melanin in the skin on the back of the wrist than at the base of a finger. That is, melanin has a tendency to reflect and disperse short wavelength light, and as the wavelength drops, it is therefore more difficult for emitted light to penetrate into the body. Therefore, because it becomes more difficult for emitted light to be absorbed by blood flowing inside the body, the MT ratio of the pulse spectrum drops. It should be noted that while the results in FIG. 48 and FIG. 49 were obtained with a pitch of 130, there is no change in the relative tendencies shown in the figures when the pitch changes.

The wavelength range of light used for measurements is set in the range 500 nm to 600 nm in a biological information measuring apparatus according to this preferred embodiment having a wristwatch construction because the back of the wrist is the detection site for the pulse wave signal Vm. The measurement results described above were obtained with Japanese subjects, but similar results are obtained with Caucasians. In addition, measuring in the 500 nm to 600 nm range is even more preferable in blacks because even more melanin is present.

When a pulse wave signal Vm thus detected is applied to the data processing circuit 501, the data processing circuit 501 calculates the pulse rate HR based on the pulse wave signal Vm as in the third embodiment, and displays the result on the liquid crystal display 13.

As described above, a pulse wave signal Vm with a good S/N ratio can be obtained in the present embodiment because the pulse wave signal Vm is measured at the back of the wrist using light in the 500 nm to 600 nm wavelength range that is suitable for detecting a pulse wave component. In addition, an accurate pulse rate HR can be calculated even while exercising because the pulse rate HR is obtained using this pulse wave signal Vm.

It is also possible in the above sixth embodiment to set the primary wavelength used for measurement to 500 nm to 600 nm without using a filter 138 by using a device emitting with a peak wavelength of 525 nm as the LED 312 (light emitting means), and using a photodiode 33 with spectral sensitivity from 400 nm to 800 nm as the photodetection means. It is also possible to set the light emitting means to emit light with energy in the 400 nm to 800 nm wavelength range, and set the spectral sensitivity of the photodetection means to 500 nm to 600 nm. In other words, various configurations may be used insofar as the wavelength range used for measurements is set to 500 nm to 600 nm.

Furthermore, the back of the wrist is the detection site in the above sixth embodiment. However, there is not a significant difference in the amount of melanin present in the back of the wrist, the underside of the wrist, or other points around the arm. It is therefore possible to appropriately modify the appearance of the biological information measuring apparatus so that measurements can be taken where desired around the wrist or arm.

G. Applied Examples

The present invention shall not be limited to the above-described embodiments, and can be modified in various ways as described below.

(1) In the first embodiment, and in the second to sixth embodiments, the pulse rate HR is calculated based on pulse wave analysis data MKD by a data processing circuit, but the invention shall not be so limited. For example, the low frequency component of the pulse wave analysis data MKD can be analyzed to calculate the respiration rate. In addition, an inverse FFT operation can be applied to the pulse wave analysis data MKD to evaluate various pulse phenomena, such as the normal pulse rate, "slippery pulse", and "wiry pulse", based on the result. Essentially, the data processing circuit can be any type of circuit that generates biological information indicative of a body condition based on the pulse wave analysis data MKD.

(2) In the above first embodiment, the pulse wave signal Vm detection site is the base of the finger, and the second to sixth embodiments were described with the back of the wrist as a typical detection site. However, the sensor unit can be appropriately modified in design so that any part of the skin can be used as a pulse wave signal Vm detection site, including, around the neck, the ear lobes, and the wrist.

(3) In the above preferred embodiments, the spectral sensitivity characteristic of the photodiodes 32 and 33 was described by way of example as that indicated by the solid line in FIG. 6, but they can alternatively have a peak wavelength of approximately 950 nm as indicated by the dotted line in FIG. 6. It is known that, in general, blood flow within approximately 3 mm from the skin surface can be measured if light having a wavelength of 300 nm to 600 nm is used for the detection light. This is because short wavelength light is easily absorbed or dispersed by body tissues. Good resistance to the effects of outside light can therefore be achieved if the wavelength range of the detection light is from 300 nm to 600 nm because outside light in the 300 nm to 600 nm wavelength range will be absorbed and dispersed by body tissues. However, special devices with the spectral sensitivity limited to this range are expensive. On the other hand, photodiodes exhibiting a spectral sensitivity characteristic as described in the above embodiments or as indicated by the dotted line in FIG. 6 are low cost and exhibit stable characteristics. Because the effects of outside light can be cancelled in the above embodiments, the pulse wave signal Vm can be accurately detected using a photodiode exhibiting a spectral sensitivity characteristic as indicated by the solid line or dotted line in FIG. 6 without limiting the wavelength of detected light to 300 nm to 600 nm.

TEXT IN THE FIGURES

Figure 16:
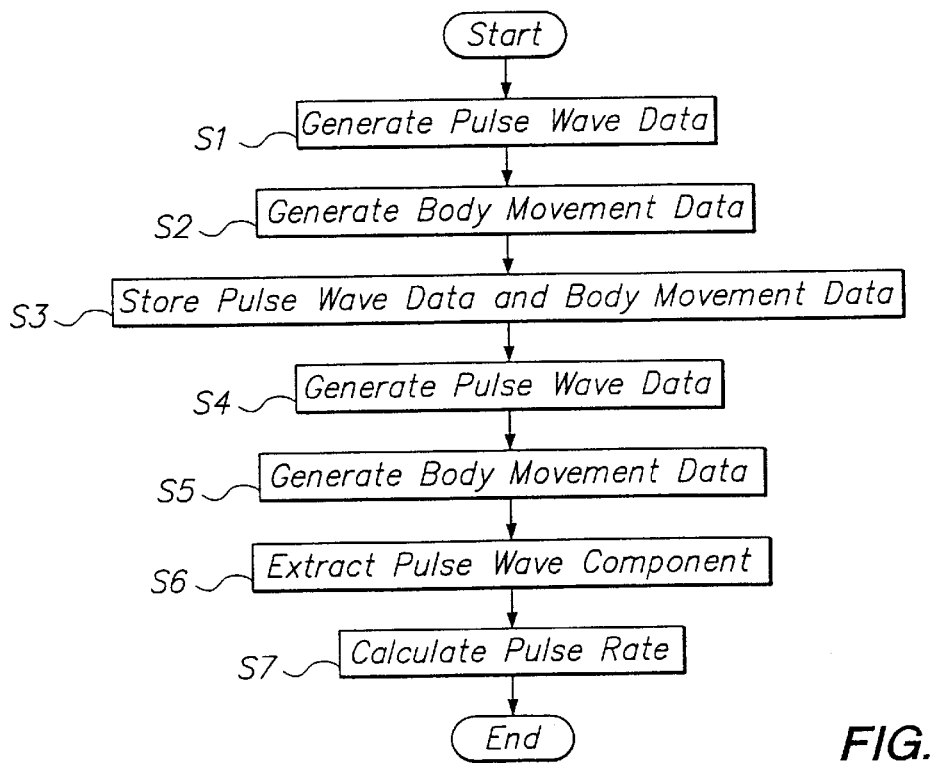
FIG. 16 is a flow chart of the operation of data processing circuit 50 according to this preferred embodiment.
Figure 31:
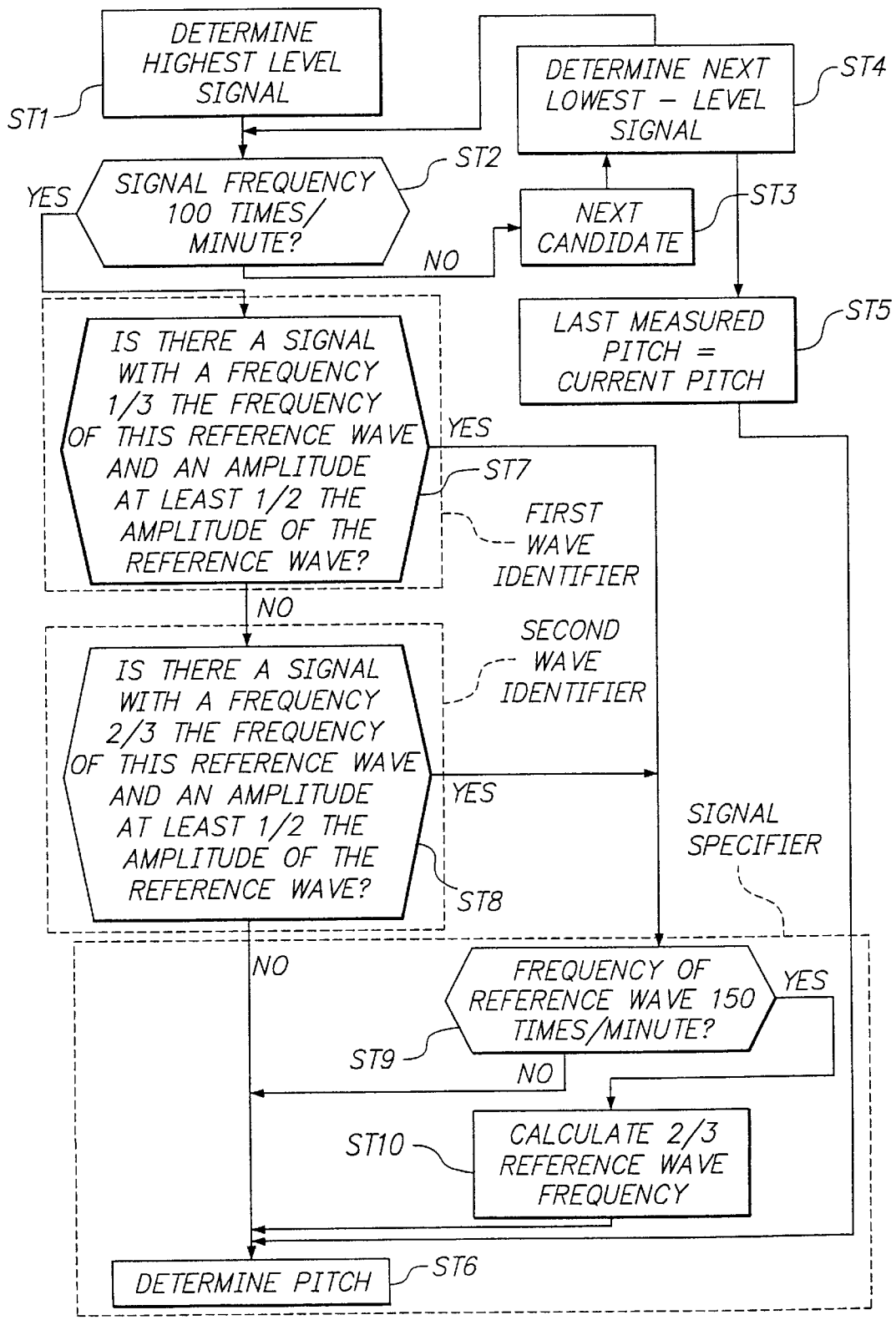
FIG. 31 is a flow chart of the pitch calculation process of pitch calculator 540 according to this second embodiment.

FIG. 2
  FINGER
FIG. 3
31 LED
20 CABLE
<- TO THE MAIN UNIT
37 TRANSPARENT GLASS
34 OPAMP
36 CIRCUIT BOARD
33 PHOTODIODE
35 CIRCUIT ELEMENT
32 PHOTODIODE
FIG. 4
20 CABLE
36 CIRCUIT BOARD
31 LED
37 TRANSPARENT GLASS
33 PHOTODIODE
38 TOP CASE
39 BOTTOM CASE
32 PHOTODIODE
34 OPAMP
FIG. 5
TO CABLE 20
FIG. 7
  RELATIVE POWER (%)
  WAVELENGTH (nm)
FIG. 8
CURRENT
  LUMINANCE INCREASES
VOLTAGE
  LUMINANCE INCREASES
FIG. 10
FROM 30--> 51 PULSE WAVE SIGNAL CONVERTER
FROM 60--> 52 BODY MOVEMENT SIGNAL CONVERTER
53 MEMORY
54 PULSE WAVE FREQUENCY ANALYZER
55 BODY MOVEMENT FREQUENCY ANALYZER
56 PULSE WAVE COMPONENT EXTRACTOR
57 PULSE RATE CALCULATOR
FIG. 12
NOISE SOURCE N
30 SENSOR UNIT
30' COMPARATIVE SENSOR UNIT
A AMPLIFIER
S FREQUENCY ANALYZER
FIG. 13
SPECTRUM POWER
FREQUENCY (Hz)
FIG. 14
SPECTRUM POWER
FREQUENCY (Hz)
Sn (none)
FIG. 15
• COMPARATIVE SENSOR UNIT
▫ SENSOR UNIT
* NOISE SPECTRUM POWER
Q=[noise spectrum power/pulse wave spectrum power+*] 100
OUTSIDE LIGHT NOISE POWER (LUMINANCE DIFFERENCE) (10,000 lux)
FIG. 16
START
S1 Generate pulse wave data
S2 Generate body movement data
S3 Store pulse wave data and body movement data
S4 Generate pulse wave analysis data
S5 Generate body movement analysis data
S6 Extract pulse wave component
S7 Calculate pulse rate
END
FIG. 17
(a) SPECTRUM POWER
  FREQUENCY (Hz)
(b) SPECTRUM POWER
  FREQUENCY (Hz)
(c) SPECTRUM POWER
  FREQUENCY (Hz)
FIG. 18
20 CABLE
<- TO THE MAIN UNIT 37 TRANSPARENT GLASS
31 LED
34 OPAMP
36 CIRCUIT BOARD
33 PHOTODIODE
35 CIRCUIT ELEMENT
32 PHOTODIODE
FIG. 20
A1 LIGHT EMITTING MEANS
B1 PHOTODETECTION MEANS
FIG. 21
ABSORPTION
TIME
I4: ARTERIAL BLOOD ABSORPTION COMPONENT
I3: VENOUS BLOOD ABSORPTION COMPONENT
I2: TISSUE ABSORPTION COMPONENT
FIG. 22
BLOOD PRESSURE
LEFT VENTRICLE
AORTA
ARTERY
BLOOD CAPILLARIES
SMALL VEINS
VEINS
LARGE VEINS
(DOTTED LINES INDICATE AVERAGE)
FIG. 23
MOLECULAR EXTINCTION COEFFICIENT (I/cm*mM)
WAVELENGTH (nm)
FIG. 24
RELATIVE POWER
WAVELENGTH (nm)
FIG. 25
TO CABLE 20
FIG. 26
FROM 300
52 BODY MOVEMENT SIGNAL CONVERTER
53 MEMORY
55 BODY MOVEMENT FREQUENCY ANALYZER
540 PITCH CALCULATOR
541 SIGNAL SPECIFIER
542 FIRST WAVE IDENTIFIER
543 SECOND WAVE IDENTIFIER
544 SIGNAL DISCRIMINATOR
FIG. 27
(A) POWER
    FREQUENCY (TIMES/MINUTE)
(B) POWER
    FREQUENCY (TIMES/MINUTE)
FIG. 28
RELATIVE POWER
WAVELENGTH (nm)
FIG. 29
TIME (SECONDS)
POWER
FREQUENCY (Hz)
FIG. 30
TIME (SECONDS)
POWER
FREQUENCY (Hz)
FIG. 31
ST1 Determine highest level signal
ST2 Signal frequency_100 times/minute?
ST3 Next candidate
ST4 Determine next lowest-level signal
ST5 Last measured pitch=current pitch
ST6 Determine pitch
ST7 Is there a signal with a frequency ⅓ the frequency of this reference wave and an amplitude at least ½ the amplitude of the reference wave? (first wave identifier)
ST8 Is there a signal with a frequency ⅔ the frequency of this reference wave and an amplitude at least ½ the amplitude of the reference wave? (second wave identifier)
ST9 Frequency of reference wave_150 times/minute?
ST10 Calculate ⅔ reference wave frequency
(SIGNAL SPECIFIER)
FIG. 34
340 DIFFERENCE OPERATOR
FIG. 37
FROM 301 -> Vm
51 PULSE WAVE SIGNAL CONVERTER
53 MEMORY
54 PULSE WAVE FREQUENCY ANALYZER
57 PULSE RATE CALCULATOR
FIG. 38
TIME (SECONDS)
POWER
FREQUENCY (Hz)
FIG. 40
FROM 301 -> Vm
51 PULSE WAVE SIGNAL CONVERTER
53 MEMORY
58 AUTOCORRELATION OPERATOR
54 PULSE WAVE FREQUENCY ANALYZER
57 PULSE RATE CALCULATOR
FIG. 41
TIME (SECONDS)
POWER
FREQUENCY (Hz)
FIG. 42
TIME (SECONDS)
POWER
FREQUENCY (Hz)
FIG. 43
TIME (SECONDS)
POWER
FREQUENCY (Hz)
FIG. 44
TIME (SECONDS)
POWER
FREQUENCY (Hz)
FIG. 45
51 PULSE WAVE SIGNAL CONVERTER
52 BODY MOVEMENT SIGNAL CONVERTER
53 MEMORY
58 AUTOCORRELATION OPERATOR
54 PULSE WAVE FREQUENCY ANALYZER
57 PULSE RATE CALCULATOR
59 S/N RATIO EVALUATION MEANS
55 BODY MOVEMENT FREQUENCY ANALYZER
540 PITCH CALCULATOR
FIG. 48
PULSE SPECTRUM/BODY MOVEMENT SPECTRUM
WAVELENGTH (NM)
FIG. 49
PULSE SPECTRUM/BODY MOVEMENT SPECTRUM
WAVELENGTH (nm)

What is claimed is:

1. A reflection type photodetection apparatus, having a light emitting element for emitting light to a detected object, for detecting the intensity of light reflected by the detected object, said reflection type photodetection apparatus comprising:

a first photoelectric conversion element for receiving and converting light reflected by the detected object and externally-sourced light to a first electrical output signal;

a second photoelectric conversion element for receiving and converting externally-sourced light to a second electrical output signal; and a difference means for detecting and outputting a difference signal representing a difference between the first output signal of the first photoelectric conversion element and the second output signal of the second photoelectric conversion element;

wherein the first photoelectric conversion element, second photoelectric conversion element, and light emitting element are arranged so that a distance from a photodetection center of the second photoelectric conversion element to a light emitting center of the light emitting element is different from a distance from the light emitting center of the light emitting element to a photodetection center of the first photoelectric conversion element, and the first photoelectric conversion element and second photoelectric conversion element are positioned so that externally-sourced light reaches each with substantially equal intensity, such that the intensity of light reflected by the detected object can be detected without significant affect from externally-sourced light.

2. A reflected light detection method for detecting the intensity of light reflected by a detected object using a reflection type photodetection apparatus having a light emitting element for emitting light to the detected object, a first photoelectric conversion element for receiving and converting light to a first electrical signal, and a second photoelectric conversion element for receiving and converting light to a second electrical signal, said reflected light detection method comprising:

a step for emitting light from the light emitting element to the detected object;

a step for generating the first electrical signal by detecting and photoelectrically converting light reflected by the detected object and externally-sourced light by means of the first photoelectric conversion element;

a step for generating the second electrical signal by detecting and photoelectrically converting externally-sourced light by means of the second photoelectric conversion element; and a step for detecting the intensity of the light reflected by the detected object, without significant affect from externally-source light, by calculating a difference between the first signal and second signal.

3. A biological information measuring apparatus having a reflection type photodetection apparatus as set forth in claim 1, wherein:

the light emitting element emits light to a detection site on a human body, the difference signal outputted by the difference detection means represents pulsation in blood flow, and based on the difference signal biological information indicative of a body condition is measured.

4. A biological information measuring apparatus comprising:

a light emitting means for emitting light to a detection site of a body, and a photodetection means for detecting of light emitted by the light emitting means to the body and generating a body movement signal according to the detected light quantity, for measuring movement of the body based on the body movement signal;

wherein the body movement signal is generated based on the quantity of detected light in a wavelength range of 600 nm and above.

5. A biological information measurement method for emitting light to a detection site of a body, comprising:

detecting the emitted light to the body;

generating a body movement signal based on the detected light quantity, and measuring movement of the body based on the body movement signal; and generating the body movement signal based on the quantity of detected light in a wavelength range of 600 nm and above.

6. The biological information measuring apparatus as set forth in claim 4, wherein the wavelength of the light emitted from the light emitting means is 600 nm or above.

7. The biological information measuring apparatus as set forth in claim 4, wherein the wavelength of light received by the photodetection means from the light emitting means is 600 nm or above.

8. A biological information measuring apparatus as set forth in claim 4, further comprising:

a frequency analysis means for frequency analyzing the body movement signal generated by the photodetection means, and generating a body movement spectrum; and a pitch detection means for extracting a fundamental frequency based on the body movement spectrum generated by the frequency analysis means, and detecting a body movement pitch of the body based on the extracted fundamental frequency.

9. A biological information measuring apparatus comprising:

a body movement detection means, having a first light emitting means for emitting light to a detection site on a body, for detecting light emitted by the first light emitting means to the body, and generating a body movement signal according to the amount of detected light;

a pulse wave detection means, having a second light emitting means for emitting light to a detection site on the body, for detecting light emitted by the second light emitting means to the body, and generating a pulse wave signal according to the amount of detected light; and a biological information generating means for generating biological information indicative of a body condition based on the body movement signal and pulse wave signal;

wherein the body movement detection means generates the body movement signal based on the quantity of detected light in a wavelength range of 600 nm or greater, and the pulse wave detection means generates the pulse wave signal based on the quantity of detected light in a wavelength range of 600 nm or below.

10. A biological information measurement method for measuring biological information indicative of a body condition, said method comprising:

a step for emitting light to a detection site on the body, detecting the light emitted to the detection site on the body, and generating a body movement signal according to the amount of detected light, where the amount of detected light measured is in a wavelength range of 600 nm or above;

a step for emitting light to a detection site on the body, detecting the light emitted to the detection site on the body, and generating a pulse wave signal according to the amount of detected light, where the amount of detected light measured is in a wavelength range of 600 nm or below; and a step for generating biological information indicative of a body condition based on the body movement signal and pulse wave signal.

11. The biological information measuring apparatus as set forth in claim 9, wherein the biological information generating means comprises a comparison operator for comparing the body movement signal and pulse wave signal, and generating biological information based on the result of the comparison.

12. The biological information measuring apparatus as set forth in claim 11, wherein the comparison operator subtracts the body movement signal from the pulse wave signal, and outputs a difference signal.

13. The biological information measuring apparatus as set forth in claim 12, wherein the biological information generating means frequency analyzes the difference signal output by the comparison operator to generate pulse wave analysis data from which the body movement component is removed, and generates biological information for the body based on the pulse wave analysis data.

14. The biological information measuring apparatus as set forth in claim 12, wherein the biological information generating means applies an autocorrelation function to the difference signal output by the comparison operator to generate autocorrelated pulse wave data, and generates biological information based on the autocorrelated pulse wave data.

15. The biological information measuring apparatus as set forth in claim 12, wherein the biological information generating means detects a degree of irregularity in body movement based on the body movement signal, determines whether to perform an autocorrelation operation based on the result of the degree of irregularity detection, applies an autocorrelation function to the difference signal output by the comparison operator to generate autocorrelated pulse wave data if an autocorrelation operation is to be performed, and generates biological information based on the autocorrelated pulse wave data, or generates biological information based on the difference signal if an autocorrelation operation is not performed.

16. The biological information measuring apparatus as set forth in claim 12, wherein a photodetection means of the body movement detection means is a first photodiode for outputting a first electrical signal according to the amount of light detected by the first photodiode;

a photodetection means of the pulse wave detection means is a second photodiode for outputting a second electrical signal according to the amount of light detected by the second photodiode; and the comparison operator outputs the difference signal from a node connected in series with the first photodiode and second photodiode.

17. A biological information measuring apparatus comprising:

light emitting means for emitting light to a wrist or arm; and photodetection means for detecting light emitted by the light emitting means to the body and generating a pulse wave signal according to the amount of detected light;

wherein biological information for the body is generated based on a pulse wave signal measured in a 500 nm to 600 nm wavelength range and a body movement signal measured in a wavelength range of 600 nm and above.

18. The biological information measuring apparatus as set forth in claim 17, wherein the primary wavelength of light emitted by the light emitting means is 500 nm to 600 nm.

19. The biological information measuring apparatus as set forth in claim 17, wherein the primary wavelength of light detected by the photodetection means is 500 nm to 600 nm.

* * * * *

UNITED STATES PATENT AND TRADEMARK OFFICE
CERTIFICATE OF CORRECTION

PATENT NO.    : 6,198,951 B1                                    Page 1 of 1
DATED         : March 6, 2001
INVENTOR(S)   : Tsukasa Kosuda et al.

It is certified that error appears in the above-identified patent and that said Letters Patent is hereby corrected as shown below:

Title page,
Title, change "REFLECTION PHOTODETECTOR AND BIOLOGICAL INFORMATION MEASURING INSTRUMENT" to -- REFLECTION TYPE PHOTODECTECTION APPARATUS, AND BIOLOGICAL INFORMATION MEASURING APPARATUS --.

Column 39,
Line 4, insert -- detection -- after "difference".

Signed and Sealed this

Fourteenth Day of May, 2002

Attest:

JAMES E. ROGAN
Attesting Officer            Director of the United States Patent and Trademark Office